US012766508B2

(12) United States Patent
Pais et al.

(10) Patent No.: US 12,766,508 B2
(45) Date of Patent: Oct. 20, 2026

(54) SAMPLE PROCESSING DEVICE COMPRISING MAGNETIC AND MECHANICAL ACTUATING ELEMENTS USING LINEAR OR ROTATIONAL MOTION AND METHODS OF USE THEREOF

(71) Applicant: Novel Microdevices, Inc., Baltimore, MD (US)

(72) Inventors: Andrea Maria Dominic Pais, Baltimore, MD (US); Rohan Joseph Pais, Baltimore, MD (US)

(73) Assignee: Novel Microdevices, Inc., Baltimore, MD (US)

( * ) Notice: Subject to any disclaimer, the term of this patent is extended or adjusted under 35 U.S.C. 154(b) by 535 days.

(21) Appl. No.: 17/569,884

(22) Filed: Jan. 6, 2022

(65) Prior Publication Data

US 2022/0371008 A1 Nov. 24, 2022

Related U.S. Application Data

(63) Continuation of application No. 15/747,301, filed as application No. PCT/US2016/043911 on Jul. 25, 2016, now Pat. No. 11,260,392.

(Continued)

(51) Int. Cl.
*B01L 3/00* (2006.01)
*B01F 31/441* (2022.01)

(Continued)

(52) U.S. Cl.
CPC ........ *B01L 3/50273* (2013.01); *B01F 31/441* (2022.01); *B01F 33/30* (2022.01); *B01F 33/3017* (2022.01); *B01F 33/452* (2022.01); *B01L 3/0293* (2013.01); *B01L 3/502738* (2013.01); *B01L 7/00* (2013.01); *B01L 7/52* (2013.01); *G01N 1/10* (2013.01); *G01N 1/38* (2013.01); *G01N 33/487* (2013.01); *B01L 3/502715* (2013.01); *B01L 3/50825* (2013.01); *B01L 2200/027* (2013.01); *B01L 2200/0689* (2013.01); *B01L 2200/16* (2013.01); *B01L 2300/045* (2013.01); *B01L 2300/0681* (2013.01); *B01L 2300/0816* (2013.01); *B01L 2300/0867* (2013.01);

(Continued)

(58) Field of Classification Search
None
See application file for complete search history.

(56) References Cited

U.S. PATENT DOCUMENTS 4,789,639 A 12/1988 Fleming
8,747,004 B1 6/2014 Mcpherson (Continued)

FOREIGN PATENT DOCUMENTS

CN 1409761 4/2003
CN 1448715 A 10/2003

(Continued)

*Primary Examiner* — Lore R Jarrett
(74) *Attorney, Agent, or Firm* — FISHERBROYLES, LLP

(57) ABSTRACT

An apparatus and method for simple, low power, automated processing of biological samples through multiple preparation and assay steps. The apparatus and methods described facilitate the point-of-care implementation of diagnostic assays. The apparatus includes mechanical actuating elements using linear and/or rotational motion.

18 Claims, 51 Drawing Sheets

1, 3, 5 are permanent magnets on the top actuator element
2, 4, 6 are permanent magnets on the bottom actuator element

Related U.S. Application Data

(60) Provisional application No. 62/331,635, filed on May 4, 2016, provisional application No. 62/261,577, filed on Dec. 1, 2015, provisional application No. 62/196,816, filed on Jul. 24, 2015.

(51) Int. Cl.

| | |
|---|---|
| ***B01F 33/30*** | (2022.01) |
| ***B01F 33/301*** | (2022.01) |
| ***B01F 33/452*** | (2022.01) |
| ***B01L 3/02*** | (2006.01) |
| ***B01L 7/00*** | (2006.01) |
| ***G01N 1/10*** | (2006.01) |
| ***G01N 1/38*** | (2006.01) |
| ***G01N 33/487*** | (2006.01) |
| ***G01N 35/00*** | (2006.01) |

(52) U.S. Cl.
CPC .................. *B01L 2300/1827* (2013.01); *B01L 2400/0478* (2013.01); *B01L 2400/0481* (2013.01); *B01L 2400/0605* (2013.01); *B01L 2400/0683* (2013.01); *G01N 2035/00128* (2013.01); *G01N 2035/00237* (2013.01); *G01N 2035/00534* (2013.01)

(56) References Cited

U.S. PATENT DOCUMENTS

| | | | | |
|---|---|---|---|---|
| 2003/0109057 | A1 | 6/2003 | Dicesare | |
| 2003/0233862 | A1 | 12/2003 | Wise | |
| 2005/0272113 | A1 | 12/2005 | Mosher | |
| 2007/0264649 | A1 | 11/2007 | Gumbrecht | |
| 2008/0190391 | A1 | 8/2008 | McElwee | |
| 2008/0206740 | A1 | 8/2008 | Skiffington | |
| 2009/0035746 | A1* | 2/2009 | Ehben | B01L 3/502761 435/283.1 |
| 2009/0075344 | A1 | 3/2009 | Green | |
| 2009/0143699 | A1 | 6/2009 | Wu | |
| 2009/0189464 | A1 | 7/2009 | Schilffarth | |
| 2010/0056383 | A1* | 3/2010 | Ririe | B01L 3/50273 506/7 |
| 2010/0081209 | A1 | 4/2010 | Brewer | |
| 2010/0311177 | A1 | 12/2010 | Wu | |
| 2010/0317093 | A1 | 12/2010 | Turewicz | |
| 2011/0100104 | A1 | 5/2011 | Pelssers | |
| 2011/0188339 | A1* | 8/2011 | Howell, Jr. | B01F 33/452 366/273 |
| 2012/0135443 | A1 | 5/2012 | Schultz | |
| 2012/0167672 | A1 | 7/2012 | Miller | |
| 2012/0168305 | A1 | 7/2012 | Hunter | |
| 2012/0295366 | A1* | 11/2012 | Zilch | B01L 3/502761 422/69 |
| 2013/0118900 | A1 | 5/2013 | Reimitz | |
| 2013/0130262 | A1* | 5/2013 | Battrell | B01L 3/50273 435/6.12 |
| 2013/0309136 | A1 | 11/2013 | Johnson | |
| 2014/0194305 | A1 | 7/2014 | Kayyem | |
| 2014/0212882 | A1* | 7/2014 | Handique | G01N 1/40 435/6.12 |
| 2014/0243706 | A1 | 8/2014 | El-Fahmawi | |
| 2015/0031036 | A1* | 1/2015 | Murayama | B01L 7/525 435/6.12 |
| 2015/0076008 | A1 | 3/2015 | Athanasiou | |
| 2015/0160135 | A1* | 6/2015 | Tibbe | B01D 71/0215 435/7.1 |

FOREIGN PATENT DOCUMENTS

| | | | |
|---|---|---|---|
| CN | 1639555 | A | 7/2005 |
| CN | 1804602 | | 7/2006 |
| CN | 1882835 | A | 12/2006 |
| CN | 1921803 | A | 2/2007 |
| CN | 201376965 | Y | 1/2010 |
| CN | 202351089 | | 7/2012 |
| CN | 103394410 | | 11/2013 |
| CN | 103562727 | | 2/2014 |
| CN | 104203411 | A | 12/2014 |
| CN | 104254595 | A | 12/2014 |
| DE | 102009035941 | | 2/2011 |
| DE | 102010036216 | A1 | 3/2012 |
| EP | 0371574 | | 6/1990 |
| EP | 1024354 | A1 | 8/2000 |
| EP | 2007651 | A2 | 12/2008 |
| JP | S5552929 | | 4/1980 |
| JP | H06313767 | | 11/1994 |
| JP | 2002105100 | | 4/2002 |
| JP | 2005021866 | | 1/2005 |
| JP | 2005300396 | | 10/2005 |
| JP | 2007101428 | | 4/2007 |
| JP | 2009505090 | | 2/2009 |
| JP | 2009128037 | A | 6/2009 |
| JP | 2011013043 | | 1/2011 |
| JP | 2012517595 | | 8/2012 |
| JP | 2013040879 | | 2/2013 |
| JP | 2013130548 | | 7/2013 |
| JP | 2013217707 | A | 10/2013 |
| JP | 2013228235 | A | 11/2013 |
| JP | 2014533176 | | 12/2014 |
| JP | 2015513102 | A | 4/2015 |
| WO | 9824548 | | 6/1998 |
| WO | 2005011867 | | 2/2005 |
| WO | 2005049856 | | 6/2005 |
| WO | 2005071388 | A1 | 8/2005 |
| WO | 2007129463 | A2 | 11/2007 |
| WO | 2008036997 | A1 | 4/2008 |
| WO | 2008076395 | A2 | 6/2008 |
| WO | 2009006641 | | 1/2009 |
| WO | 2011001646 | | 1/2011 |
| WO | 2014049371 | A2 | 4/2014 |
| WO | 2014149277 | A2 | 9/2014 |
| WO | 2015075447 | A1 | 5/2015 |
| WO | 2016027782 | A1 | 2/2016 |

* cited by examiner

Section AA 1, 3, 5 are permanent magnets on the top actuator element
2, 4, 6 are permanent magnets on the bottom actuator element

SAMPLE PROCESSING DEVICE COMPRISING MAGNETIC AND MECHANICAL ACTUATING ELEMENTS USING LINEAR OR ROTATIONAL MOTION AND METHODS OF USE THEREOF

CROSS-REFERENCE TO RELATED APPLICATIONS

The present application is a continuation of U.S. application Ser. No. 15,747,301 filed on Jan. 24, 2018, now issued U.S. Pat. No. 11,260,392, which was a 371 national phase entry of international application PCT/US2016/043911, filed Jul. 25, 2016, which claims the benefit of U.S. Provisional Application No. 62/196,816, filed Jul. 23, 2015; U.S. Provisional Application No. 62/261,577, filed Dec. 1, 2015; and U.S. Provisional Application No. 62/331,635, filed May 4, 2016; the entire contents of which are incorporated by reference herein in their entireties.

BACKGROUND

Point-of-Care ("POC") devices allow for convenient and rapid testing at the site of patient care. Accordingly, Sample-to-Answer and Lab-On-a-Chip ("LOC") systems, types of POC devices integrating microfluidics technology, have become increasingly popular. These LOCs integrate various lab functions, such as extraction, amplification, detection, interpretation, and reporting, previously performed manually and/or off-site, all on the same device. Because Sample-to-Answer and LOC testing are performed at the site of patient care and not in a lab facility, these types of tests have had issues with contamination control, particularly in steps which involve human interaction during the process. As such, there is a need to automate the sample processing within a sample-to-answer LOC that minimizes human interaction. These sample-to-answer and LOCs are generally a few square millimeters to a few square centimeters in size, and are often types of microelectromechanical systems ("MEMS"). MEMS that are capable of detecting and analyzing biological material such as here are generally referred to as Bio-MEMS.

Most POC diagnostic devices on the market are categorized as either high or moderate complexity under Clinical Laboratory Improvement Amendments ("CLIA"). These federal guidelines generally apply to clinical laboratory testing instruments on humans, except in certain conditions which allow for waiver of these guidelines. One of these conditions is when the device or instrument meets certain risk, error, and complexity requirements. In order to make a POC diagnostic test eligible to be CLIA-waived, the sample preparation and fluid handling steps need to be minimized. One way to minimize these steps is to store the reagents in a sealed device such as a blister or burst pouch to be released. Reagent delivery into a microfluidic chip commonly includes the use of pumps, such as syringe pumps or peristaltic pumps, and external reagent-filled bottles, syringes, or reservoirs. These systems are not only difficult to make portable, but also are complex due to the numerous components that have to be integrated together and the need for leak-free fluidic interfaces into the microfluidic chip. Methods to enable simple, miniaturized, and low-power automation of fluid handling have yet to be successfully implemented in the commercial state-of-the art. Accordingly, this has been seen as a roadblock preventing POC implementation in a majority of the multi-step bioassay tests that are still being conducted in large clinical facilities.

Complex bioassays that require multiple processing steps, including but not limited to pipetting, heating, cooling, mixing, washing, incubating, labeling, binding, and eluting, rely on expensive lab automation equipment to run the sample-to-answer sequence. Low-cost, low-power, miniaturized instrumentation for automation of the sample-to-answer sequence is yet to be realized and, as such, point-of-care microfluidic devices for running a sample-to-answer sequence rely on additional instrumentation that takes the form of a stand alone bench top or portable instrument to run the assay on a microfluidic device. Implementing separate instrumentation that can automate the sample processing steps on the microfluidic cartridge is seen as a way to keep the cost per test, and hence the cost of the cartridge, low. In systems developed for point-of-care applications, this can take the form of a portable bench top instrument with solenoid plungers, linear actuators, microcontrollers, and electronic circuitry to automate the sample processing sequence. While this instrumentation gives the user control over the sample processing sequence, it requires controlled environments and a considerable amount of electrical power to run. These point-of-care systems are not feasible in low resource settings where no infrastructure exists to run the instrument, or for home and non-hospital settings where laypersons either do not see the need or cannot afford to purchase a costly instrument for a test, or are not trained to operate the instrument that goes along with the test. As such, developing methods to enable, low power, stand-alone, inexpensive, and disposable instrumentation that can be directly integrated onto the microfluidic device and that can run the automated sample-to-answer sequence is seen as a roadblock for developing single use test devices that can run complex multi-step nucleic acid, protein, and immunoassays from sample-to-answer.

Disposable tests that do not require instrumentation to run them are limited to the following: 1) Simple Single Step Assays in which the sample is the only liquid and no reagents are used (these tests typically include dipstick tests such as urine test strips and pregnancy tests); and 2) Multi-Step Assays that are sold in the form of a kit comprising reagent vials and an instruction set wherein the user is relied upon to follow the instructions and dispense the reagents into different regions of the disposable test cartridge (these devices typically run immunoassays that do not require sample preparation steps).

Some examples of Multi-Step Assay devices include, but are not limited to, Chembio Diagnostic Systems, Inc.'s DPP® HIV ½ Assay, SURE CHECK® HIV ½, HIV ½ STAT-PAK®, and HIV ½ STAT-PAK® DIPSTICK tests. These tests rely on the user to manually perform a series of steps to complete the sequence. There is a risk for the test being performed incorrectly if the user is not skilled or does not follow the instructions correctly, thus results can vary depending on how the test was performed. Moreover, there is an additional risk of contamination when the reagents are not completely contained inside the device. Some harsh reagents that are harmful to handle without proper lab protocols, gloves, and equipment (e.g., fume hoods and lab infrastructure such as a contained biosafety facility) cannot be implemented in these kit tests unless the test is being performed by trained technicians in a contained facility.

Laypersons risk running a test incorrectly if the test is not simple and automated. As the test complexity increases beyond two or three steps, these manual kit-based tests fall short in their utility. Advances in nucleic acid amplification assays (e.g., isothermal assays such as loop-mediated-amplification) reduce the instrumentation burden for heating/ cooling thermal-cycling since these tests only require the sample to be held at a single temperature (usually between 60-70° C.). However, these tests still require multiple user initiated steps for completing the sample-to-answer sequence that require skilled operators or additional automation instrumentation.

Sample preparation is essential for many diagnostic assays involving the processing of biological samples. A biological sample typically goes through multiple complex processing steps before it is suitable to be used in an assay. These steps are required to isolate, concentrate, and/or purify the analyte of interest from a raw sample and to remove materials in the sample that can interfere with the desired assay. Sample processing steps often involve precise conditions for temperature, reagent volumes, and incubation times that need to be performed in a precise sequence and in a tightly controlled environment such as a laboratory setting. Conventional automation systems for sample processing involve highly complex and expensive instrumentation and skilled personnel to operate them. Since these systems are often placed in centralized labs, raw samples must frequently be properly stored and transferred to a lab at a different location for processing. These factors are associated with several limitations including high costs, delay in results, and compromised sample integrity due to shipping and improper storage.

The present invention provides methods and devices for simple, low power, automated processing of biological samples through multiple sample preparation and assay steps. The methods and devices described facilitate the point-of-care implementation of complex diagnostic assays in equipment-free, non-laboratory settings.

SUMMARY

In accordance with the present invention, various embodiments of sample-to-answer microfluidic devices with magnetic and mechanical actuating elements using linear or rotational motion automation and methods of use thereof are disclosed. In one embodiment, a microfluidic device is provided comprising:

- one or more cams comprising a cam shaft and a cam lobe;
- one or more rocker arms;
- a microfluidic cartridge comprising one or more fluidic channels, one or more reaction chambers, and one or more burst pouches comprising fluid and a frangible membrane seal; and
- a cam mechanism configured to rotate the cam shaft;

wherein the one or more cams are configured such that rotation of the cam shaft causes the cam lobes to actuate the one or more rocker arms, and wherein the one or more rocker arms are configured such that actuation causes the rocker arms to move from an open position to a closed position in which pressure is placed on the one or more burst pouches such that the frangible membrane is broken and the fluid is released into the one or more reaction chambers.

In some embodiments a plurality cam lobes and rocker arms are configured such that one full rotation of the cam shaft causes the rocker arms to place pressure on a plurality burst pouches in a temporally and spatially controlled manner. In some embodiments the one or more cam lobes and the one or more rocker arms are configured such that after the frangible membrane seal of the one or more burst pouches has been broken, the rocker arms remain in the closed position. In some embodiments the cam lobes are configured such that the rocker remains in the closed position after rupturing the pouch. In some embodiments the microfluidic device further comprises one or more diaphragm valves along the one or more fluidic channels, wherein the one or more cam lobes are configured such that rotation of the cam shaft causes the cam lobes to open and/or close the one or more diaphragm valves. In some embodiments the camshaft is configured to rotate via a wind-up spring mechanism.

In some embodiments the microfluidic device further comprises a sample prep chamber, wherein the sample prep chamber comprises a vehicle for DNA capture. In some embodiments the rotation speed of the cam shaft and the configuration of the plurality of cam lobes and the plurality of rocker arms enables bursting of the plurality of burst pouches in a temporally controlled manner to carry out wash steps of DNA purification. In some embodiments the microfluidic cartridge further comprises an amplification chamber, a heat sink, and a heater, wherein the heat sink and the heater are configured to intermittently cool and heat the amplification chamber upon actuation of the plurality of cam lobes and the plurality of rocker arms. In some embodiments the rotation speed of the cam shaft and the configuration of the plurality of cam lobes and the plurality of rocker arms enables the heat sink and the heater to intermittently cool and heat the amplification chamber in a temporally controlled manner to carry out PCR thermal cycling. In some embodiments the microfluidic cartridge further comprises a DNA hybridization chamber comprising a vehicle for DNA capture.

In another embodiment, a microfluidic device is provided comprising a microfluidic cartridge comprising:

- a plurality of reagent filled pouches;
- a reaction chamber; and
- a cam shaft;

wherein the cam shaft comprises a plurality of slots at angular positions along the cam shaft such that rotation of the cam shaft to a predetermined position causes one or more of the angular slots to form a flow channel between one or more of the reagent filled pouches and the reaction chamber.

In another embodiment, a reagent dispensing unit is provided comprising:

- a reagent pouch comprising a reagent and a frangible seal; and
- an integrated magnetic element configured to depress the reagent pouch when attracted by a magnetic field such that the frangible seal is broken. In some embodiments the magnetic element comprises a plunger. In some embodiments the magnetic element comprises a bead. In some embodiments comprises a sharp object.

In another embodiment, a microfluidic device is provided comprising:

- a fluid conduit;
- a reaction chamber; and
- the reagent dispensing unit as described elsewhere herein;

wherein the reagent dispensing unit is bonded to the microfluidic device such that a hermetic seal is formed, and wherein the reagent dispensing unit is configured to empty the reagent into the reaction chamber via the fluid conduit when the frangible seal is broken. In some embodiments the microfluidic device further comprises a trap, wherein the trap comprises loose magnetic material and is configured to hold the reagent pouch in a depressed position.

In another embodiment, a microfluidic device is provided comprising:

- a plurality of fluidic chambers fluidically connected to one another via valves; and
- a rotating shaft comprising permanent magnets arranged axially and radially with alternating poles on the periphery of the rotating shaft;

wherein each of the fluidic chambers comprises a trapped permanent magnet with a direction of motion restricted along a path perpendicular to the axis of the rotating shaft, and wherein the rotating shaft and fluidic chambers are configured such that rotation of the rotating shaft moves the permanent magnets for mixing of fluid within each of the fluidic chambers.

In another embodiment, a reagent pouch is provided comprising a point of rupture at a precise location in a frangible portion of a seal, wherein the reagent pouch comprises a magnetic element that is constrained to a particular area of the reagent pouch that directly overlays the frangible portion of the seal.

In another embodiment, a microfluidic device is provided comprising:

one or more linear actuation elements; and a microfluidic cassette;

wherein the one or more linear actuation elements comprise fixed magnetic elements for magnetic bead displacement, fluidic valve actuation, and/or reagent pouch bursting; and wherein the microfluidic cassette comprises stored reagent pouches with integrated magnetic plunger elements, reagent chambers for sample processing, a magnetic pivoting rocker valve featuring a non-magnetic plunger for controlling the movement of magnetic beads through a valve, and magnetically controlled valves comprising magnetic plungers comprising fixed magnetic elements for magnetic bead displacement. In some embodiments the one or more actuation elements are configured to slide under and/or on top of the microfluidic device. In some embodiments the actuation element is moved via a method selected from the group consisting of a motor, a wind-up spring, a hand crank, manual pushing, and a linear solenoid actuator.

In another embodiment, a microfluidic device is provided comprising:

one or more linear actuation elements; and a microfluidic cassette;

wherein the one or more linear actuation elements comprise a combination of fixed and partially trapped magnetic elements contained in their own trap such that their motion is restricted to one axis or direction for magnetic bead displacement, fluidic valve actuation, and/or reagent pouch bursting; and wherein the microfluidic cassette comprises stored reagent pouches with integrated magnetic plunger elements, reagent chambers for sample processing, a magnetic pivoting rocker valve featuring a non-magnetic plunger for controlling the movement of magnetic beads through a valve, and magnetically controlled valves comprising magnetic plungers comprising fixed magnetic elements for magnetic bead displacement. In some embodiments the one or more actuation elements are configured to slide under and/or on top of the microfluidic device. In some embodiments the actuation element is moved via a method selected from the group consisting of a motor, a wind-up spring, a hand crank, manual pushing, and a linear solenoid actuator.

In another embodiment, a microfluidic device is provided comprising a reagent pouch aligned with a magnetic plunger element integrated into a reaction chamber, wherein the magnetic plunger element is configured such that when it is attracted by a magnetic field it breaks a frangible seal of the reagent pouch, enters into the reagent pouch, and displaces reagents in the reagent pouch into the reaction chamber. In some embodiments the magnetic plunger element is located between a fluid inlet and the reagent pouch, further wherein the magnetic element has a notch that acts as a guide and restricts the flow of fluid to the reaction chamber through the guide notch, and wherein the guide notch is configured such that when the magnetic element plunger reaches its top most position, the flow of fluid into the reaction chamber is shut.

In another embodiment, a microfluidic device is provided comprising:

an actuating element with a plurality of partially trapped magnetic element housed inside a rotating shaft, wherein the rotating shaft is configured in a sleeve with a plurality of magnet traps;

a plurality of the reagent dispensing units as described elsewhere herein;

a mixing chamber; and a mixing chamber magnet. In some embodiments the microfluidic device further comprises fixed permanent magnets configured such that their opposite poles are aligned with the periphery of the rotating shaft, thereby causing a mixing chamber magnet to be attracted and repelled at a high frequency as the shaft rotates. In some embodiments the microfluidic device is configured such that as the rotating shaft rotates, a first reagent dispensing unit becomes aligned with a first partially trapped magnetic element whereby the first partially trapped magnet moves out of the rotating shaft and enters a first magnet trap in the sleeve, thereby enabling attraction of the magnetic element and breaking of the frangible seal on the pouch of the first reagent dispensing unit. In some embodiments the microfluidic device is configured such that as the rotating shaft continues to rotate, a second reagent dispensing unit becomes aligned with a second partially trapped magnetic element whereby the second partially trapped magnet moves out of the rotating shaft and enters a second magnet trap in the sleeve, thereby enabling attraction of the magnetic element and breaking of the frangible seal on the pouch of the second reagent dispensing unit. In some embodiments the microfluidic device is configured such that after stored reagents have been dispensed, the rotating shaft can rotate at a high RPM to enable mixing by causing the fixed permanent magnet in the shaft to present alternating poles to the mixing magnet at a high frequency.

In another embodiment, the system mechanically ensures that a magnetic plunger element cannot return to its original position after actuation, wherein the sleeve containing the magnetic plunger comprises at least one cantilevered ratchet element molded into its wall such that the magnet deflects the ratchet in this position but when the magnet is displaced the ratchet will retract and make it impossible for the magnetic plunger to move back to its initial position. In some embodiments, the ratchet is replaced by a spring-loaded ball.

In another embodiment, a sample processing system is provided that employs an actuating element comprising a magnet moving on a track, wherein the magnet attracts magnetic beads onto which biomolecules are bound. As the magnet moves along the track it drags the magnetic beads in a microfluidic chip. The path of the track is through a plurality of reagent chambers such that the magnetic beads are moved through all the reagent chambers at the appropriate time, with the magnet finally moving through a trap, such as a ball trap. In some embodiments, the magnetic element is mounted on a carriage, which is free to move along the sliding rail. The entire sliding rail traverses the length of the microfluidic device by moving along a linear screw. In another embodiment of this system, the linear screw is replaced by a rack and pinion mechanism. In another embodiment, one or more magnets may be arranged on the track to perform multiple sample processing steps either sequentially or in parallel.

In another embodiment, microfluidic devices employing rotational actuating elements are provided for automating the sample processing sequence. Additionally, some embodiments of the sample-processing device can employ a combination of one or more rotational and linear actuating elements depending on the design and sample processing requirements to gain control over the x, y, z and r axes.

In another embodiment, magnetic plunger element valves for controlling fluid flow in an exemplary microfluidic device are provided. In some embodiments, a magnetic pivoting rocker valve with a non-magnetic plunger element is provided, for example wherein a valve a rocker with a magnetic element pivots (or rotates) about its axis. When an external magnetic field is brought into proximity it will attract the magnetic element on the rocker and cause the plunger to push down on the diaphragm valve thereby stopping the flow of fluid through the channel. When the magnetic field is removed the rocker returns to its original position and flow in the channel can resume.

In another embodiment, a diaphragm or pinch valve is provided that can be depressed on a microfluidic device using a magnetic plunger element. When an external magnetic field is brought into proximity of the magnetic plunger element, it attracts the plunger towards it thereby depressing the diaphragm valve and stopping flow in the channel.

In another embodiment, permanent magnets are affixed axially and radially on the periphery of a rotating shaft in such a way as to exhibit alternating polarity along the length of the rotating shaft. The fluidic device or container contains a second permanent magnet material trapped inside it such that its motion is restricted to one axis. When the rotating shaft is placed in proximity to a fluidic device or container, the permanent magnetic material inside the container experiences alternating attraction and repulsion forces, resulting in reciprocating and shearing motion inside the fluidic device or container.

In another embodiment of the system, a magnetic plunger element is constrained such that it can only move in the direction required to squeeze the pouch of a reagent dispensing unit, break the frangible seal and dispense reagents through the fluid conduit and into the microfluidic device.

In some embodiments the reaction chambers in the microfluidic device are designed such that they can be compressed to move fluids from one reaction chamber to another.

In another embodiment, a microfluidic device for sample preparation for nucleic acid amplification tests is provided. The fluidic wells are connected to one or more reagent dispensing units containing miscible reagents through an inlet fluidic conduit entering at the bottom of each fluidic well. The fluidic well volumes are designed such they are only partially filled by the miscible liquid reagents entering through the inlet fluidic conduits. Upon completion of the filling of the fluidic wells, a reagent dispensing unit containing an immiscible liquid is actuated and its contents are dispensed into the fluidic device through the primary fluidic conduit, which fills the empty volume in the primary fluidic conduit and fluidic wells, thereby creating a fluidic pathway and at the same time forming a barrier between the miscible liquids in the fluidic wells so as to prevent them from mixing together.

In another embodiment, a microfluidic cartridge for magnetic bead based sample preparation is provided comprising fluidic wells, fluidic conduits, stored liquid reagent reservoirs and valves. The microfluidic cartridge is sandwiched between top and bottom actuator elements that comprise permanent magnets and projections or protrusions. The permanent magnets and protrusions are spatially arranged such that they perform different steps of an assay automation sequence with precise timing, depending on their position and speed of the actuator elements as the microfluidic cartridge rotates in close proximity to the actuator elements. Assay steps that may be performed include dispensing stored reagents into fluidic wells, opening and closing valves to control the direction of fluid flow, opening and closing vents, capturing, resuspending, and moving magnetic beads between wells.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Having thus described the presently disclosed subject matter in general terms, reference will now be made to the accompanying Figures, which are not necessarily drawn to scale.

Figure 1A:
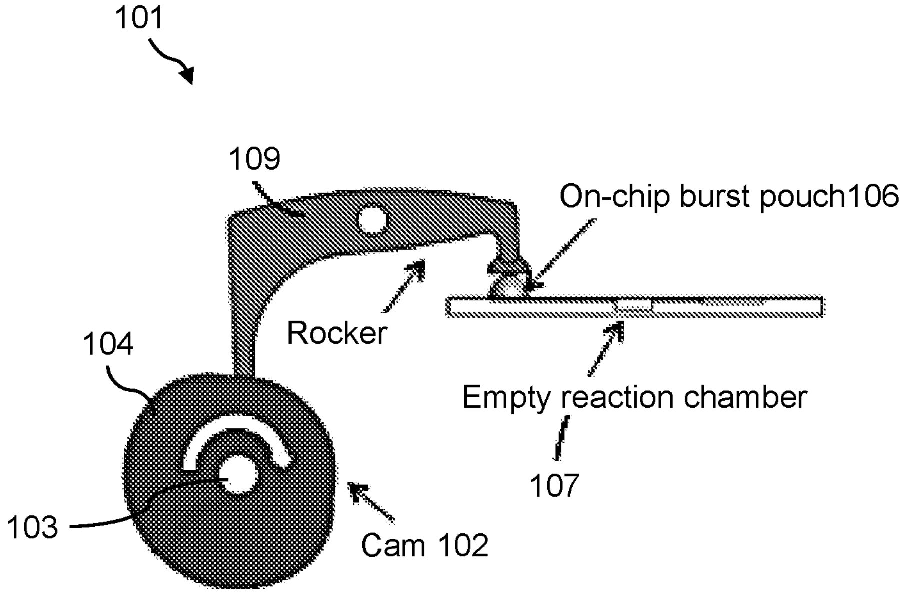

FIG. 1A is a side view of an embodiment of a sample-to-answer microfluidic device before actuation of the rocker arm.

Figure 1B:
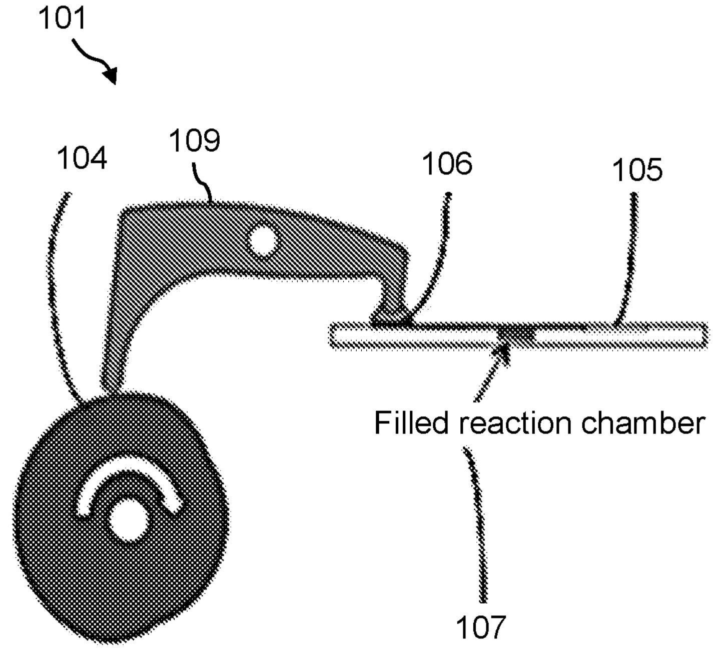

FIG. 1B is a side view of the embodiment of the sample-to-answer microfluidic device after actuation of the rocker arm.

Figure 2:
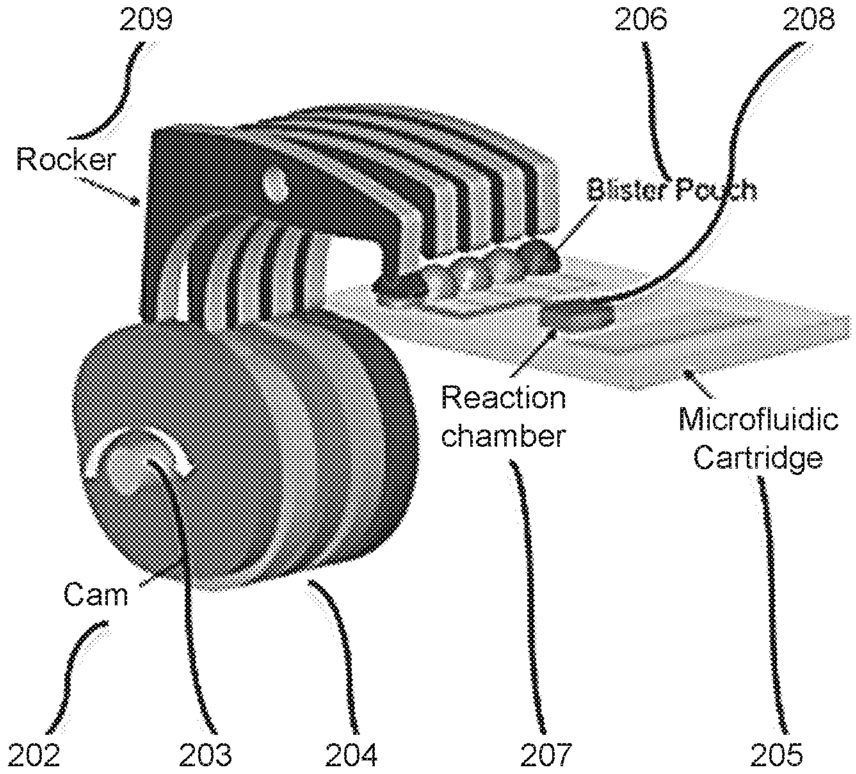

FIG. 2 is a perspective view of an exemplary sample-to-answer microfluidic device.

Figure 3:
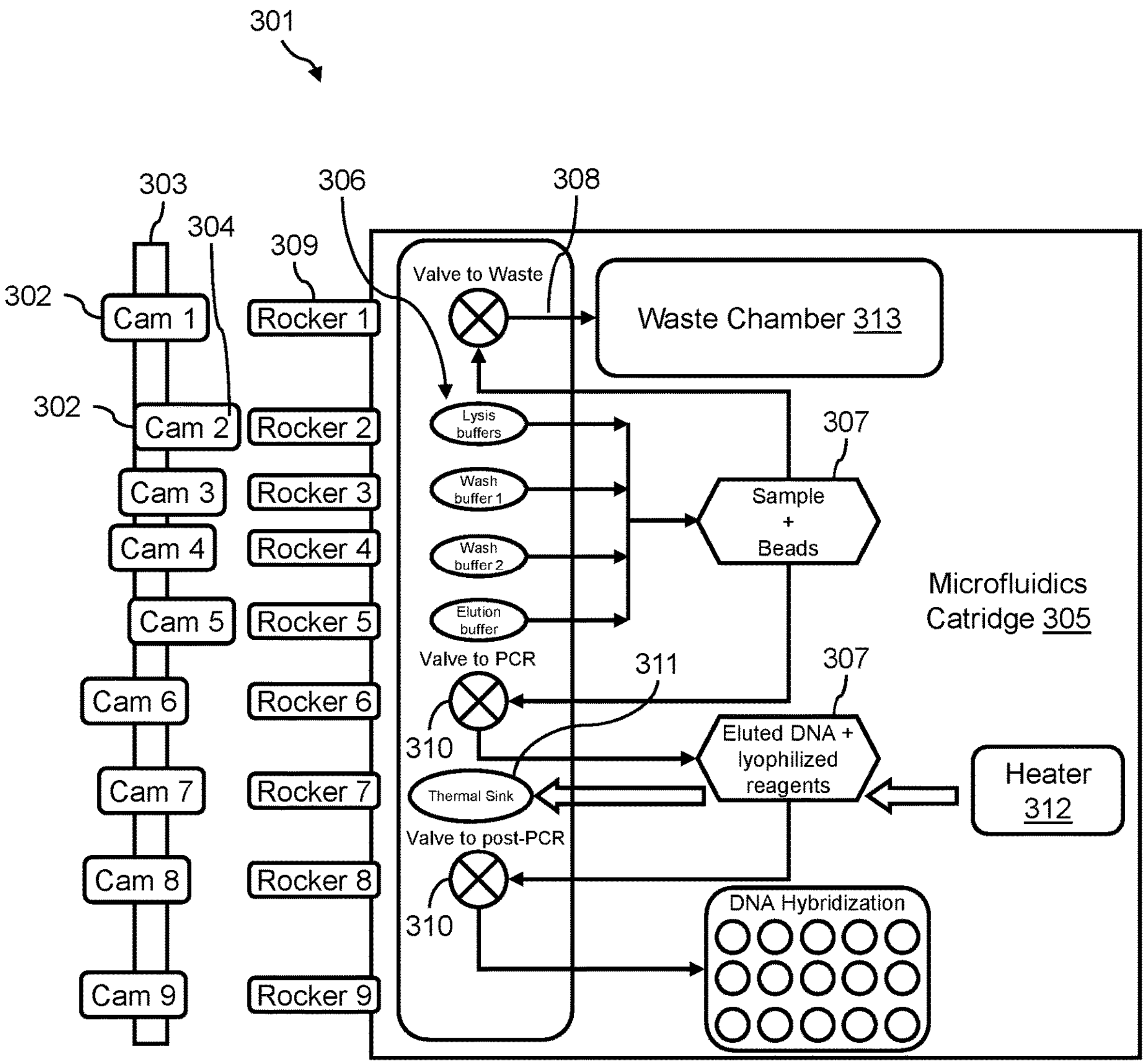

FIG. 3 is a block diagram of an exemplary microfluidic device with a sample analysis functions.

Figure 4:
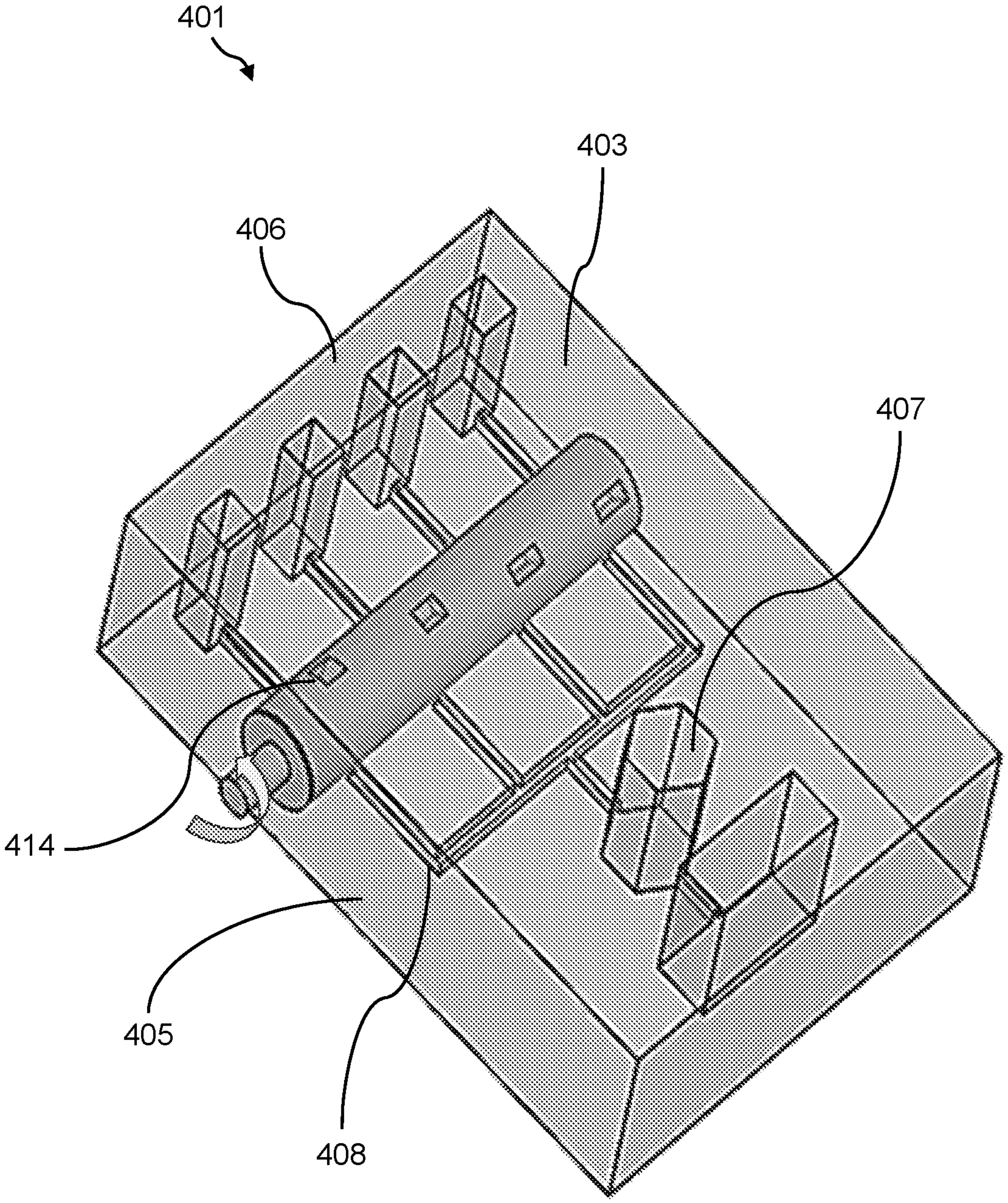

FIG. 4 is a top-view of an embodiment of an exemplary microfluidic device using a revolving port design.

Figure 5A:
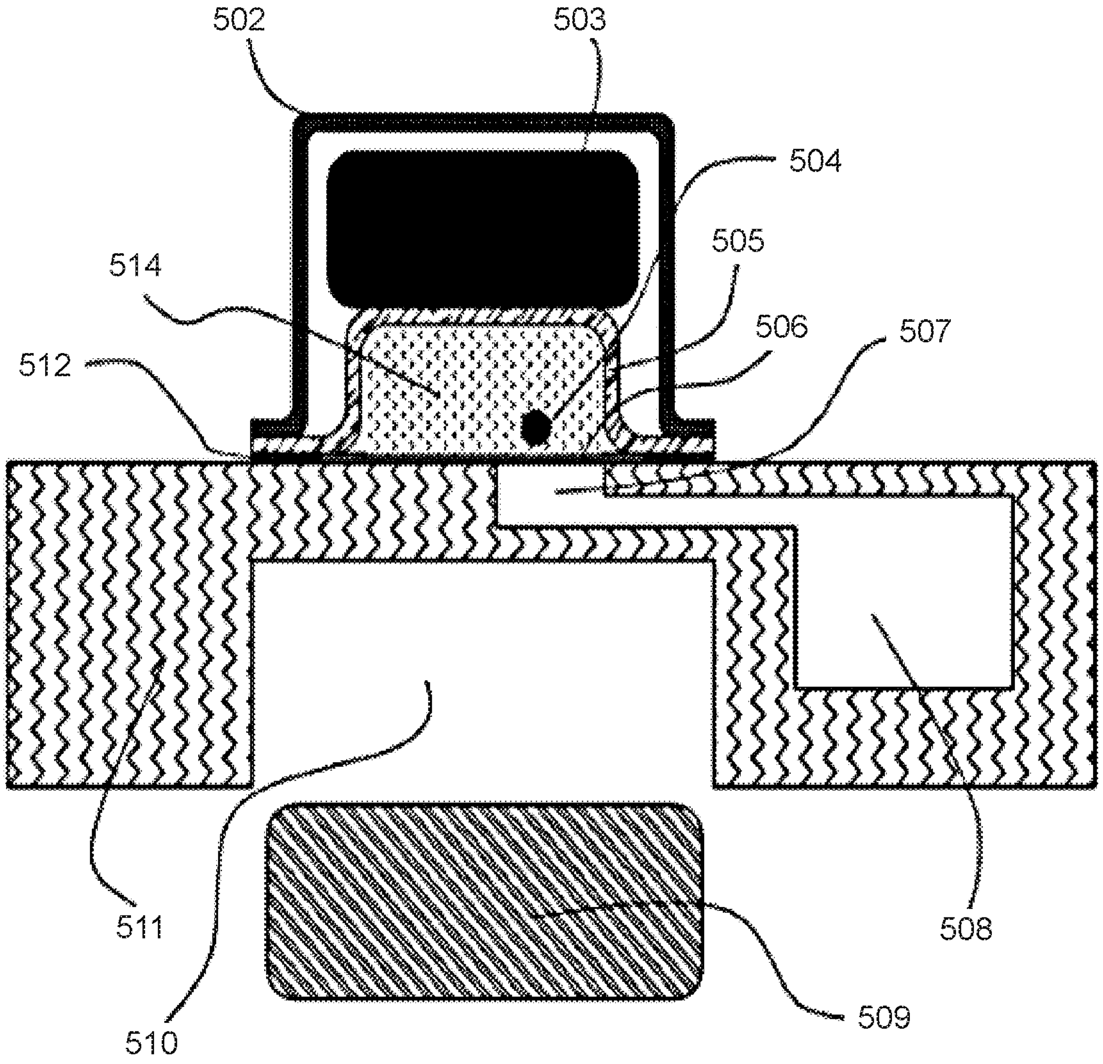
Figure 5B:
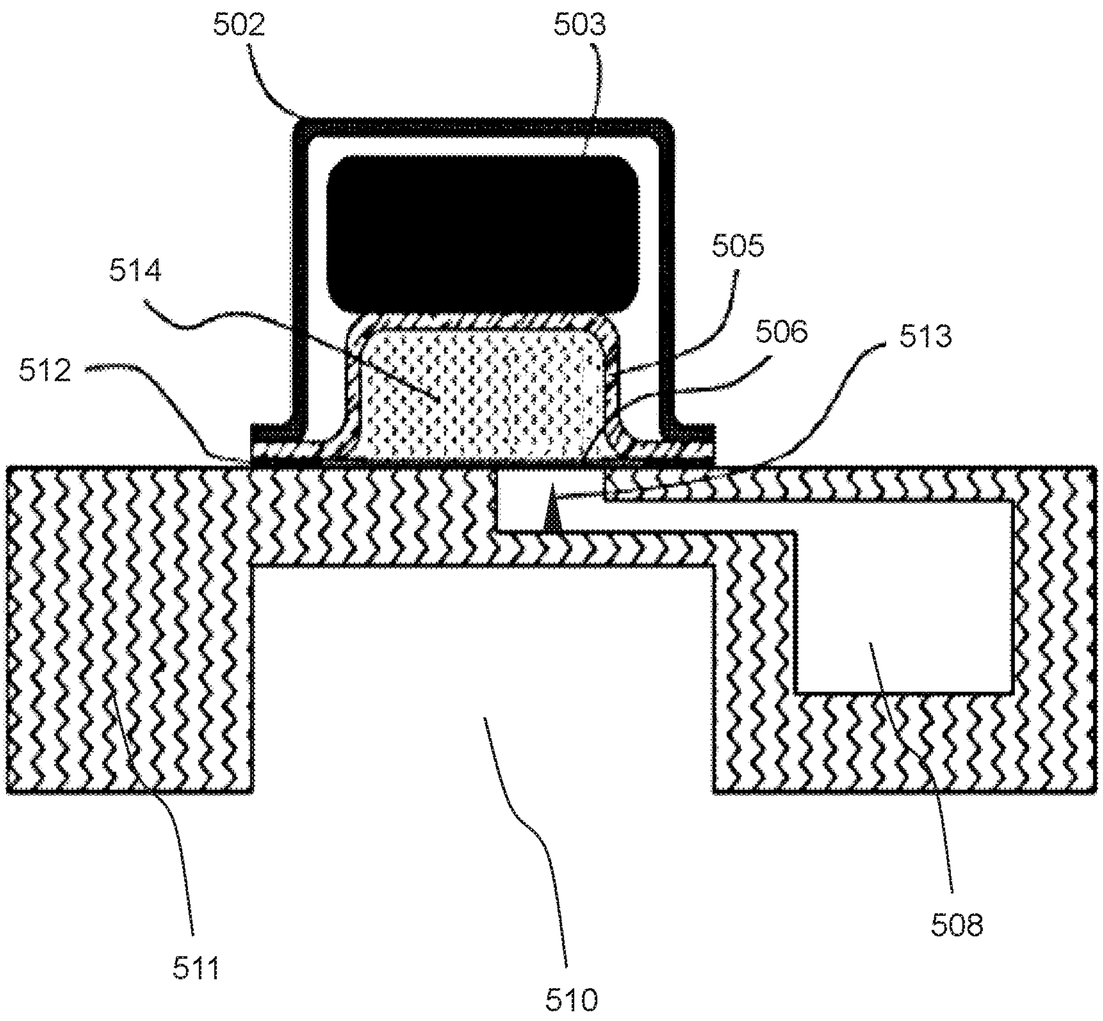

FIGS. 5A-5B generally show a cross-sectional view of the Reagent Dispensing Unit (RDU) with FIG. SA showing a magnetic breaking element inside the reagent pouch, and FIG. 5B showing a sharp object inside the microfluidic device for rupturing the frangible seal.

Figure 6A:
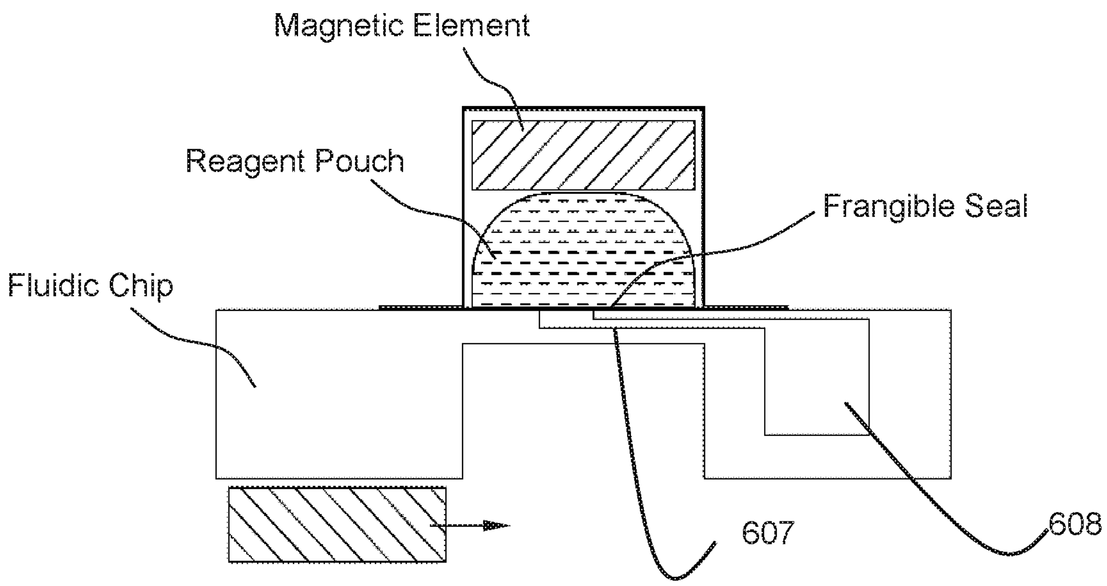
Figure 6B:
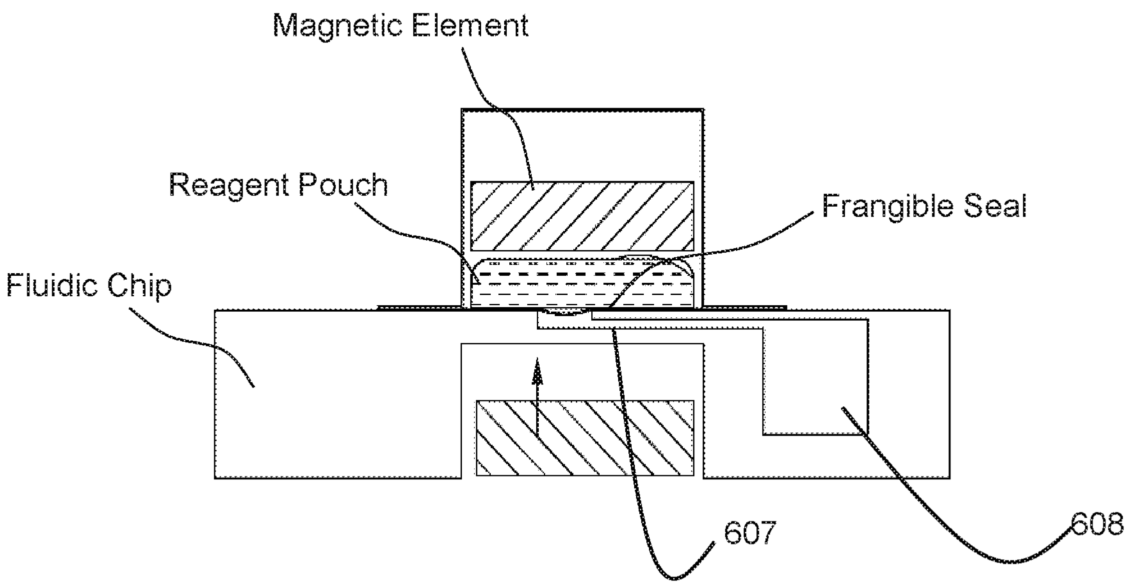
Figure 6C:
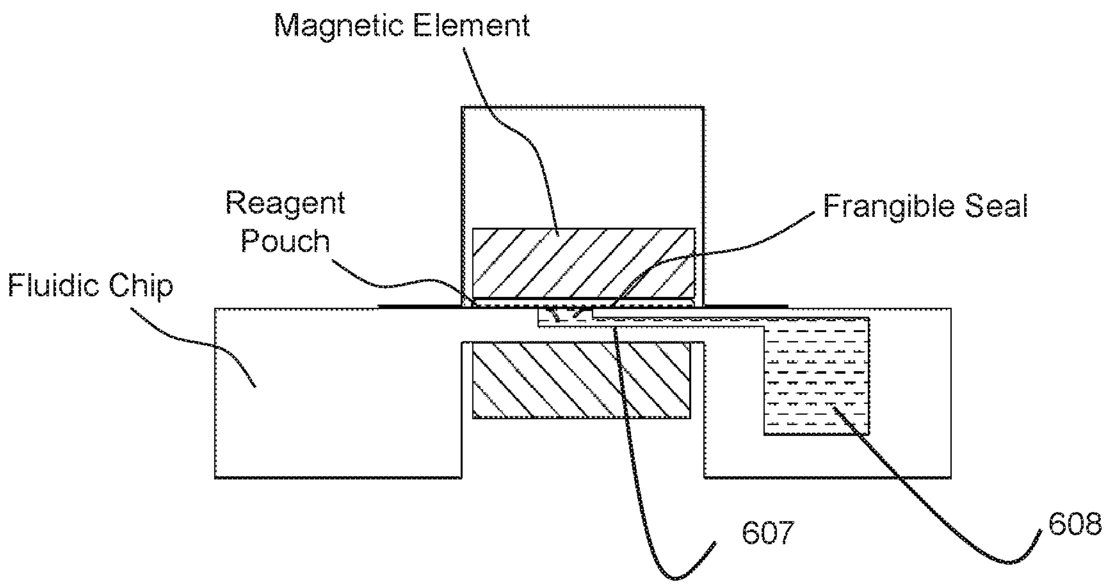

FIGS. 6A-6C show a reagent pouch being burst by the magnetic element plunger.

Figure 7A:
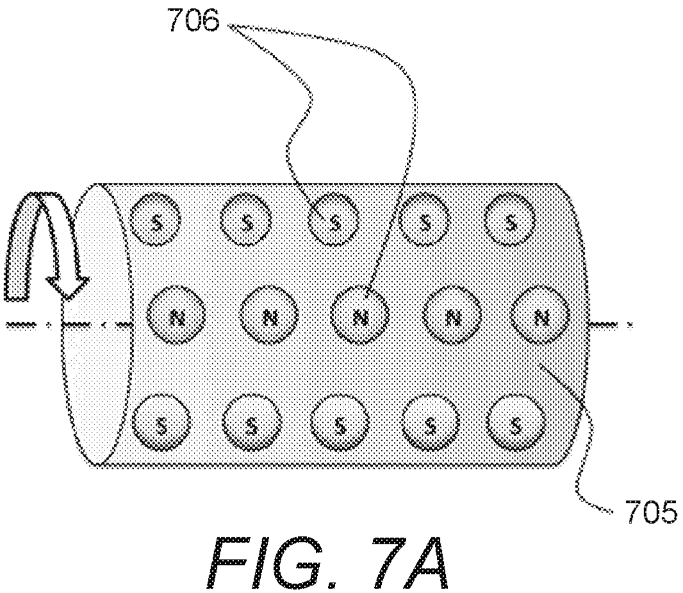
Figure 7B:
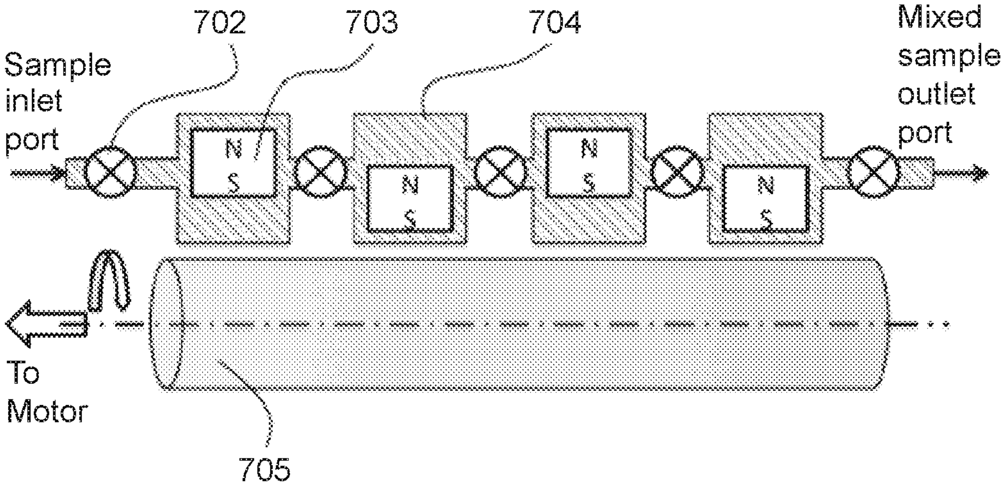

FIGS. 7A-7B generally show an embodiment of a rotating shaft based magnetic mixing element with FIG. 7A depicting a rotating shaft with permanent magnets arranged axially and radially with alternating poles on the periphery of the rotating shaft, and FIG. 7B depicting a multi-chamber fluidic mixing system with rotating shaft in its proximity.

Figure 8:
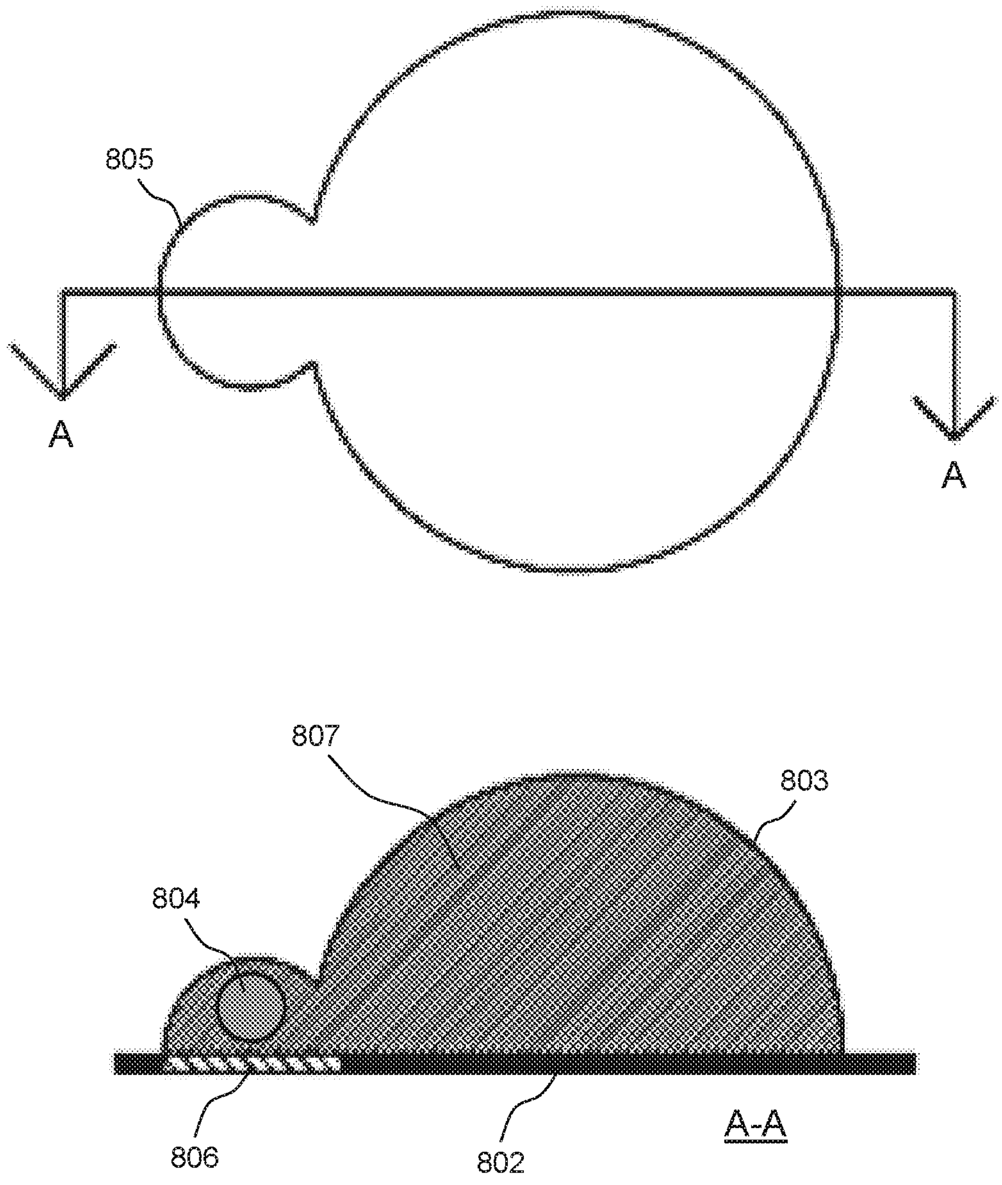

FIG. 8 shows a top view and section AA view of exemplary reagent pouch for the RDU containing a constrained magnetic breaking element for controlling the rupture point on the frangible seal.

Figure 9A:
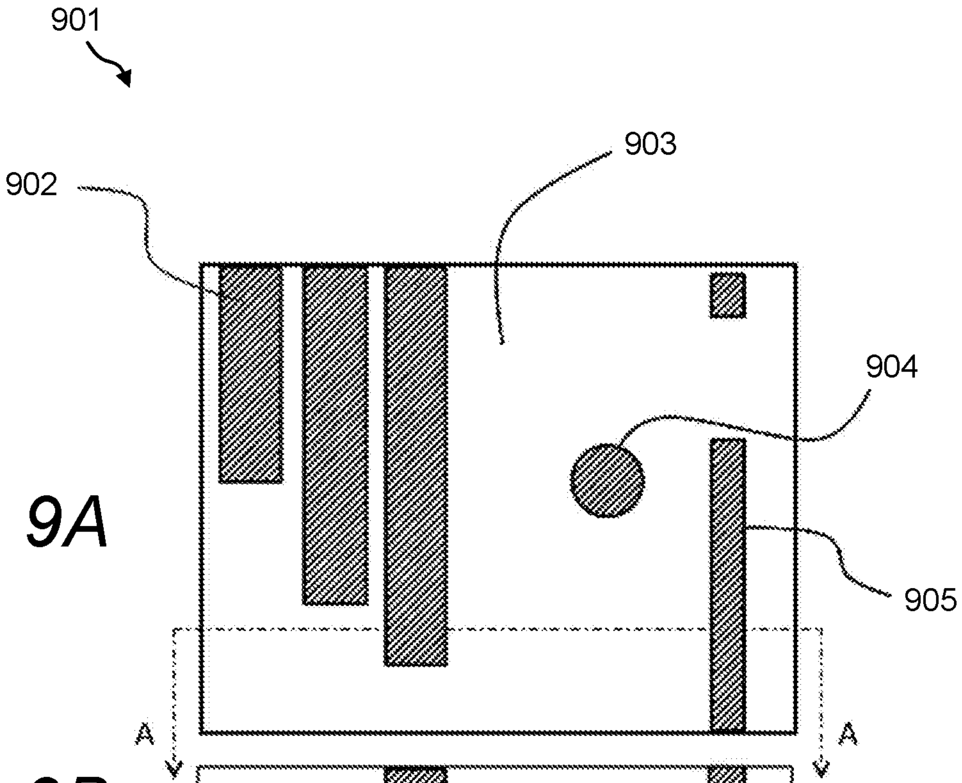
Figure 9B:
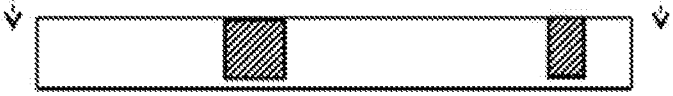
Figure 9C:
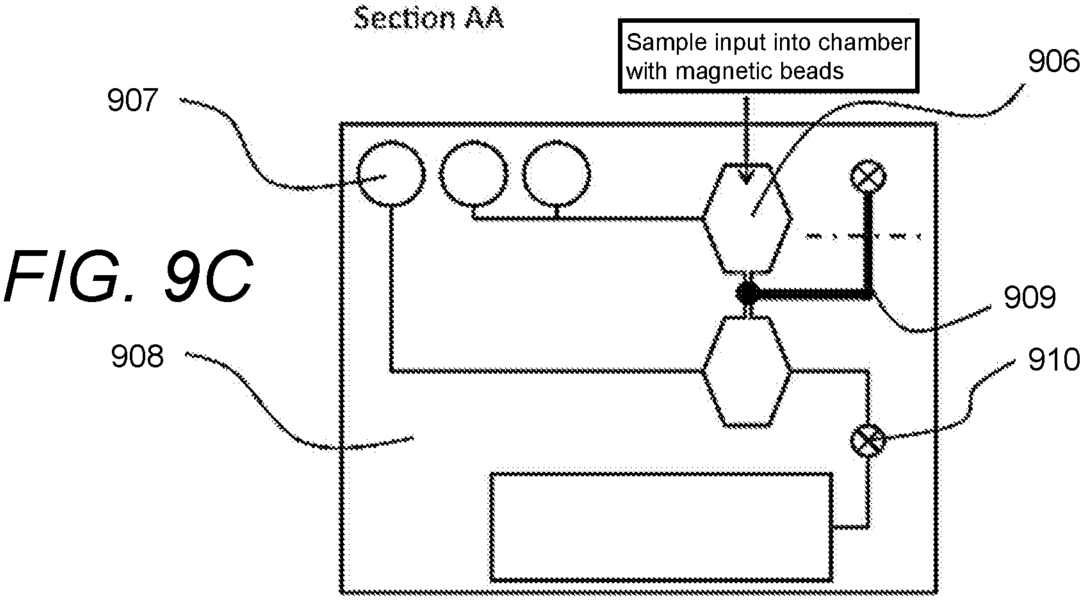
Figure 10A:
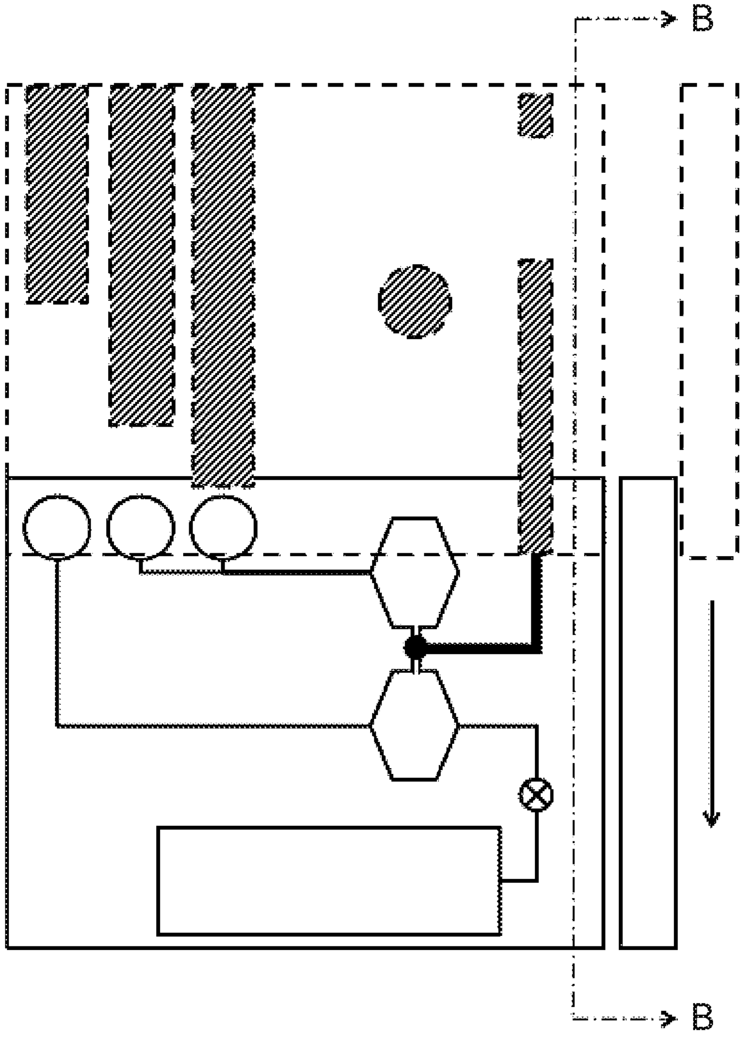
Figure 10B:
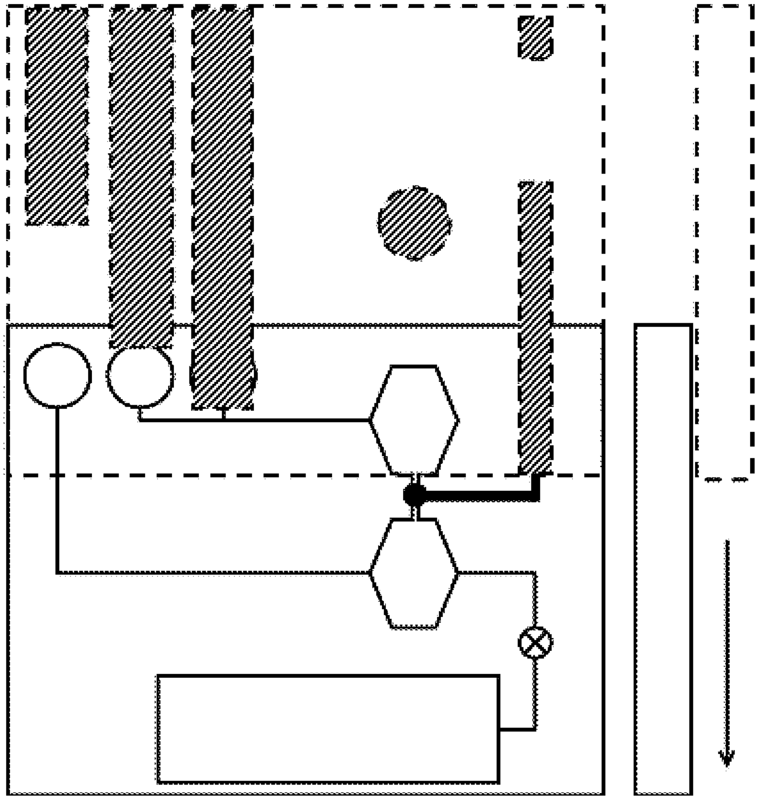
Figure 10C:
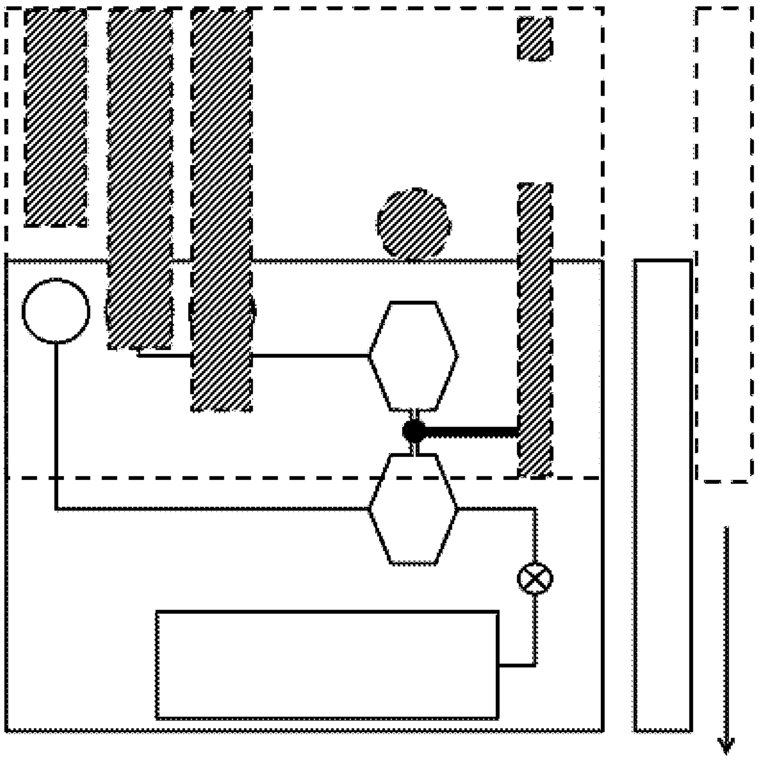
Figure 10D:
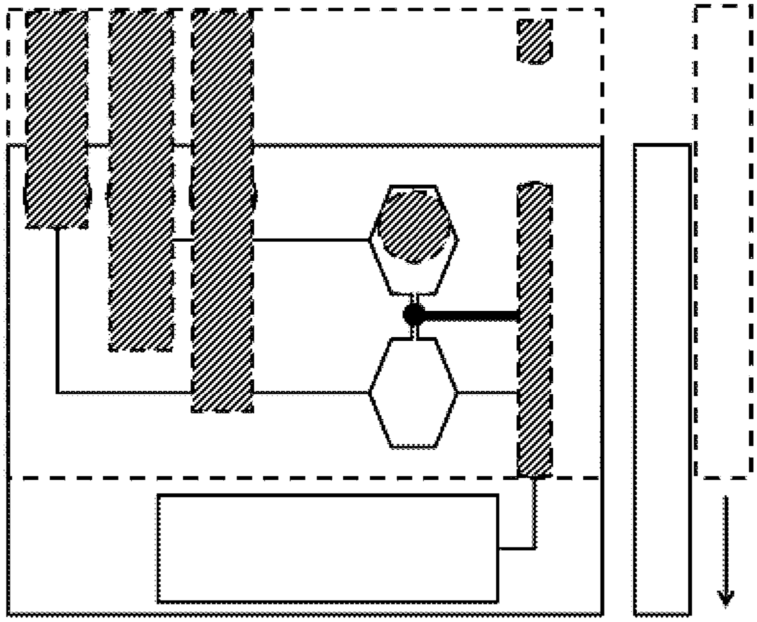
Figure 10E:
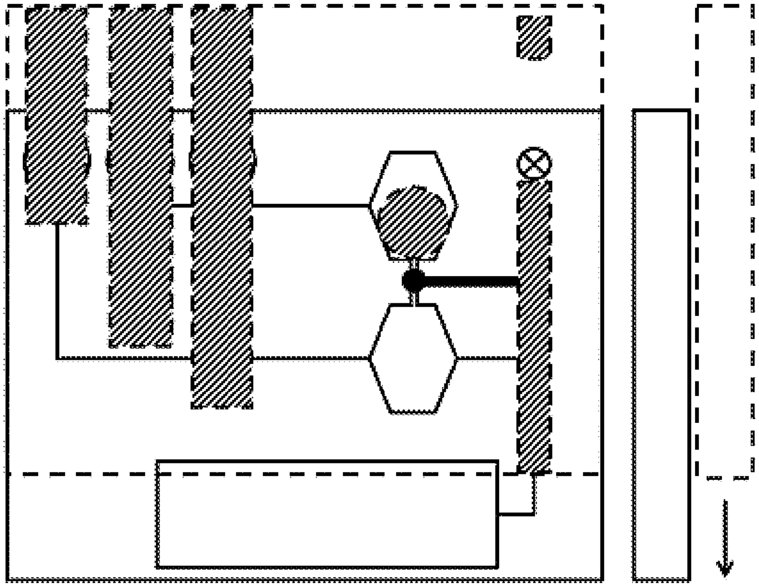
Figure 10F:
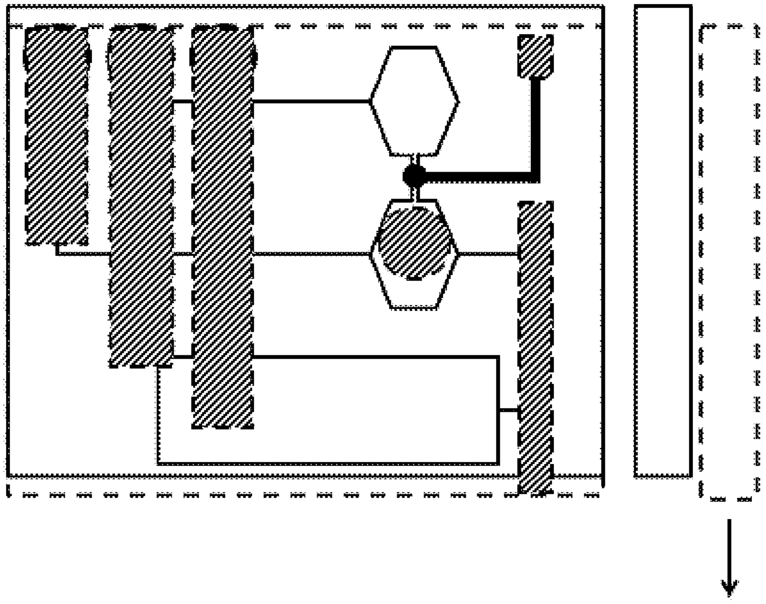
Figure 11A:
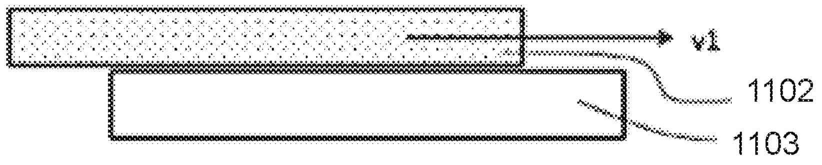
Figure 11B:
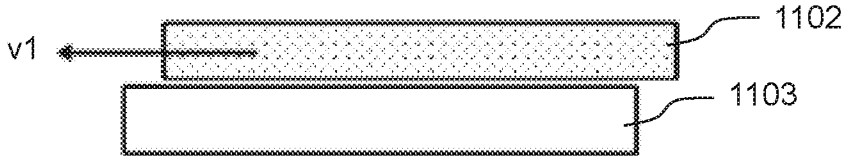
Figure 11C:
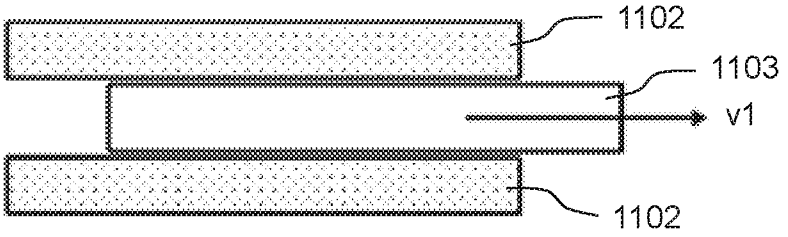
Figure 11D:
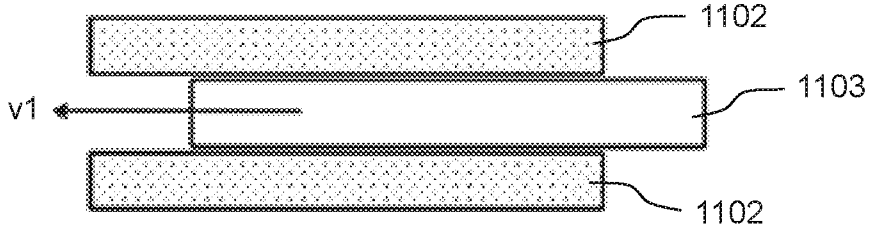
Figure 11E:
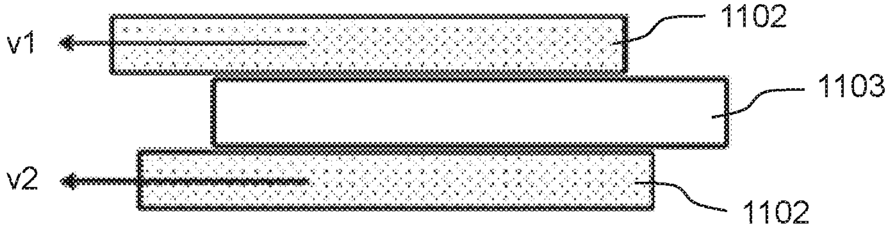
Figure 11F:
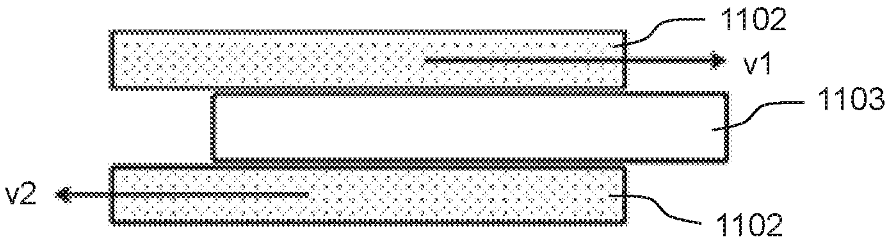

FIGS. 9A-9C show an exemplary microfluidic device for sample processing with FIG. 9A showing a top view of linear actuating element, FIG. 9B showing a section AA view of linear actuating element, and FIG. 9C showing a top view of microfluidic cassette.

FIGS. 10A-10F show various instances of the sample processing sequence as the actuating element slides under the microfluidic cassette.

FIGS. 11A-11F show examples of different implementations of linear actuating elements.

FIGS. 12A-12D show examples of a microfluidic sample-processing device comprising an actuating element with a combination of fixed and partially trapped magnetic elements.

Figure 13A:
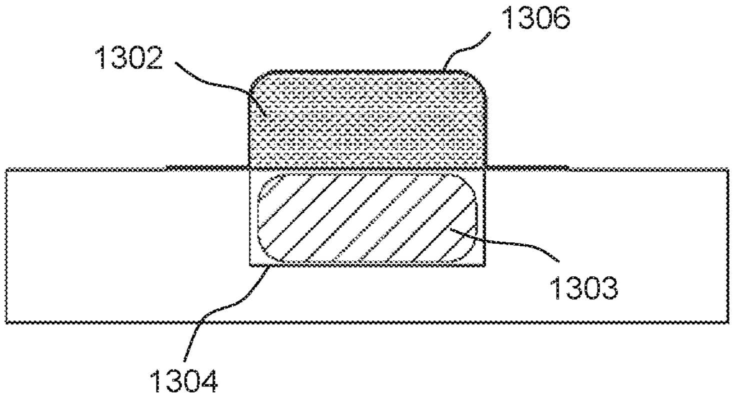
Figure 13B:
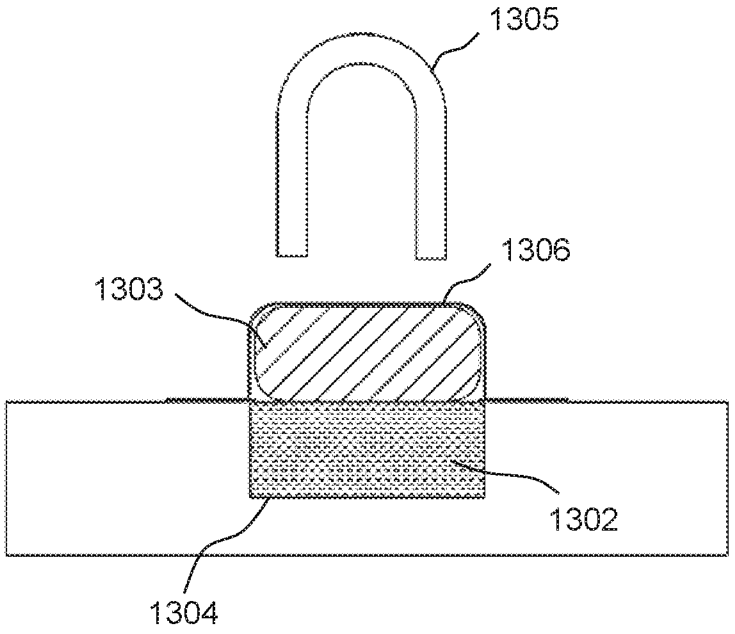

FIGS. 13A-13B generally show a cross-sectional view of an exemplary microfluidic device with FIG. 13A showing a magnetic plunger element integrated into the reaction chamber, and FIG. 13B showing a magnetic plunger element attracted to magnetic field thereby breaking the frangible seal and displacing the contents of the reagent pouch into the reaction chamber.

Figure 14A:
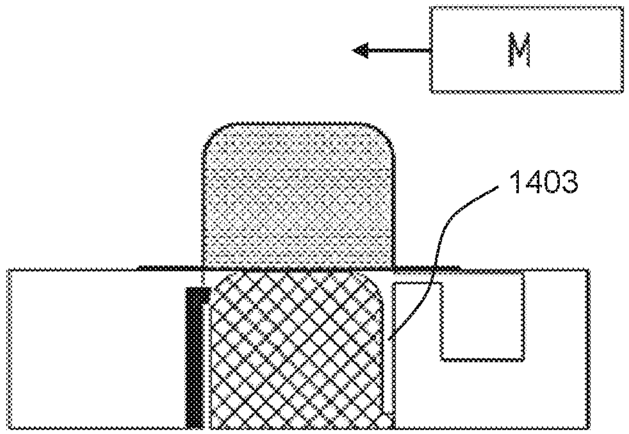
Figure 14B:
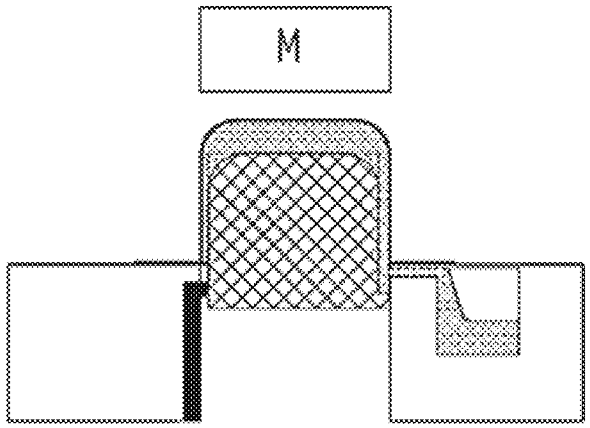
Figure 14C:
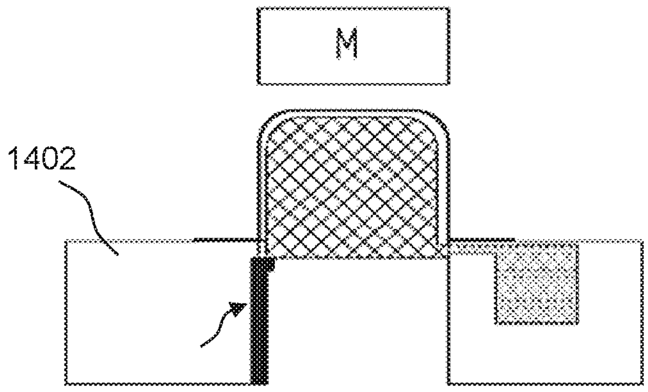

FIGS. 14A-14C generally show a cross-sectional view of an exemplary microfluidic device with FIG. 14A showing a notched magnetic plunger element integrated into the reaction chamber, FIG. 14B showing a notched magnetic plunger element attracted to magnetic field thereby breaking the frangible seal and displacing the contents of the reagent pouch into the reaction chamber, FIG. 14C showing a notched magnetic plunger element closing the inlet port of the fluidic conduit after dispensing the reagents of reagent pouch; and ratchet element to mechanically hold the magnetic plunger element in permanently sealed position even in the absence of the external magnetic field.

Figure 15:
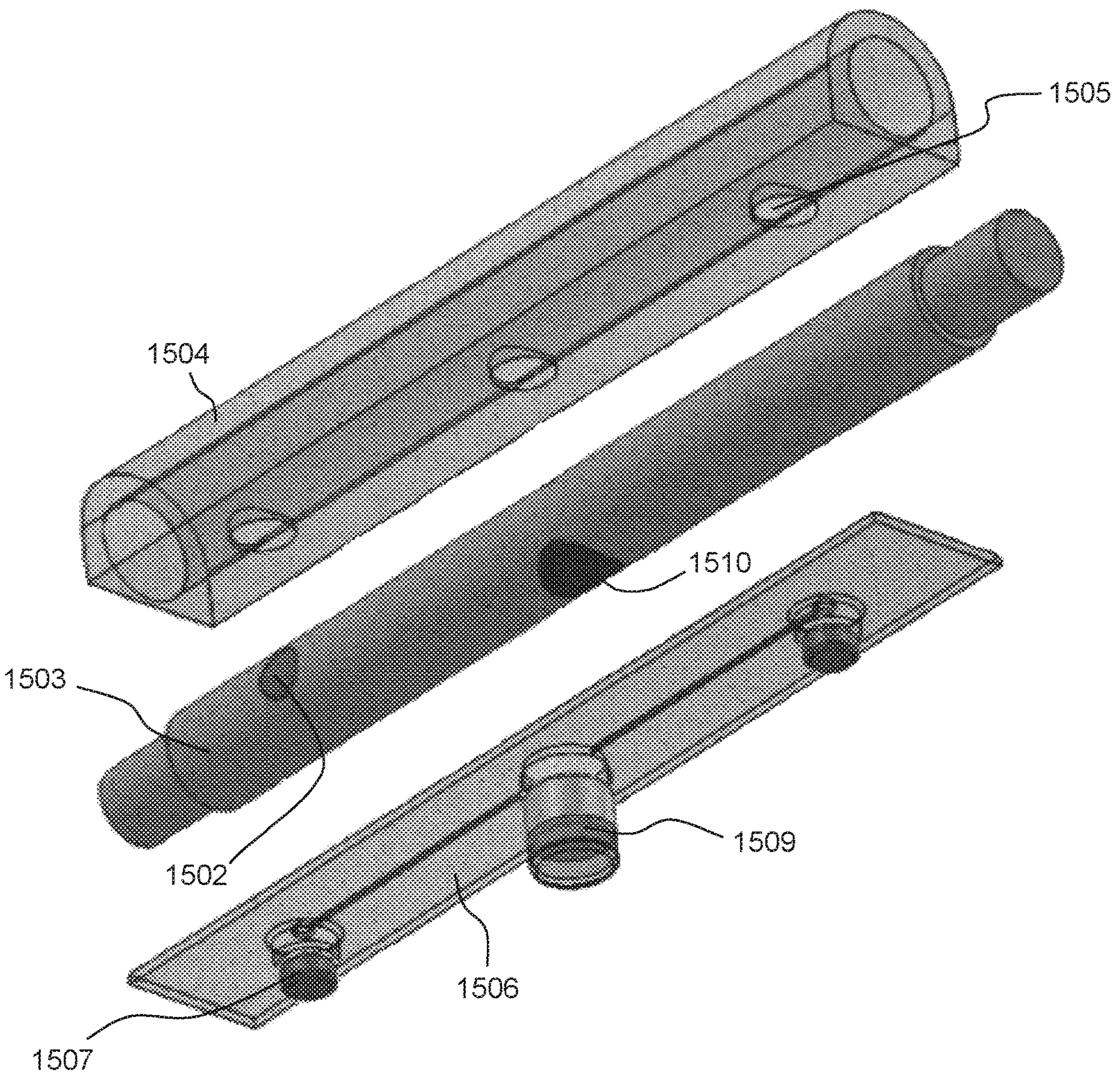

FIG. 15 shows an embodiment of the sample processing system comprising a rotating shaft actuating element with the partially trapped and fixed magnetic elements housed inside the rotating shaft.

FIGS. 16A-16D show different instances of the sample processing sequence as the rotating shaft actuating element rotates over the microfluidic device.

Figure 17A:
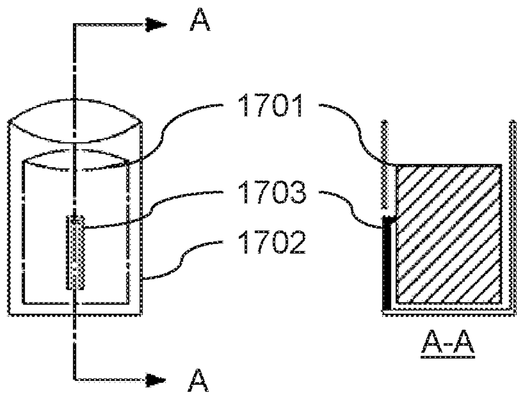
Figure 17B:
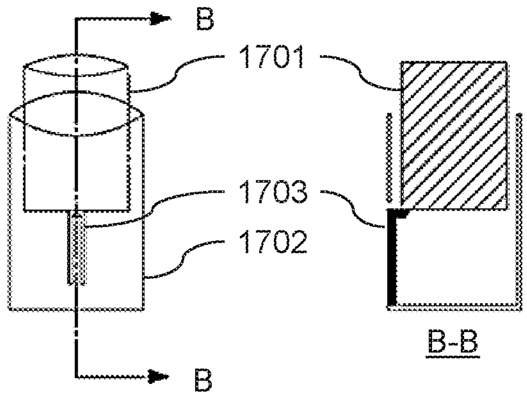
Figure 17C:
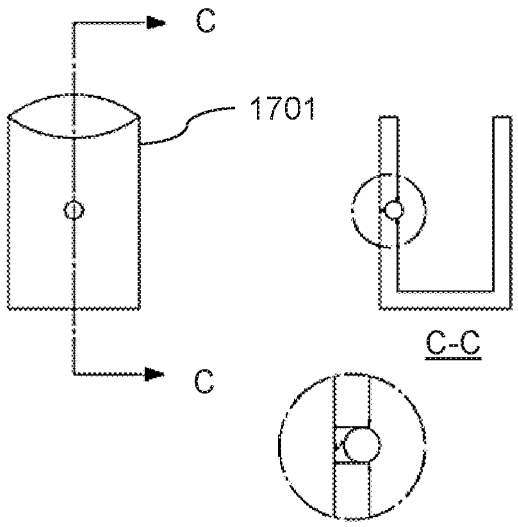

FIGS. 17A-17C show additional non-limiting embodiments to mechanically hold the magnetic plunger element in permanently sealed position even in the absence of the external magnetic field.

Figure 18A:
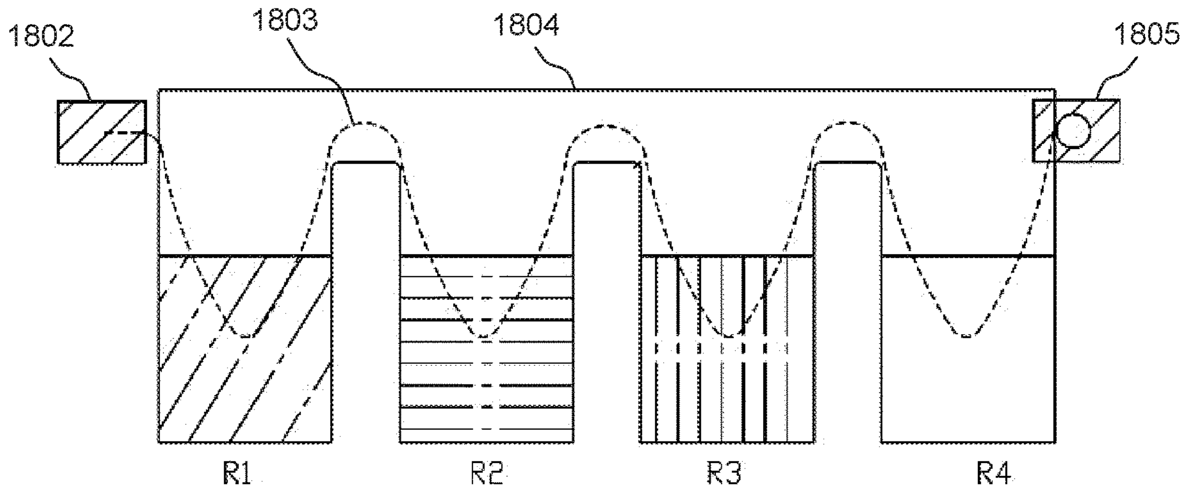
Figure 18B:
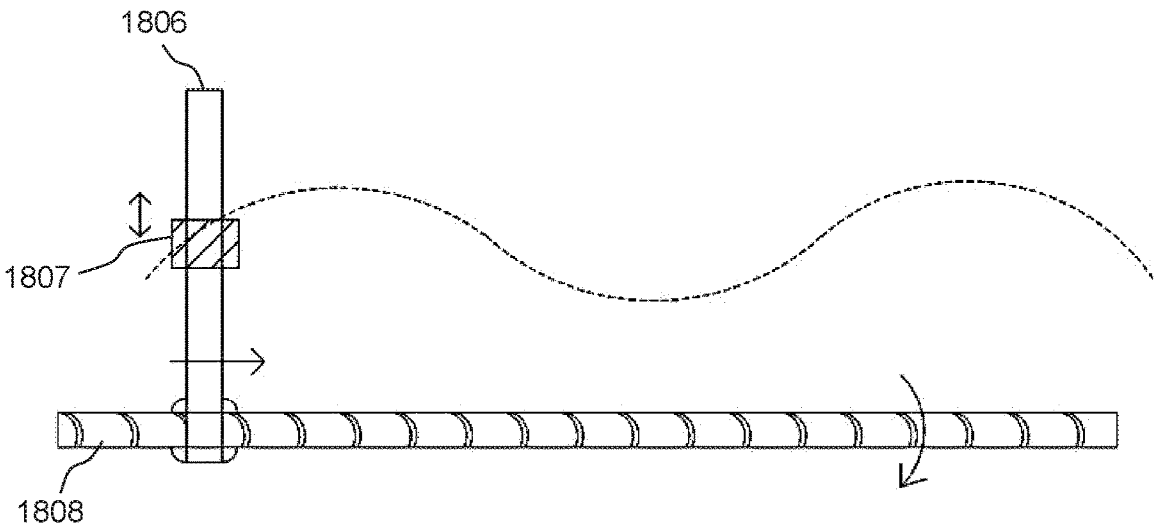

FIGS. 18A-18B show an embodiment of the sample processing system comprising an actuating element comprising a magnet moving on a track.

Figure 19A:
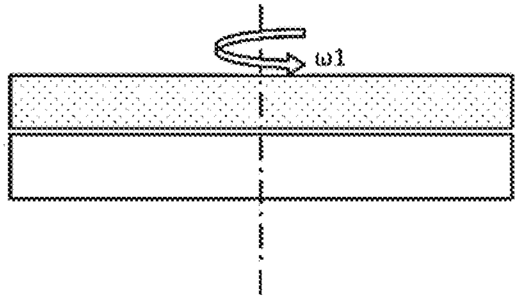
Figure 19B:
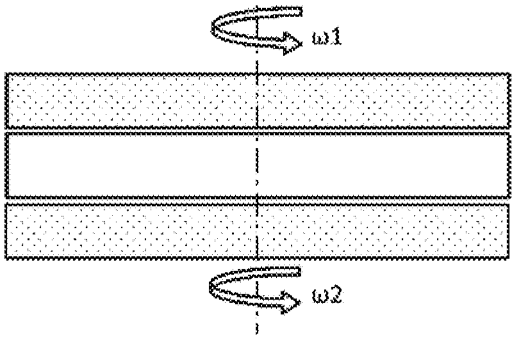
Figure 19C:
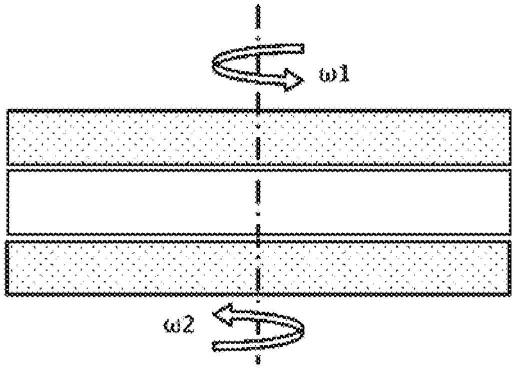

FIGS. 19A-19C show examples of different implementations of rotational actuating elements.

Figure 20A:
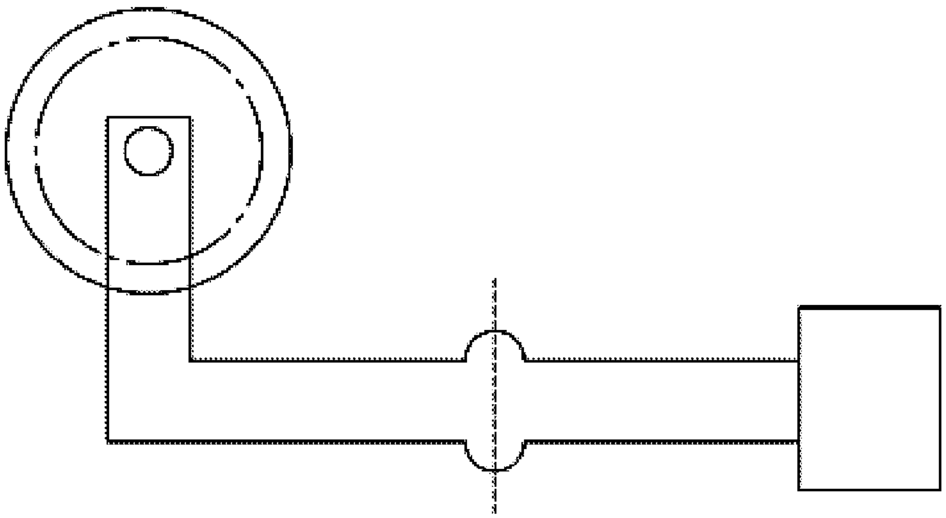
Figure 20B:
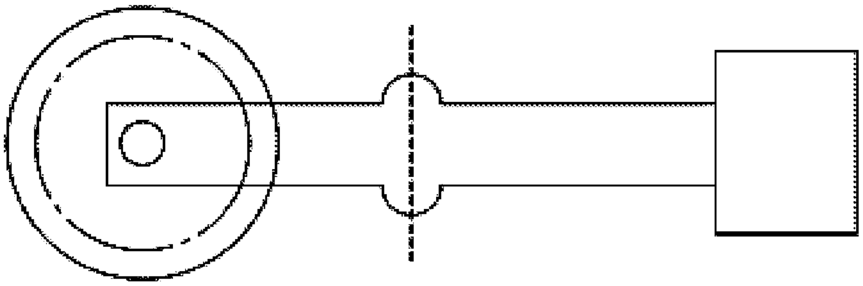
Figure 20C:
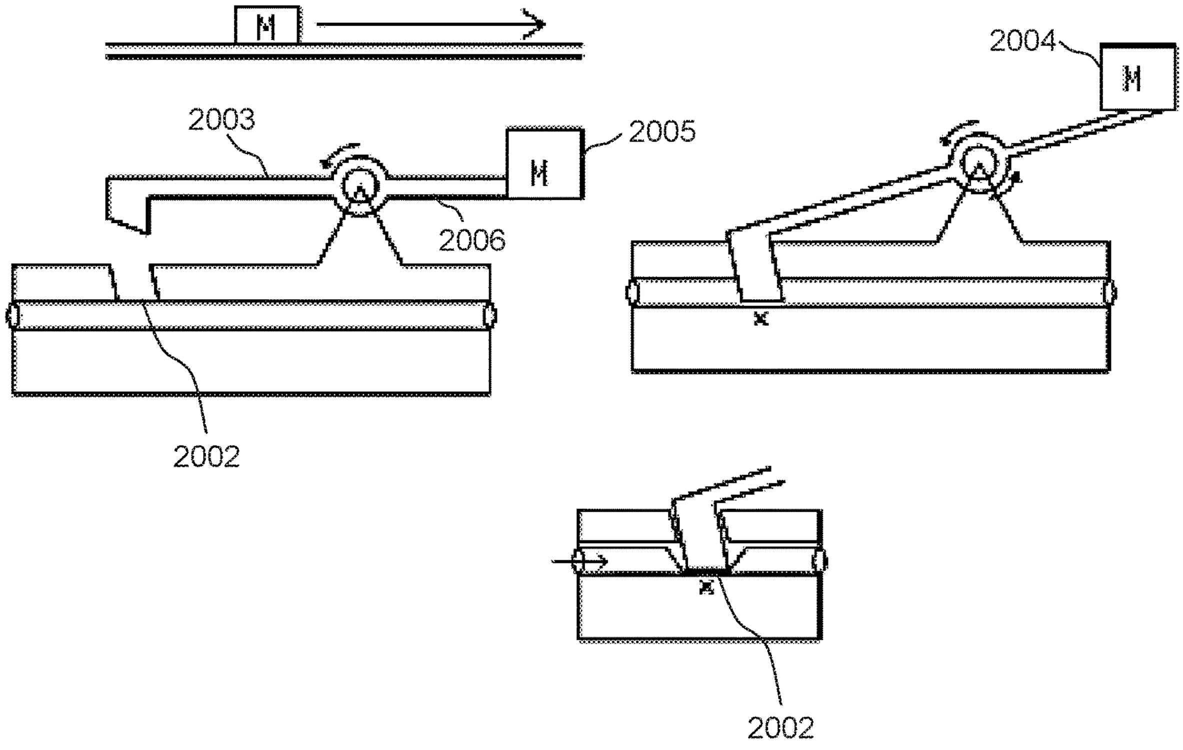

FIGS. 20A-20C generally show an exemplary magnetic pivoting rocker valve with non-magnetic plunger element with FIG. 20A and FIG. 20B depicting top views of two non-limiting embodiments of the pivoting rocker valve geometries, and FIG. 20C depicting an instance where the rocker is activated by a magnetic field and the non-magnetic plunger depresses the diaphragm valve to stop the flow.

Figure 21A:
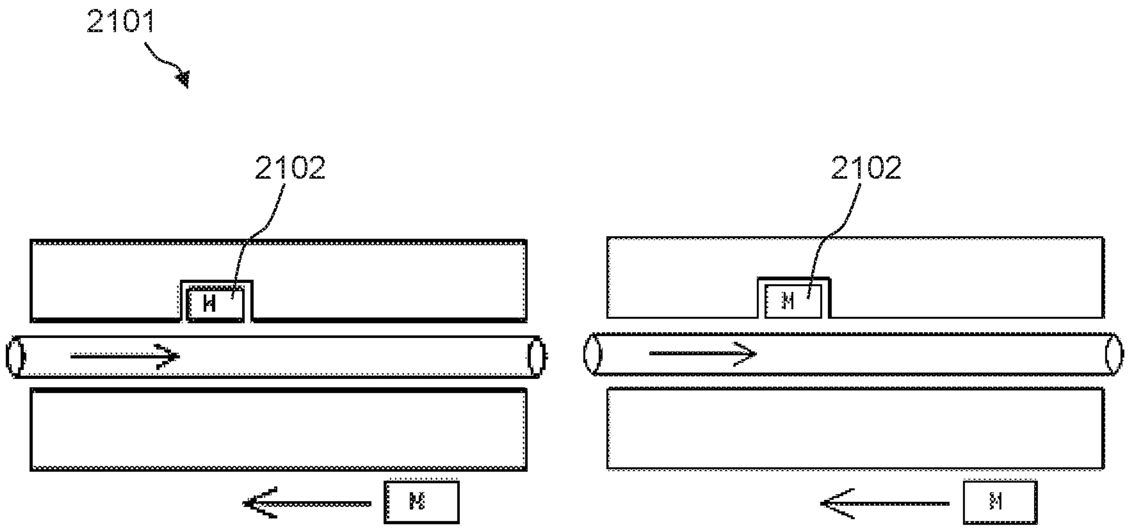
Figure 21B:
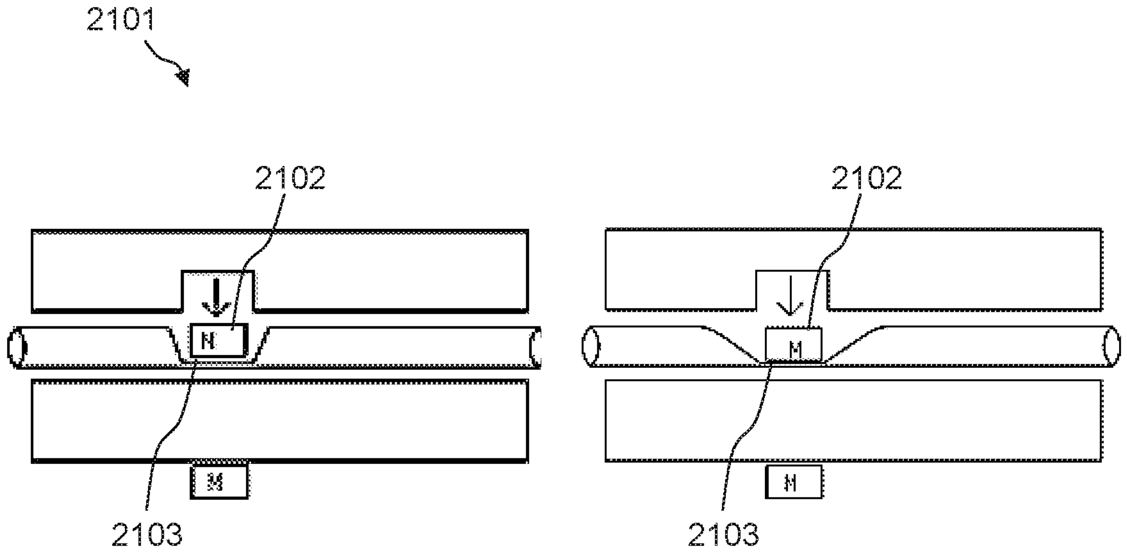

FIGS. 21A-21B generally show a diaphragm or pinch valve with integrated magnetic plunger element with FIG. 21A depicting the valve in its open state when Magnetic field “M” is not in its proximity, and FIG. 21B depicting the valve in its closed state when magnetic field “M” is in its proximity.

Figure 22A:
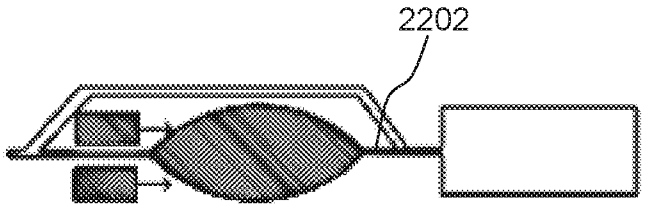
Figure 22B:
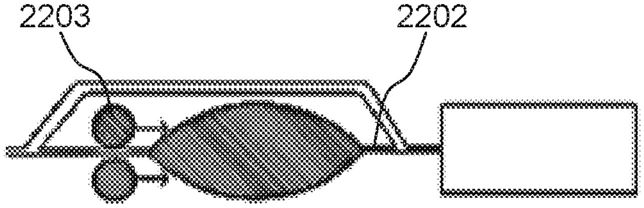
Figure 22C:
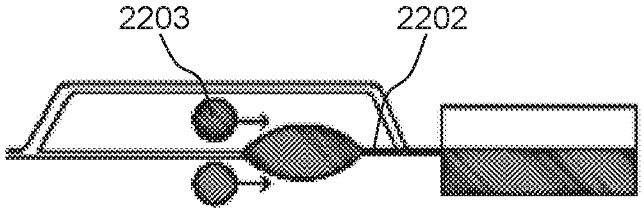
Figure 22D:
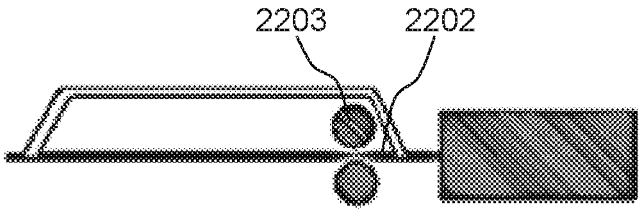

FIGS. 22A-22D generally show an RDU for squeezing the reagent out of the reagent pouch using sliding and rolling motion of the magnetic plunger element with FIG. 22A depicting sliding planar magnetic elements, FIG. 22B depicting rolling cylinder magnetic elements, and FIG. 22C and FIG. 22D depicting emptying of the reagent pouch.

FIGS. 23A-23D show top and section AA views of actuating element; top and section BB views of microfluidic cassette with squeezing element; and instances as the squeezing element is dragged by the linear actuating element, thus displacing fluid to the next reaction chamber, respectively.

Figure 24:
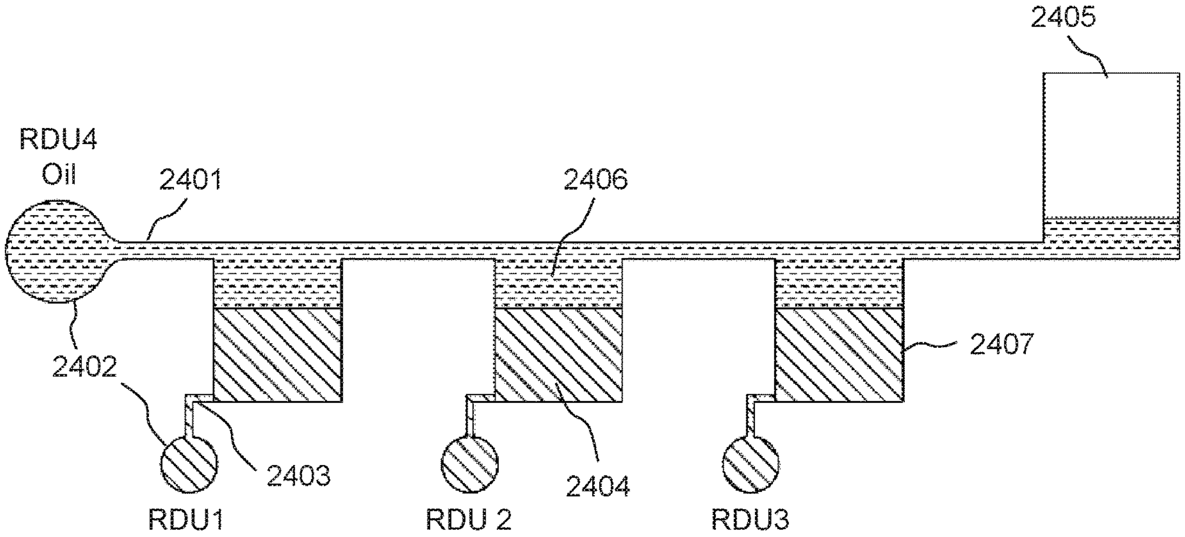

FIG. 24 shows a schematic representation of a fluidic well configuration and the principle for dispensing stored reagents to create an oil-water fluidic circuit.

Figure 25A:
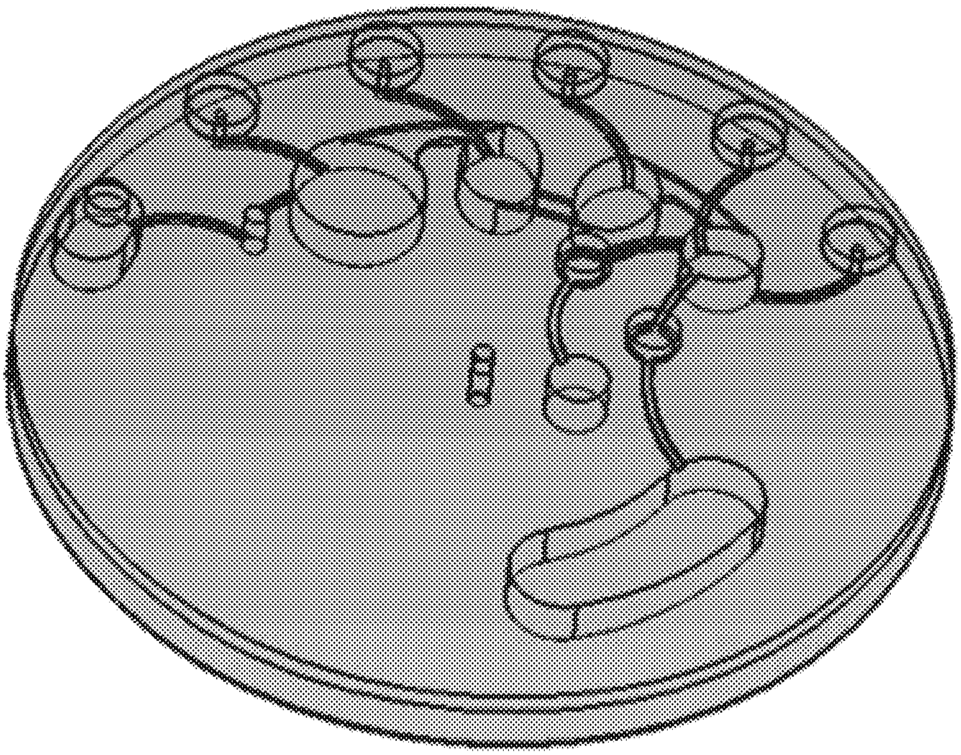
Figure 25B:
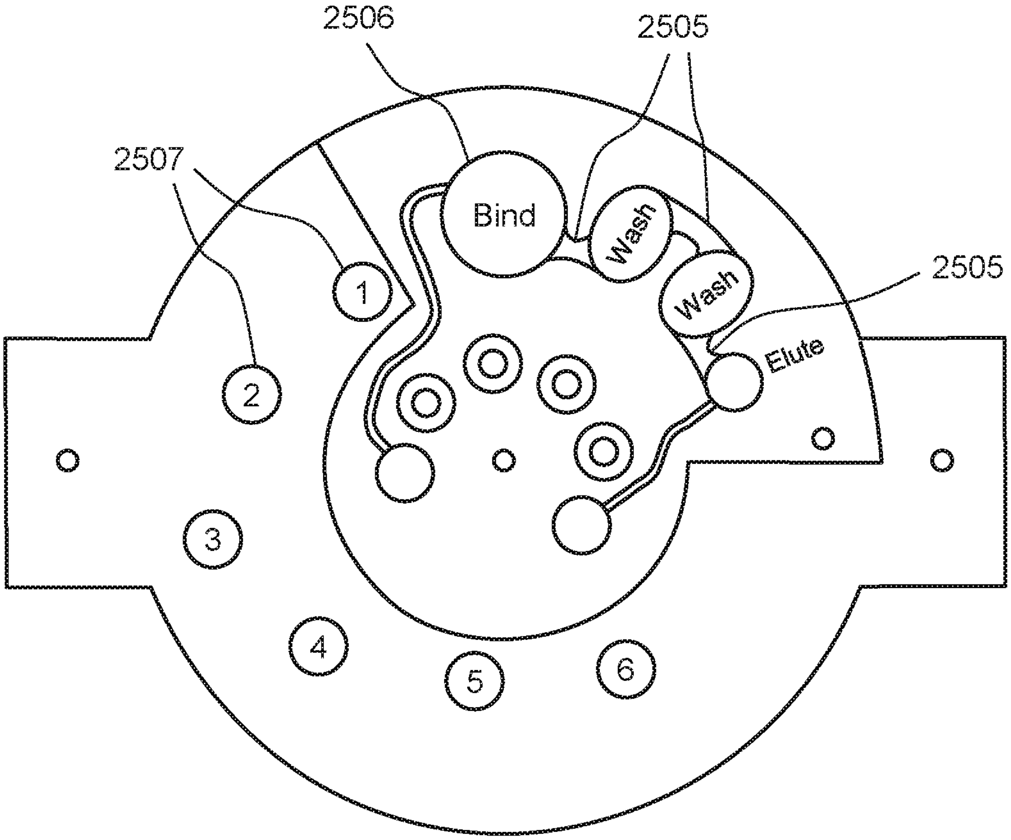
Figure 25C:
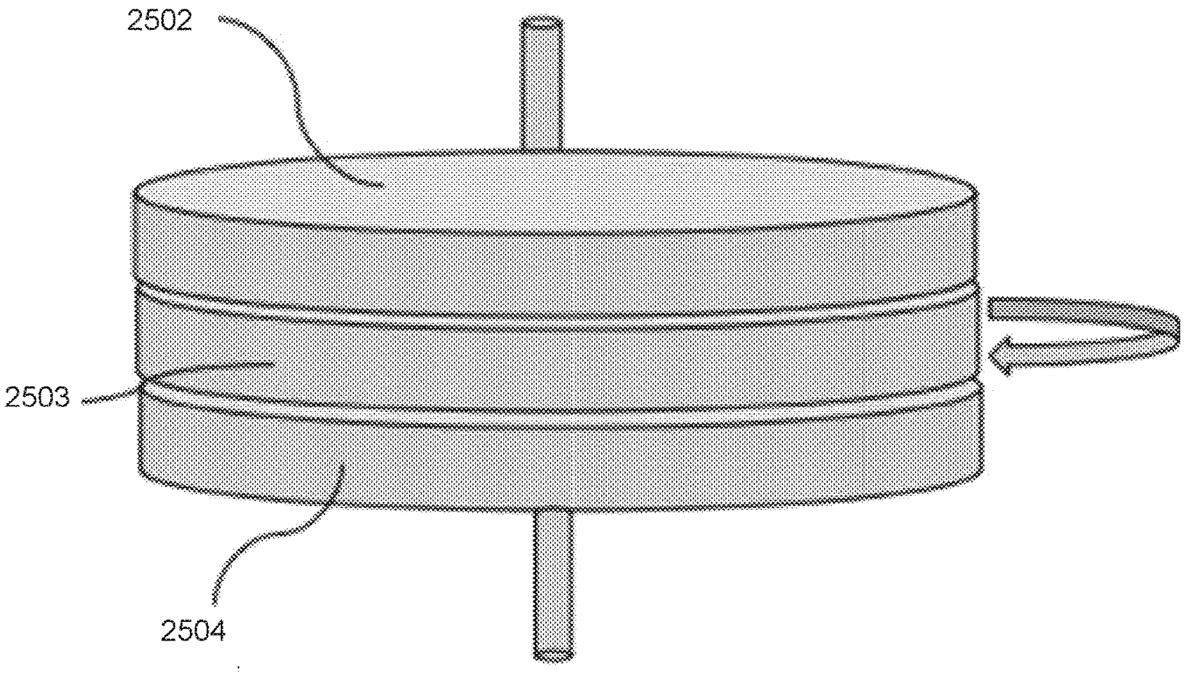

FIGS. 25A-25C generally show exemplary structural elements associated with magnetic bead based sample preparation with FIG. 25A showing a schematic representation of an exemplary microfluidic cartridge for magnetic bead based sample preparation comprising fluidic wells, fluidic conduits, stored liquid reagent reservoirs, and valves, and FIG. 25A and FIG. 25C showing the principle of magnetic bead based sample preparation on an exemplary microfluidic device with integrated top and bottom rotational actuator elements comprising fixed permanent magnets.

FIGS. 26A-26I show different instances of the position of the microfluidic cartridge with respect to the actuator element to illustrate the principle of magnetic bead capture, resuspension and travel between fluidic wells using linear actuation.

FIGS. 27A-27G show a cross-sectional view of a microfluidic device with top and bottom actuator elements to illustrate the principle of magnetic bead based sample preparation on a microfluidic device. The microfluidic device comprises fluidic wells that are connected to each other through an oil phase. The top and bottom actuator elements have electromagnets that can be turned ON or OFF in a predefined sequence. The microfluidic device moves between the two actuator elements.

Figure 28:
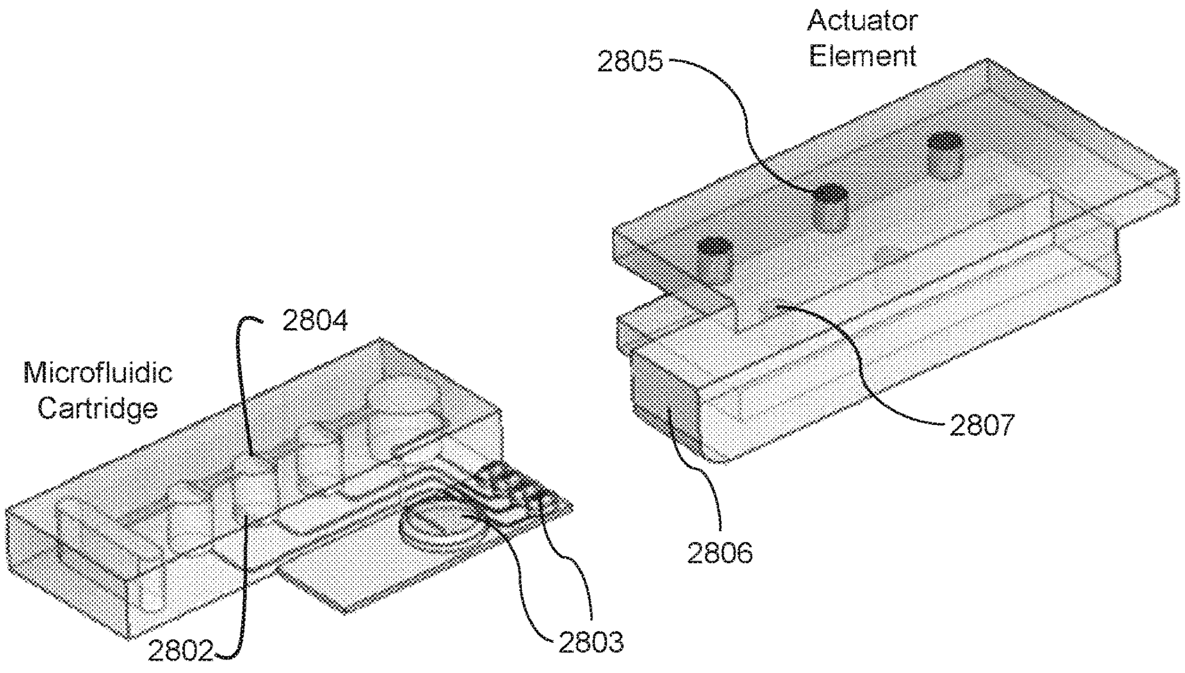

FIG. 28 shows a perspective view of a microfluidic device showing a microfluidic cartridge and actuator element. The microfluidic cartridge slides in between the actuator element.

FIGS. 29A-29E show the principle of using protrusions as baffles in the fluidic well of a microfluidic device to constrain magnetic beads to a well as the magnet continues to move along a path of motion.

Figure 30A:
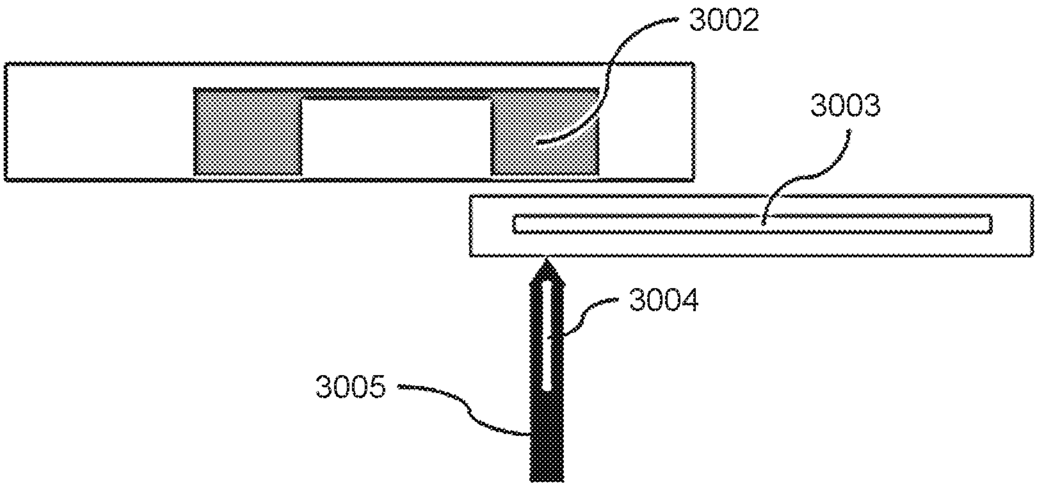
Figure 30B:
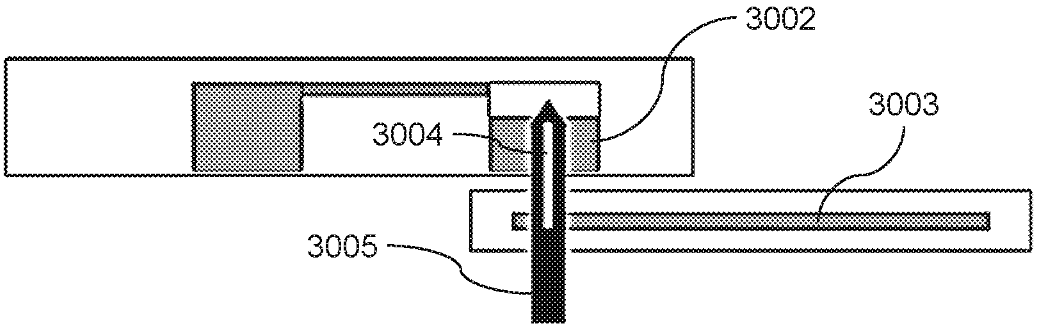

FIGS. 30A-30B show the principle of fluidic transfer on the microfluidic device, from a fluidic well to a lateral flow strip using an actuated lancet.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Sample-to-Answer Microfluidic Devices with Magnetic and Mechanical Actuating Elements Using Linear or Rotational Motion Automation and Methods of Use Thereof The disclosed invention includes methods and integrated devices for sample-to-answer automation using simple, low cost, and low power instrumentation. In one embodiment, a lab-on-chip microfluidic system and associated method that performs multiple steps in a precise sequence with all its automation integrated within a single revolution of a camshaft is provided. In one exemplary embodiment, a fluid handling sequence involving timed reagent delivery is made possible by applying pressure to burst a frangible seal of reagent-filled pouches stored within the cartridge. In one embodiment, thermal management is also possible, for example, during the polymerase chain reaction (PCR), the cam mechanism can be used to actuate contact of a heat sink to control sample temperature and reduce the overall time to result.

Camshafts can run like clockwork, for example, to open and close multiple valves in a precise sequence to preform a task, such as running an engine. When applied to a LOC. the present invention can employ a single camshaft to perform all the actuation and automation steps required to complete a sample-to-answer diagnostic test.

Accordingly, the only actuation required may be to rotate the camshaft through one full revolution. Furthermore, self-contained microfluidic cartridges that comprise of pre-PCR and post-PCR modules on a single platform in one embodiment or several downstream assay processes on it is also possible in accordance with the present invention.

Additionally, the rotating camshaft can be self-powered using a wind-up spring, for example, enabling completely battery-free automation on a LOC device.

Since diagnostic devices in low resource settings generally need to be battery-operated, the present invention allows point-of-care technology to become a step closer to being completely power-free. By integrating a revolving camshaft, point-of-care diagnostics are improved by a number of factors, including reduction of size, power consumption, cost and complexity of the device, to name a few.

A microfluidic cartridge in accordance with one aspect of the present invention can allow integration of pre- and post-PCR processing steps on a single platform using the modularity of microfluidics. Versatility can also be added to the system, since it enables PCR-based DNA amplification and further downstream processing, such as DNA hybridization microarrays, for example, to be integrated on the same chip. Consequently, a single sample can easily be screened for multiple pathogens.

Various aspects of the present invention could also be applicable to a variety of other devices. For example, the present invention can also be used to essentially automate bioassays in a sample-to-answer format on a lab-on-a-chip device. Another possible application could be for protein assays.

Other advantages of the present invention over prior existing technology include: 1) controlling all the actuation steps for fluid management, thermal management, and electrical management on a single camshaft; 2) a simplistic design, low manufacturing cost, low power, and one motor, or a wind-up spring to control the actuation sequence; 3) microfluidic cartridge and camshaft technology that can be used to integrate multiple downstream assay processes on a single self-contained platform; and 4) a self-contained cartridge allows additional modules for downstream processing to be added in a "LEGO" block fashion that can work in tandem with the rotating camshaft actuator to allow precise automation on a device.

Accordingly, a device that consists of a disposable, self-contained microfluidic cartridge featuring reagent filled blister pouches, and a complimentary camshaft that completes all the individual actuation and automation steps for a sample-to-answer sequence in a single revolution is possible using various aspects of the invention. The camshaft, in essence, acts as a mechanical "program" for the entire sample-to-answer automation process. When the camshaft is used in conjunction with a rocker arm, the rocker arm can behave like a plunger for actuation. As the camshaft rotates, the rockers come in contact with the blister pouch and apply the force required to burst the frangible seal. This concept is illustrated in FIG. 1. Using this concept, a single camshaft actuator can perform one more of the following essential tasks: 1) break the frangible seal of an on-chip reagent filled blister pack to release its contents; 2) actuate on-chip diaphragm valves to control the fluid delivery on the microfluidic chip; 3) spatially and temporally release controlled volumes of reagents into a reaction chamber; 4) actuate cooling elements for rapid thermal cycling on the microfluidic chip; 5) actuate permanent magnets to move magnetic beads from one location to another; and 6) actuate electrical contacts for read-out.

Alternative, non-limiting embodiments include: 1) use of a wind-up spring to power the camshaft; 2) use of a camshaft actuator used to automate the operation of a syringe plunger to dispense reagents in an automated sequence; and 3) use of either a horizontal or vertical design.

The features described herein can allow for 3D spatial and temporal control of fluid-handling/management, thermal management, electrical management using a single actuation mechanism. The operational sequence is coded by the arrangement and orientation of the cam lobes.

Other embodiments can include cams without the use of rockers, cam plus pins, gears, clock mechanisms, a wind-up spring, piano hammer action, or any other mechanical variations, which may be capable of automating sample-to-answer sequence.

In one embodiment, a cam mechanism can also be used to actuate functionalized electrodes to move from one sample to another.

Referring now to FIGS. 1A and 1B, side views of an exemplary microfluidic device 101, showing before and after actuation of the rocker arms 109, respectively, are shown. Microfluidic device 101 has a cam 102 with cam shaft 103 and cam lobes 104. A microfluidic cartridge 105 having at least one on-chip burst pouch or blister pouch 106 and reaction chamber 107 is also shown. Burst or blister pouch 107 is filled with fluids, such as reagents, which, upon bursting, dispense the fluid contained therein. These burst or blister pouches 106 can be batch manufactured in large volumes, reducing manufacturing costs. When specifically manufactured for microfluidic applications, the fluids contained range from 15 to 450 μL in volume. Blister pouches 106 generally comprise of a frangible membrane seal that is installed at the outlet port of the pouch. This frangible membrane generally requires deliberate pressure to break its seal and release its contents.

As the cam mechanism 102 is rotated through the cam shaft 103, cam lobes 104 actuate rocker 109, causing it to place pressure in the burst pouch 107, and breaking the frangible membrane.

As can be seen in FIG. 2, multiple cams 202 can be mounted on cam shaft 203. Each cam 202 has cam lobes 204, which provide spatial topography to actuate rocker arms at various times and intervals. As cam shaft 203 rotates, cam lobes 204 push against rocker arms 209, which in turn press against burst or blister pouch 206, releasing its contents. By arranging multiple cams 202 on camshaft 203, spatial and temporal control of the reactions can be controlled. Rocker arm 209 or rocker mechanism acts like a plunger, which pushes down on the blister pouch 206, applying sufficient pressure to cause its frangible membrane seal to rupture. Multiple burst pouches containing varying reagents can be spatially assembled onto the microfluidic cartridges as shown, for example, in FIG. 2.

As the camshaft 203 rotates through one full revolution, the cam lobes 204 lift and engage the rockers 209 thereby spatially and temporally controlling the release of the stored reagents in the blister pouches 206 on the microfluidic cartridge 205. The cam lobes 204 are designed such that the rocker remains in the closed position after rupturing the pouch. This can act as a check valve to ensure that there is no backflow of reagents into a ruptured pouch. The cam lobes 204 can also be used to open and close diaphragm valves along the fluidic channel bringing to realization fluid flow control on that channel.

As generally discussed above, in FIG. 2, multiple cam and rocker mechanisms are shown. Each cam 202 and rocker 209 mechanism corresponds to a specific blister pouch 206. As each cam and rocker mechanism is actuated at appropriate intervals, various reagents are released from the blister pouches through the channels 208 formed on the microfluidic cartridge 205 and into reaction chamber 207 also formed on the microfluidic cartridge 205.

The rotating camshaft can also be self-powered using a wind-up spring mechanism. This enables completely power-free automation on a LOC device where the user can essentially turn a key to get an automated diagnostic result. Since diagnostic devices in low resource settings need to be battery operated, this innovation brings point-of-care technology a step closer to being completely power-free.

Referring now to FIG. 3, a block diagram showing the concept of an exemplary sample-to-answer system 301 for PCR and DNA hybridization is shown. In this example, a plurality of cams 302 are supported by cam shaft 303. Each cam 302 has cam lobes 304, which serve to actuate rockers 309. Microfluidic cartridge 305 is provided with a plurality of burst pouches 306 (in this example, lysis, wash, and elution buffers) various reaction chambers 307, waste chamber 313, and various channels 308 to connect the fluids to its respective chamber 307, 313. Valves 310 are also provided between certain chambers 307, 313 and burst pouches 306 to prevent fluid from flowing backwards and causing contamination.

In this example, a sample is first introduced into the chamber 307 (sample prep), which can contain a vehicle for DNA capture, such as silica beads, FTA paper or magnetic beads, for example. For the sample preparation step, as camshaft 303 rotates, causing the cam lobe 304 to actuate the corresponding rocker to enter a “closed” position, thereby rupturing and releasing a burst pouch containing lysis buffer (in this example) into sample preparation chamber 307. The rotation speed and lobe size of the camshaft can be varied to control the time for each reaction step. Other rockers sequentially enter a closed position, and burst their respective pouches, for example, releasing wash buffers 306 into the sample preparation chamber 307 for the wash steps of DNA purification.

During PCR thermal cycling, a thermal or heat sink 311 can be intermittently actuated by its corresponding rocker to contact the amplification chamber and provide cooling. With PCR thermal cycling, the one of the more time intensive steps is lowering the temperature of the sample. By using the actuated heat sink, which makes contact only during the cooling step, the time taken to complete each PCR cycle can be reduced significantly. Accordingly, complete automation of the sample-to-answer sequence can be realized with a single camshaft rotation as shown in this example.

Heat sink 311 can also be provided on the microfluidic cartridge, for example, during the PCR cycle, to make intermittent contact with a reaction chamber 307 in a precise sequence that is designated by the cam mechanism and/or rotation speed. A first order heat and mass transfer calculation estimated an approximate 7 times drop in the time taken for cooling the sample from 95 degrees to 65 degrees. This time reduction was realized with a 1" by 1" by 0.5" aluminum block heat sink in an ambient air temperature of 25 degrees. For example, if cooling time without a heat sink takes 30 seconds/cycle and there were 25 cycles; the time saved would be 12.5 minutes for the complete PCR process. This provides notable advantages in thermal management during fluid handing, for example. Heater 312 is also shown in this figure on the microfluidic cartridge 305.

Referring now to FIG. 4, a plan view of an exemplary sample-to-answer microfluidic device using an integrated revolving port design is shown. As depicted in FIG. 4, the exemplary microfluidic device 401 integrates camshaft 403 as part of the microfluidic cartridge 405. In this embodiment, camshaft 403 of the cartridge is coupled to the actuating mechanisms during rotation of camshaft 403. With this system, specific camshafts can be designed and built for a variety of different assays. Another alternative approach is to build a standard camshaft module mount and develop a unique camshaft module for different assays.

The exemplary system of FIG. 4 uses precisely cut slots 414 positioned at predetermined angular positions along the shaft 403. When rotated to the pre-determined angular position, the slots 414 form a flow channel 408 between the reagent-filled pouches 406 and the reaction chamber 407. Flow pressure can be developed by pushing down on the reagent-filled pouches 406. The revolving port also makes for a simple valve.

The microfluidic cartridge can also be designed without the PCR amplification chamber. In this case, the cartridge could contain a DNA hybridization chamber for detection of an analyte without amplifying a target. This design may be especially appealing for sample-to-answer high throughput screening through DNA hybridization arrays with a powerful single molecule detector such as a Total Internal Reflection Flourescence (TIRF) microscope or a Single Photon Avalanche Diode (SPAD) array detector.

In other embodiments, the present invention uses magnetic actuation combined with mechanical automation to complete a sample-to-answer sequence on a microfluidic device. The actuation methods and various embodiments of apparatuses described herein can be used to dispense a reagent into the fluidic device and along a fluid conduit, open/close valves, cause agitation and mixing inside a fluidic chip, turn ON/OFF an electrical circuit or create an electrical connection inside a fluidic chamber.

The fluidic device consists of reagent pouches that dispense the reagents needed for biological sample processing on the microfluidic device. Pouch reagents include but are not limited to buffers, salts, acids, bases, labels, tags, markers, water, alcohols, solvents, waxes, oils, gases, gels, for example. When sufficient pressure is applied on the pouch, it will burst, thereby dispensing the contents of the pouch into fluid conduits that lead to their intended reaction chamber. The pouches are designed with frangible seals aligned with the inlet of the fluidic conduit so that when the pouch bursts, its contents are forced to enter the fluid conduit leading to reaction chambers.

Magnets can attract magnetic elements, which could be either another magnet, an electromagnet or a ferromagnetic material. The invention below describes a novel method and apparatus to apply the burst pressure to empty the reagent pouches. The apparatus is called the Reagent Dispensing Unit (RDU). The RDUs are comprised of reagent pouches containing stored reagents, and an integrated magnetic element that can be either a permanent magnet or a ferromagnetic element. When this magnetic element is attracted by a magnetic field that is brought into its proximity, it will move towards this magnetic field and act like a plunger that depresses the reagent pouch and, through one of the non-limiting embodiments described herein, bursts the pouch, leading to the expulsion of its contents into the fluidic chip. The plunger's motion is constrained so it can efficiently empty the blister; this is achieved by designing guides for it to move in.

FIGS. 5A-5B depict a cross-sectional view of the RDU on a microfluidic device. In this example, the RDU is bonded to the microfluidic device 511 using adhesive 512 such that it forms a hermetic seal with the microfluidic device. The RDU has an integrated magnetic element plunger 503 on top of the reagent pouch 505. The reagent pouch contains stored reagent 514 and is sealed by a frangible sealing layer 506. The magnetic element plunger is held in place by encasing it inside a sheath 502 such that its motion is constrained.

In some embodiments, the reagent-filled pouch contains a small bead 504 (see FIG. 5A) or sharp object such that under the influence of a magnetic field 509, the bead or sharp object 504 will facilitate the breaking of the frangible seal. This object is made from a magnetic material which when attracted to a magnetic field will rupture the frangible seal. In another embodiment as seen in FIG. 5B, a sharp object 513 fixed to the fluidic device inlet will rupture the frangible seal of the reagent pouch as it pushes on this element.

In some embodiments, seen in FIGS. 5A-5B, a trap 510 is present on the microfluidic device 511 such that a loose magnetic material can be permanently deployed and held in place under the reagent pouch, to keep the pouch depressed. Such a system works like a one-time actuated valve that keeps the reagent pouch depressed thereby preventing any back flow from the reaction chamber into the reagent pouch.

In another embodiment seen in FIGS. 6A-6C, the frangible seal is designed so it ruptures at a certain pressure. The magnetic element plunger is attracted by the magnetic field, providing the necessary burst pressure and deformation that breaks the frangible seal. The magnetic element plunger situated above the reagent pouch is simultaneously attracted towards this same magnetic field, and deforms the ruptured pouch, thereby forcing the stored reagent to flow into the reaction chamber 608 through the fluid conduit 607.

In applications where a large sample volume needs to undergo mixing, lysing or homogenizing, the fluid can be broken up into separate smaller chambers that are fluidically connected to each other, with each chamber containing its own trapped permanent magnet. FIG. 7A depicts a rotating shaft 705 comprising permanent magnets arranged axially and radially with alternating poles 706 on the periphery of the rotating shaft, and FIG. 7B depicts a multi-chamber fluidic mixing system where the fluidic chambers 704 are connected to each other using valves 702 such that they can handle a range of sample volumes. A permanent magnet 703 is present in each chamber, and its direction of motion is restricted along a path perpendicular to the axis of the rotating shaft.

In another embodiment seen in FIG. 8, the reagent pouch is designed in such a way as to allow for the point of rupture to occur at a precise location. This is accomplished by designing the reagent pouch so that it contains a magnetic element 804 that is constrained to a particular area 805 of the reagent pouch, and which therefore directly overlays the frangible portion 806 of the seal 802.

While the method for sample processing described herein can perform multiple processes with a single actuation motion, for the purpose of describing the actuation control on a microfluidic device, a simplified example of a single linear actuating element controlling multiple sample processing steps is described herein where three sample processing steps namely: 1) bursting and releasing stored reagents from reagent pouches; 2) moving magnetic beads between chambers; and 3) opening and closing fluidic valves.

Other processes that can be integrated into the same actuation control element include but are not limited to opening/closing a electrical connection inside a fluidic chamber, pressing a push button switch for on/off control to an electrical circuit, puncturing a vacutainer, opening/closing a vent hole, actuating heating element or heat sink. A huge advantage of such a system is that additional steps can be added with minimal increase in system complexity. Referring to FIGS. 9A, 9B and 9C, top views and section AA of an exemplary microfluidic device for sample processing 901 comprising a linear actuation element 903 comprising fixed magnetic elements for magnetic bead displacement 904, fixed magnetic elements for fluidic valve actuation 905 and fixed magnetic elements for reagent pouch bursting 902; and a microfluidic cassette 908 comprising stored reagent pouches with integrated magnetic plunger elements 907, reagent chambers 906 for sample processing, magnetic pivoting rocker valve featuring non-magnetic plunger 909 for controlling the movement of magnetic beads through a valve, and magnetically controlled valves comprised of magnetic plungers 910. The actuation element 903 is in close proximity to the microfluidic cassette 908 and slides relative to it. In this exemplary embodiment the actuation element 903 slides under the microfluidic cassette 908, however in other embodiments the microfluidic device 901 is designed such that the actuating element 903 slides on top.

Additionally the actuation element can comprise of a top element and a bottom element moving together in the same direction or independently in different directions such that they their motion results in multiple actuation steps for sample processing, occurring in a predefined sequence.

The sample processing sequence is depicted at different instances as the actuating element slides under the microfluidic cassette in FIGS. 10A, 10B, 10C, 10D, 10E and 10F. Some methods that can be used to cause the sliding motion include motor, wind-up spring, hand crank, manual pushing, linear solenoid actuator. The fixed magnetic elements 1004, 1005 and 1002 on the sliding actuating element 1003 are shaped such that, the actuation state (on/off, open/close, up/down) on the fluidic element on the microfluidic cassette is controlled by the shape of the fixed magnetic element on the sliding actuating element. At instance one FIG. 10A, a fixed magnet on the sliding actuating element overlaps with the magnetic pivoting rocker valve featuring non-magnetic plunger 1009 and closes the valve. As the actuating element keeps sliding, at instance two in FIG. 10B, a fixed magnetic element depresses the stored reagent pouch causing it to release its contents into the reaction chamber. Simultaneously, the magnetic pivoting rocker valve featuring non-magnetic plunger 1009 remains closed, thereby trapping the stored reagents in the reaction chamber. As the actuating element continues to slide at instance three in FIG. 10C, a second fixed magnetic element overlaps a second stored reagent pouch, thereby causing it to burst and release its contents into the same reaction chamber. The magnetic rocker valve featuring non-magnetic plunger 1009 has remained closed. At the fourth instance in FIG. 10D, a magnetic element overlaps the reaction chamber containing the magnetic beads and starts to draw them through the fluid conduit and into the second reaction chamber. At the same instance, a third reagent pouch is burst, and its contents are released into the second reaction chamber. As the actuating element keeps sliding at instance five in FIG. 10E, the fixed magnetic element is now no longer overlapping the magnetic rocker valve featuring non magnetic plunger 1009 and that valve returns to its "off" state thereby opening the fluid conduit such that the magnetic beads are able to pass into the second reaction chamber. Finally, at instance six, in FIG. 10F, the magnetic beads are transferred to the second reaction chamber, while fixed magnetic elements overlap and close the valves into and exiting the second chamber such that the magnetic beads are trapped in the second reaction chamber.

This embodiment describes is an example of how multiple sample processing steps can be controlled using a single actuating element. It is preferred that the system employs permanent magnets such as neodymium magnets for completing the actuating steps such that the resulting apparatus would utilize minimal power for actuation control. However, it is also possible to use a combination of electromagnets and permanent magnets to automate the sample processing steps.

For additional control, in some embodiments, multiple actuating elements can be utilized, that are actuated at different velocities and in different directions. Some non-limiting embodiments of linear actuating elements are shown in FIGS. 11A-11F.

Another embodiment of the actuating element is described in FIGS. 12A, 12B, 12C and 12D. This would comprise a combination of fixed and partially trapped magnetic elements 1212, contained in their own trap 1211, such that their motion is restricted to one axis/direction. The partially trapped magnetic elements could function to irreversibly attach and get trapped in the magnetic trap 510 illustrated in FIG. 5A, even as the sliding actuating element continues to move forward. This embodiment is useful when there is a desire to permanently close a valve, such as keeping a reagent pouch depressed so as to avoid backflow during subsequent sample processing steps.

Figure 12A:
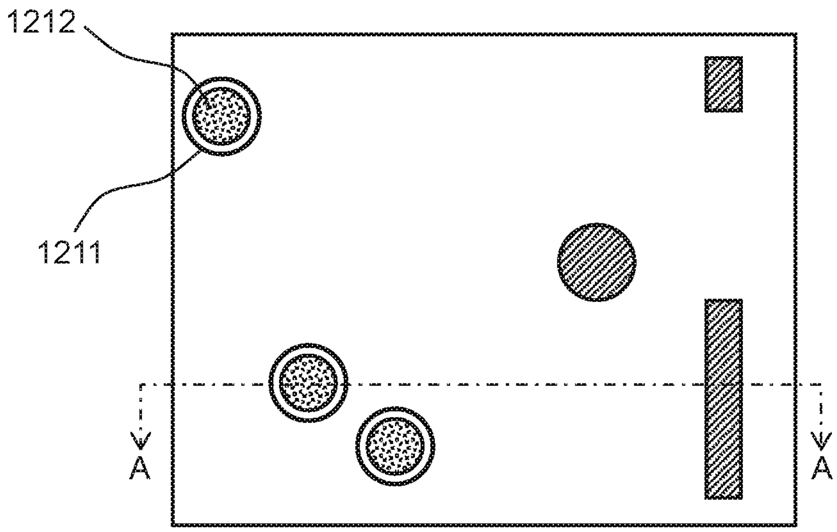
Figure 12B:
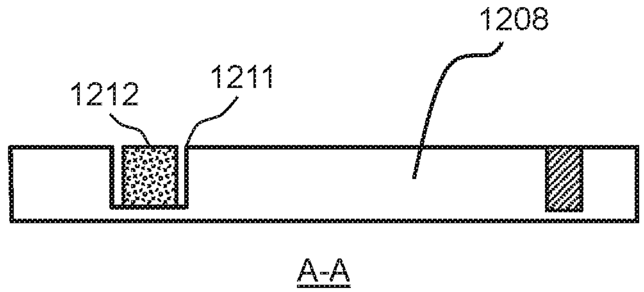
Figure 12C:
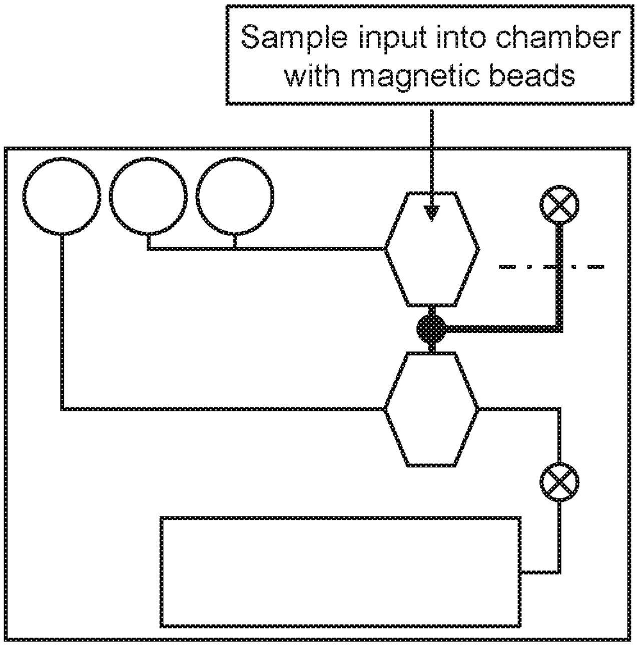
Figure 12D:
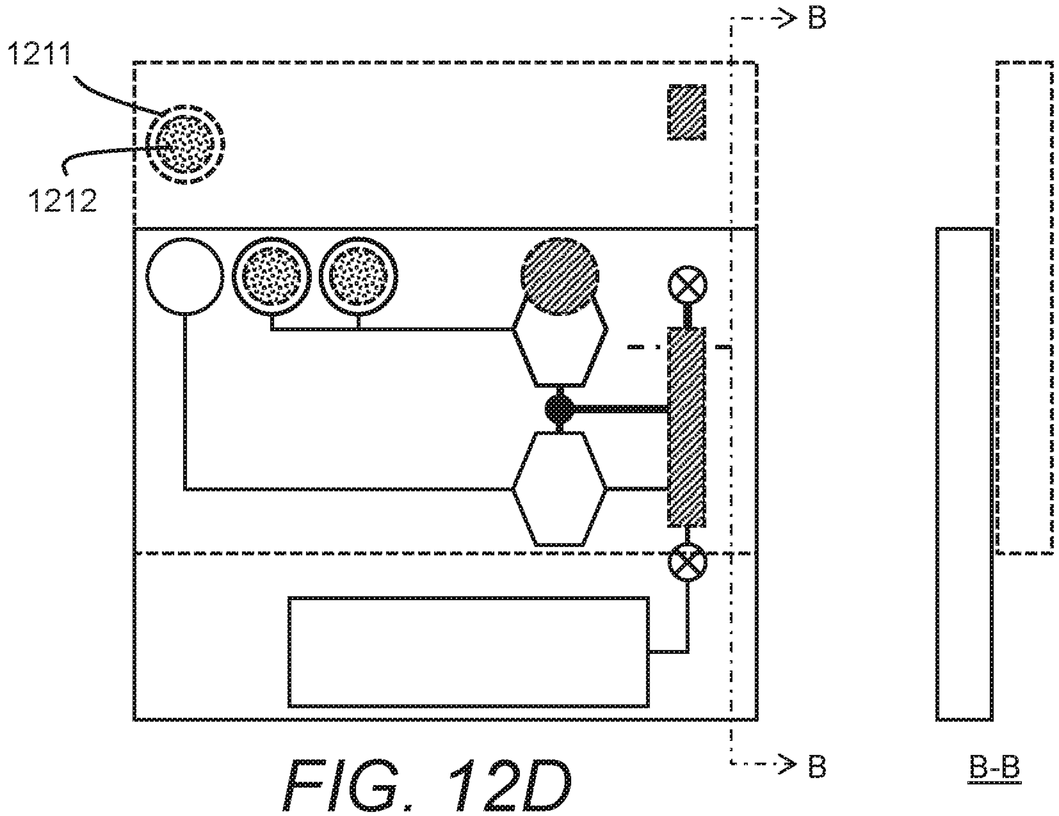

FIG. 12B is a section AA of the actuating element showing the partially trapped magnetic element 1212 contained in a blind hole such that its motion is restricted to a direction perpendicular to surface of the microfluidic cassette 1208. FIG. 12D illustrates a particular instance as the actuating element slides, where the partially trapped magnets have left the actuating element and permanently attached themselves to the magnetic trap 110 situated under the reagent pouch. In this embodiment the reagent pouches are permanently depressed by the partially trapped magnetic element 1212 even as the sliding actuating element continues to move forward.

Another exemplary method to dispense a reagent into a fluidic chamber shown in FIG. 13A and FIG. 13B, where the magnetic, plunger element 1303 is integrated into the reaction chamber 1304 and the reagent pouch 1302 is aligned with it. When the magnetic plunger element is attracted by a magnetic field 1305 it breaks the frangible seal of the reagent pouch, enters into the reagent pouch and displaces the reagents 1306 into the reaction chamber.

In another embodiment, seen in FIGS. 14A-14C, the reaction chamber is located far from the fluidic inlet, and the magnetic plunger element is located between the inlet and the reagent pouch. The magnetic element has a notch 1403 on it that acts as a guide and restricts the flow of fluid to the reaction chamber through the guide notch. The guide notch is designed such that when the magnetic element plunger reaches its top most position, the entry into the reaction chamber through the fluidic conduit is shut as seen in FIG. 14C. A ratchet element 1402 is present inside the fluidic device such that it holds the magnetic element plunger permanently in a sealed position.

Another embodiment of the sample processing system is an actuating element with the partially trapped magnetic element 1502 housed inside a rotating shaft 1503 and shown FIG. 15. This rotating shaft is assembled in a sleeve 1504 which have the magnet traps 1505. The sleeve assembles with the micro fluidic device 1506, which contains the RDU's 1507, mixing chamber 1508 and the mixing chamber magnet 1509. There is a fixed permanent magnets 1510 arranged so that its opposite poles are aligned with the periphery of the rotating shaft; this magnet causes the mixing chamber magnet to get attracted and repelled at a high frequency as the shaft rotates.

Figure 16A:
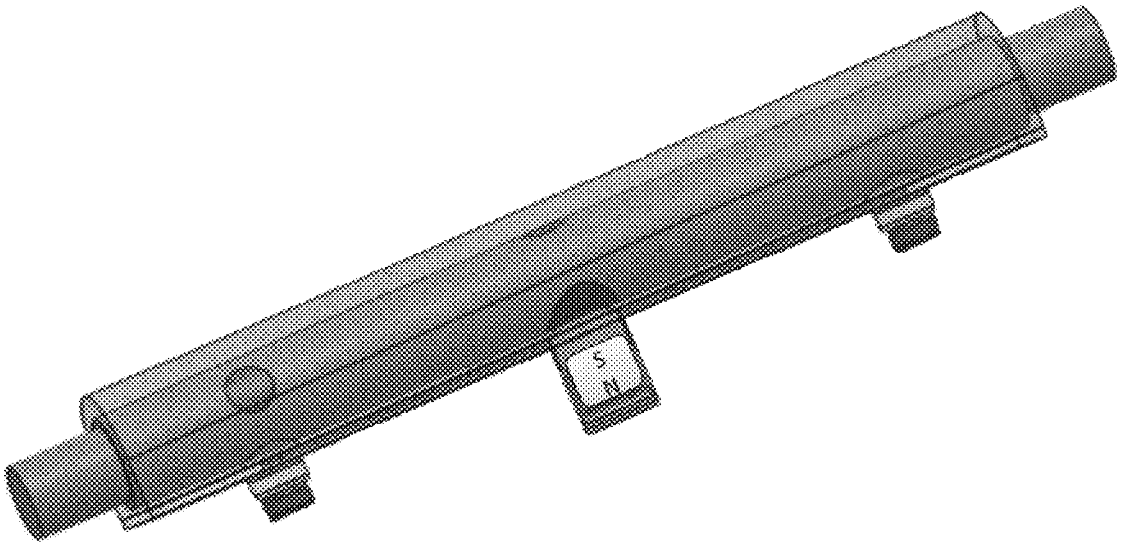
Figure 16B:
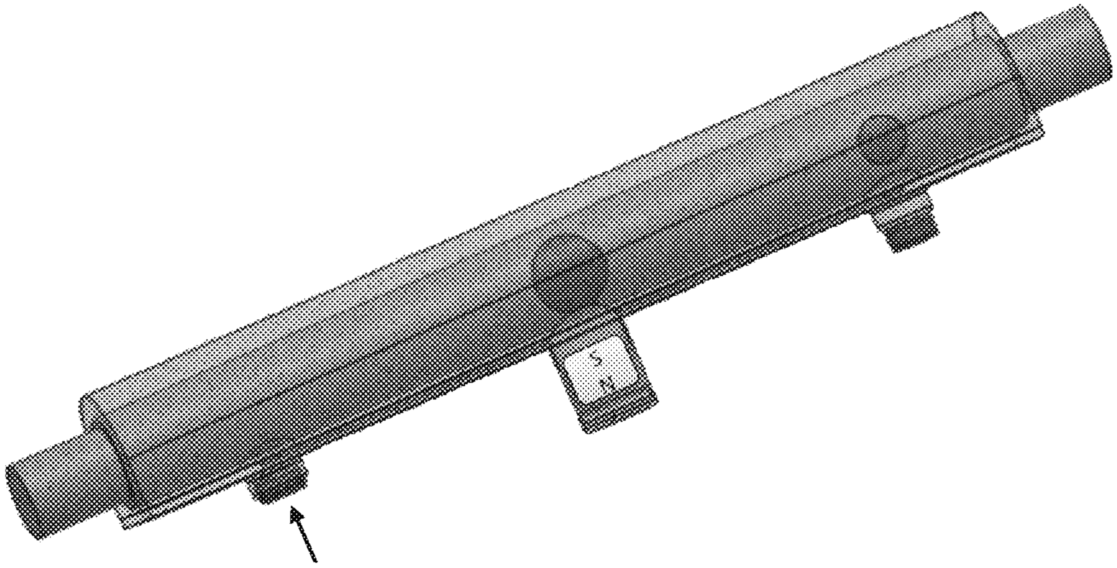
Figure 16C:
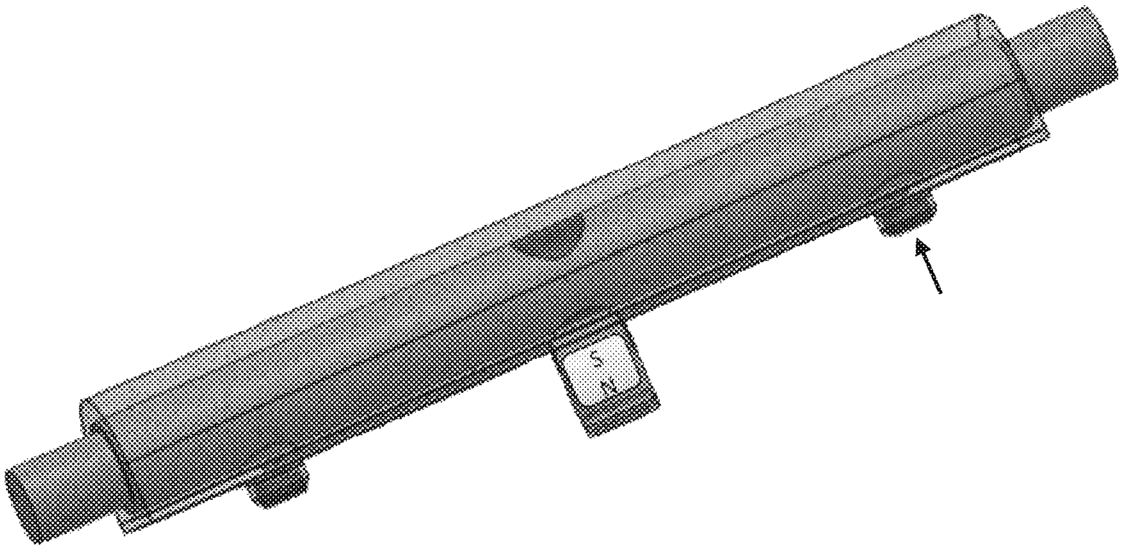

FIG. 16A depicts an instance when the rotating shaft is assembled into the sleeve. None of the partially trapped magnets are aligned with the RDUs. The instance depicted in FIG. 16B shows when the rotating shaft that has rotated through an angle so that the first RDU aligns with the first partially trapped magnetic element. At this instance this partially trapped magnet moves out of the rotating shaft and enters the magnet trap in the sleeve. This also initiates the attraction of the magnetic element on the first RDU, which ruptures the frangible seal on the pouch and displaces its constituent reagent into the lysing chamber. FIG. 16C depicts the next instance when the shaft has rotated through an angle so the second partially trapped magnet aligns with the second RDU. This causes the RDU to empty its constituents into the mixing chamber also.

Figure 16D:
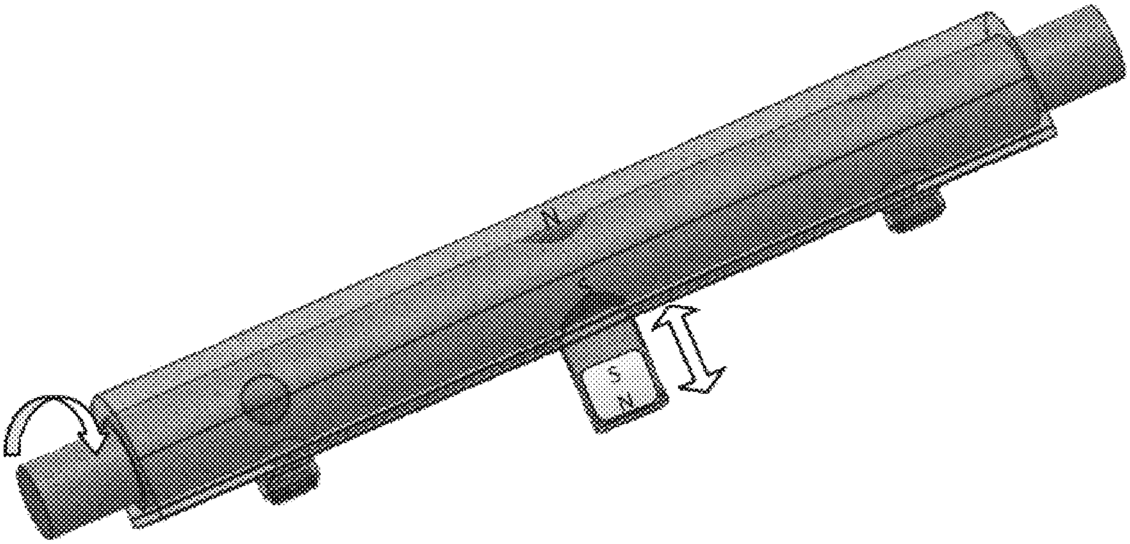

After the stored reagents have been dispensed, the rotating shaft rotates at a high RPM as depicted in FIG. 16D to enable mixing. This causes the fixed permanent magnet in the shaft to present alternating poles to the mixing magnet at a high frequency. This high frequency attraction and repulsion causes mixing in the mixing chamber.

Referring to FIGS. 17A-17C, another embodiment of the system, which mechanically ensures that the magnetic plunger element cannot return to its original position after actuation is shown. This embodiment is advantageous in cases where an element like a reagent pouch or valve needs to be permanently depressed throughout the sample processing sequence. FIG. 17A depicts the instance where the magnet is in its initial position. The sleeve containing the magnets comprises of at-least one cantilevered ratchet element molded into its wall. The magnet deflects the ratchet in this position. When the magnet is displaced as depicted in FIG. 17B, the ratchet will retract making it impossible for the magnet to move downwards back to its initial position. FIG. 17C depicts another embodiment of this mechanism with a spring-loaded ball. The ball works similar to the ratchet, it is deflected by the side of the magnet while a magnetic force pulls the magnet towards it; however the edge of the magnet will not be able to depress the spring loaded ball after the removal of the magnetic field.

Referring to FIGS. 18A-18B, a unique embodiment of the sample processing system that employs an actuating element comprising a magnet 1802 moving on a track 1803 is shown. The magnet attracts the magnetic beads onto which the biomolecules are bound. As the magnet moves along the track it drags the magnetic beads in the microfluidic chip 1804 as shown in FIG. 18A. The tracks path is through the reagent chambers R1 to R4 in FIG. 18A. A moving the magnetic beads through all the reagent chambers at the appropriate time. Finally, the magnet moves through the end of the trap, which is the ball trap 1805.

FIG. 18B describes a mechanism for the motion of the magnet on a track. The magnetic element is mounted on a carriage 1807, which is free to move along the sliding rail 1806. The entire sliding rail traverses the length of the microfluidic device by moving along a linear screw 1808. In another embodiment of this system, the linear screw is replaced by a rack and pinion mechanism. As the sliding rail traverses the length of the chip, the magnet on the carriage rides the track.

In another embodiment, one or more magnets may be arranged on the track to perform multiple sample processing steps either sequentially or in parallel. While in this embodiment the magnet is shown to slide on the track, it is also possible to fix the magnets on the tracked path of a moving conveyor belt.

The embodiments above describe the sample processing automation using linear actuation elements, however rotational elements would confer their own advantages. FIGS. 19A, 19B, 19C show embodiments of a microfluidic devices employing rotational actuating elements for automating the sample processing sequence.

Additionally, some embodiments of the sample-processing device can employ a combination of one or more rotational and linear actuating elements depending on the design and sample processing requirements to gain control over the x, y, z and r axes.

Embodiments of magnetic plunger element valves for controlling fluid flow in an exemplary microfluidic device are described below. In this embodiment an exemplary magnetic pivoting rocker valve with non-magnetic plunger element is described. FIGS. 20A and 20B show top views of two non-limiting embodiments of the pivoting rocker valve geometries that can be used as a valve in a microfluidic device. In such a valve a rocker 2003 with a magnetic element 2005 pivots (or rotates) about it axis 2006. When an external magnetic field 2004 is brought into proximity it will attract the magnetic element on the rocker. This causes the plunger 2002 to push down on the diaphragm valve thereby stopping the flow of fluid through the channel. FIG. 20C shows the instance where the rocker is activated by a magnetic field and the non-magnetic plunger depresses the diaphragm valve to stop the flow. When the magnetic field is removed the rocker returns to its original position and flow in the channel can resume.

Referring to FIGS. 21A-21B, a diaphragm or pinch valve can be depressed on the microfluidic device using a magnetic plunger element as seen in 2101. FIG. 21A describes the instance where the flow channel is open. The magnetic plunger element 2102 is seen over the diaphragm 2103. When an external magnetic field is brought into proximity of the magnetic plunger element, it attracts the plunger towards it thereby depressing the diaphragm valve and stopping flow in the channel. This is depicted in FIG. 21B.

Application of a permanent magnet fixed to a rotating shaft enables mixing, homogenizing and/or mechanical disruption of biological samples including but not limited to cells and viruses. In an exemplary embodiment, permanent magnets are affixed axially and radially on the periphery of a rotating shaft in such a way as to exhibit alternating polarity along the length of the rotating shaft. The fluidic device or container contains a second permanent magnet material trapped inside it such that its motion is grossly restricted to one axis. When the rotating shaft is placed in proximity to a fluidic device or container, the permanent magnetic material inside the container experiences alternating attraction and repulsion forces, resulting in reciprocating and shearing motion inside the fluidic device or container. This effect can be used to perform mixing, homogenizing and lysing of biological samples including cells and viruses. In this embodiment the fluidic container would contain at-least one permanent magnet inside it, whose motion is restricted in a direction perpendicular to the axis of rotation of the shaft. The frequency of the alternating field is determined by the rotational speed of the shaft and spatial distribution of the permanent magnet poles in the radial direction.

In another embodiment, the magnet inside the fluidic device/container might be restricted to reciprocal motion in a different direction, such as parallel to the axis of the rotating shaft. In addition, it may be advantageous to forego the above described magnet motion restriction altogether. In some embodiments, particles (such as beads made of glass, silica, polymer, metal or a combination thereof) can be placed inside the container—these particles would assist in mechanically disrupting biological samples (such as cells and viruses) inside the fluidic container. In one embodiment, the permanent magnet may be directly in contact with the fluids in the fluidic chamber, in another embodiment the permanent magnet may be in close proximity to the fluidic chamber such as separated by an impermeable layer in a separate chamber that is close enough to be capable of causing vibration and vortex forces in the fluidic chamber. The advantages of such a system over using electromagnets with alternating/switching polarities include that it requires only one actuator rotating element (motor shaft) to cause lysis, homogenizing and mixing effects in multiple fluidic chambers or containers spaced along the length of the rotating shaft.

In another embodiment of the system, squeezing the reagent out of the reagent pouch in the RDU may be ideal. This is particularly advantageous in cases where additional control of the flow rate of reagents is needed. FIGS. 22A-22D is a cross section view of such an embodiment. In this embodiment the magnetic plunger element 2203 is constrained such that it can only move in the direction required to squeeze the pouch, break the frangible seal 2202 and dispense reagents through the fluid conduit and into the microfluidic device. In some embodiments FIG. 22A the magnetic plunger elements may have a flat planar bottom surface. In other embodiments, the magnetic plunger element may be a cylinder that results in a rolling effect. FIGS. 22B, 22C, and 22D show the magnetic plunger element 2203 in the RDU being actuated by a partially trapped cylinder magnet in the actuating element of the microfluidic device, resulting in a squeezing of the reagent pouch such that the frangible seal is ruptured, leading to steady reagent flow into the chamber on the microfluidic device.

Figure 23A:
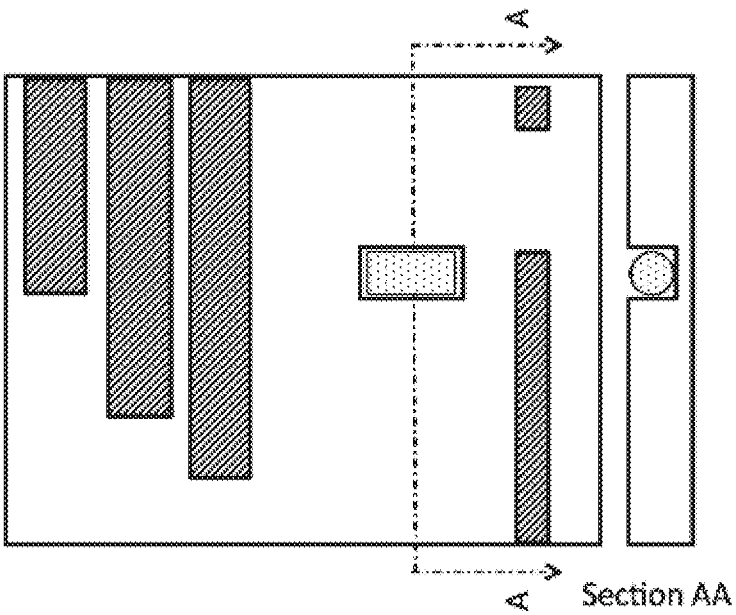
Figure 23B:
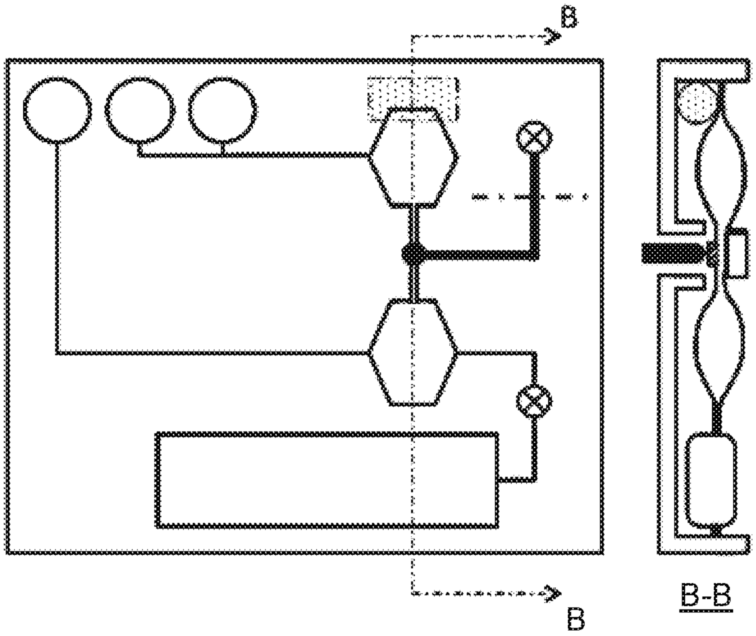
Figure 23C:
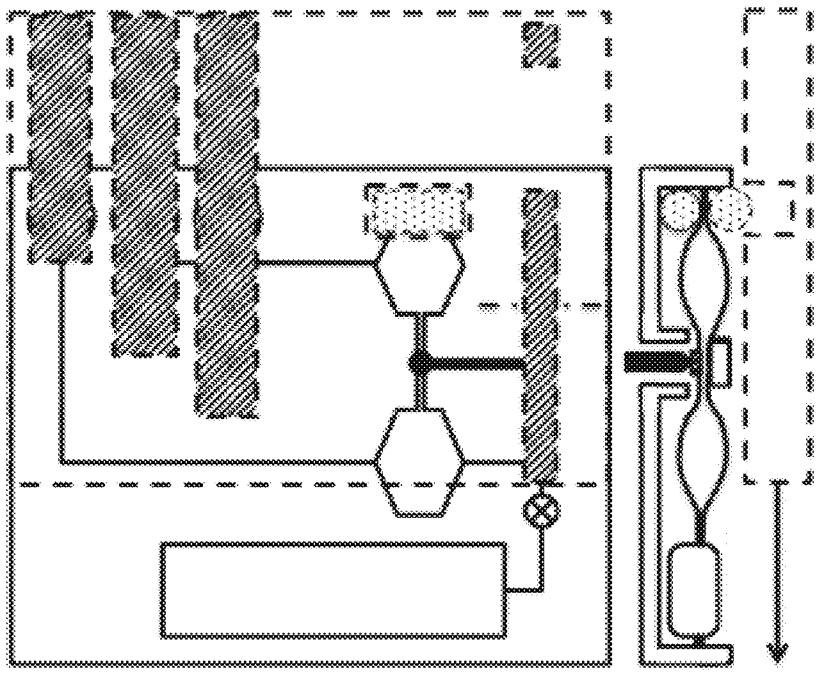
Figure 23D:
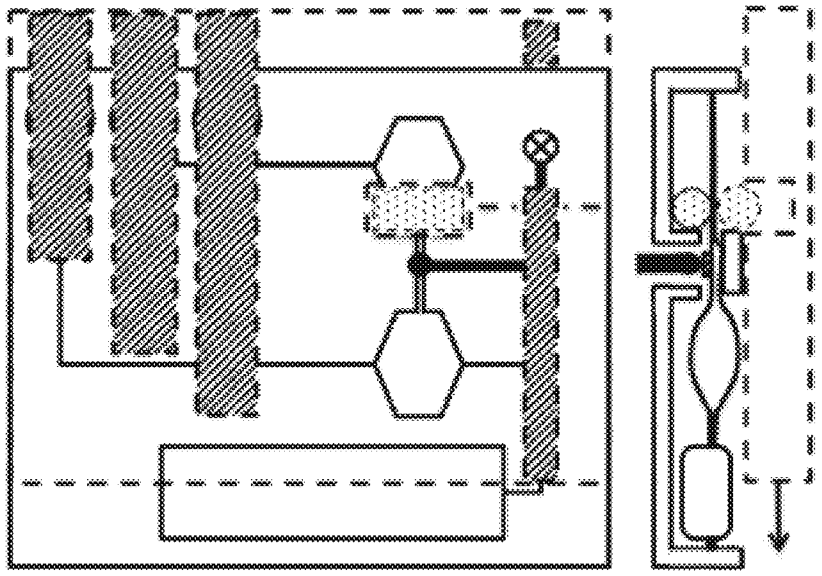

Fluid can be moved from one reaction chamber in the microfluidic device to another using air filled pouches to push the fluid. In some embodiments when the reaction chambers in the microfluidic are designed such that they can be compressed, the embodiment shown in FIGS. 22A-22D can be used to move fluids from one reaction chamber to another. While it is possible to burst air filled pouches to push reagents out of chambers, in the same way that the reagents are filled, in some embodiments, the squeezing mechanism described in FIGS. 22A-22D can be used to do this step. FIGS. 23A-23D illustrate the above microfluidic device where the reaction chamber are designed such that they can be squeezed and compressed to a flat and planar state. FIG. 23A shows the top and section AA views of the actuating element containing a partially fixed magnetic roller for squeezing reagents out of the pouches. FIG. 23B shows top and section BB views of a reaction pouch with partially trapped magnet roller in proximity with the reaction chamber. As the linear actuating element moves, FIGS. 23C and 23D show the reaction chamber being squeezed by the magnetic rolling elements to dispense its fluid into the next chamber.

Another aspect of the present invention is a fluidic device for sample preparation for nucleic acid amplification tests. The fluidic device comprises two or more fluidic wells that are configured such that they are connected to each other via a primary fluidic conduit. The fluidic wells can be separately filled with liquid reagents through inlet fluidic conduits. In some aspects of the invention, the inlet fluidic conduits are connected to external openings in the fluidic device to enable the fluidic wells to be filled by pipetting or injecting reagents into the well through the inlet fluidic conduit.

For point of care settings, self-contained systems are advantageous since they do not require any complex, user driven pipetting or injection steps. Accordingly, in other aspects of the invention, reagents may be stored on the fluidic device in reagent pouches. When sufficient pressure is applied on the pouch it bursts, thereby dispensing the contents of the pouch into the fluid conduits that lead to their intended reaction chamber. The pouches are designed with frangible seals aligned with the inlet fluidic conduits such that when the pouch bursts, its contents are forced to enter the inlet fluid conduit and fill the fluidic well. Pouch reagents include but are not limited to buffers, salts, acids, bases, labels, tags, markers, water, alcohols, solvents, waxes, oils, gases, gels, and the like.

Each fluidic well volume is so designed such that it may be only partially filled with miscible liquid reagents so as to not allow the miscible liquids in each fluidic well to overflow and mix with each other through the primary fluidic conduit connecting each fluidic well. The surfaces of each fluidic well may comprise a hydrophilic and a hydrophobic surface or may be modified to be hydrophilic or hydrophobic (e.g, via hydrophilic or hydrophobic coating). Hydrophilic modification may be done to increase wettability and better enable liquid reagents to fill the well evenly while hydrophobic modification may be done to decrease wettability and facilitate the smooth transfer of solid particles between fluid filled fluidic wells.

Reagent pouches containing immiscible liquids such as mineral oil are connected to the primary fluidic conduit connecting each well such that upon actuation: 1) the contents of the reagent pouches containing the immiscible liquids get released to form immiscible oil phases over the liquids filled in the fluidic wells; and 2) all the miscible liquids in the fluidic wells are connected in a sequence to form a fluidic circuit, but separated from each other by an oil phase to avoid mixing with each other. The primary fluidic conduit exits into a reservoir to collect excess oil. The miscible reagents can be dispensed sequentially or in parallel into their respective wells, depending on the assay requirements. The immiscible liquid is dispensed after the reagent wells have been filled such that the empty volume in the primary fluidic conduit and the partially filled wells is completely filled with an immiscible oil phase to create a fluidic circuit.

While it is possible to pre-fill the fluidic wells with buffers separated by an oil phase, and then seal and store the cartridge for later use, some reagents (including but not limited to enzymes, oligos, dNTPs and buffers) are not stable in their liquid form at room temperature or for long periods of time, and thus need to be stored in lyophilized format and hydrated before use. Additionally, introducing the sample into such a pre-filled system presents a challenge. The disclosed invention provides a method and device to address the challenges related to sample introduction, reagent delivery, and assay automation for sample processing on a microfluidic device.

FIG. 24 depicts a block diagram schematic of the fluidic chamber configuration. The fluidic wells 2407 are connected to one or more RDUs 2402 containing miscible reagents (RDU1, RDU2 and RDU3) through an inlet fluidic conduit 2403 entering at the bottom of each fluidic well. The fluidic well volumes are designed such they are only partially filled by the miscible liquid reagents 2404 entering through the inlet fluidic conduits. Upon completion of the filling of the fluidic wells, RDU4 containing an immiscible liquid is actuated and its contents are dispensed into the fluidic device through the primary fluidic conduit 2401. A non-limiting example of an immiscible liquid is oil 2406, which fills the empty volume in the primary fluidic conduit and fluidic wells, thereby creating a fluidic pathway and at the same time forming a barrier between the miscible liquids in the fluidic wells so as to prevent them from mixing together. The immiscible liquid that is used to close the fluidic circuit is selected such that it has minimal or no reactivity with the miscible liquid reagents. The excess oil collects in a reservoir 2405. The oil also functions as a vapor barrier to prevent evaporation during nucleic acid amplification or other assay steps that may require heating.

The fluidic circuit created has advantages for automating sample preparation steps using magnetic beads for solid phase capture since the beads can be moved with a magnet through the oil phase into the fluidic wells containing different sample processing reagents. As an example, the wells may be filled with lysis, binding, wash, and elution buffers for nucleic acid purification, and separated by an oil phase. The magnetic beads may be moved into the different wells in a predefined sequence, through the oil phase, so as to complete the sample preparation steps for nucleic acid purification. This enables easy automation of sample processing steps on a microfluidic device.

In another embodiment, the fluidic wells and primary fluidic conduit on the microfluidic cartridge may be prefilled completely with oil. During use of the microfluidic device, the miscible liquid reagents that are stored in the reagent pouches are dispensed into the desired fluidic wells on the microfluidic cartridge thereby displacing the excess oil which is then collected in an excess oil reservoir 105.

Magnetic beads are frequently used in biological sample preparation for extracting, isolating and purifying nucleic acids, proteins, biomolecules and cells in biological samples. The major advantage of magnetic bead based solid phase extraction is the ease of automation since there is no need for centrifugation or vacuum manifolds. Under optimized conditions, DNA selectively binds to the functionalized surface of magnetic beads, while other contaminants stay in solution. The beads can be captured in place using an external magnetic field and the contaminants can be removed by pipetting out the solution with the contaminants, and washing the beads in wash buffers. The Purified DNA can then be eluted in a desired volume and used directly in molecular biology applications.

The disclosed invention describes a method and device for magnetic bead based sample preparation comprising a fluidic chip comprising a series of fluidic wells with miscible liquid reagents for sample preparation, separated by an immiscible oil phase; and top and bottom actuator elements with one or more spatially oriented permanent magnets fixed to them, depending on the number of fluidic wells and resuspension steps required. The permanent magnets on the top and bottom actuators are arranged such that, in a single continuous motion they can: 1) Resuspend the magnetic beads; and 2: Move the magnetic beads between fluidic wells in a predefined sequence.

The fluidic wells are so designed such that they have periodically spaced top and bottom baffles or obstructions that act as a physical barrier to constrain the beads in a fixed position either on the top or bottom of the well and prevent the beads from moving further in the direction of the permanent magnet on the actuator element. In some embodiments, the walls of the fluidic well may function as a baffle or physical barrier to constrain the motion of the beads to a predefined path. When a magnet on the opposite face of the well comes in proximity to the beads, they are attracted towards the magnet, causing them to resuspend through the liquid reagents or buffers that are present in the fluidic well. The immiscible oil phase works to complete a fluidic path so the beads can be resuspended and moved through different reagents in a series of wells through an oil filled primary fluidic conduit, so as to complete a sample-to-answer sequence. The invention is advantageous since it is able to only employ a single continuous motion and permanent magnets for completing a sample-to-answer sequence, thus reducing the complexity and power burden for sample-to-answer automation.

In some embodiments, a servomotor or stepper motor may be used to move the actuator elements or the microfluidic device. In some embodiments, a mechanical wind-up spring mechanism may be used for generating the motion. The mechanical wind-up spring has an added advantage of being completely power-free with no need for electrical energy to automate the sequence. In some embodiments, the actuator elements may be manually driven, by the user's finger.

Referring to FIG. 25A, a schematic representation of an exemplary microfluidic cartridge for magnetic bead based sample preparation is shown comprising fluidic wells, fluidic conduits, stored liquid reagent reservoirs and valves. The microfluidic cartridge is sandwiched between top and bottom actuator elements that comprise permanent magnets and projections or protrusions. The permanent magnets and protrusions are spatially arranged such that they perform different steps of an assay automation sequence with precise timing, depending on their position and speed of the actuator elements as the microfluidic cartridge rotates in close proximity to the actuator elements. Assay steps that may be performed include dispensing stored reagents into fluidic wells, opening and closing valves to control the direction of fluid flow, opening and closing vents, capturing, resuspending, and moving magnetic beads between wells. As seen in FIG. 25B and FIG. 25C, the oil filled fluidic conduits 2505 through which the magnetic beads are able to sequentially enter multiple reagent filled fluidic wells 2506 on the microfluidic device, are alternately offset such that the walls of the wells act as physical barriers to constrain the beads to a desired well. The permanent magnets on the rotational actuator elements are also offset so as to capture and resuspend the beads in the multiple reagent filled fluidic wells along the rotational path.

As an example, an isothermal Nucleic Acid Amplification Test (NAAT) such as Loop Mediated Isothermal Amplification (LAMP) may be performed on the microfluidic device using an integrated heater. The fluidic wells may be filled with buffers for binding, washing and elution. ChargeSwitch magnetic beads may be used for nucleic acid extraction and purification. Lyophilized reagents for LAMP may be stored on the microfluidic cartridge in a fluidic well that is designated for amplification. Magnetic beads may be stored on the microfluidic cartridge in the well designated for binding.

As the microfluidic cartridge rotates between the top and bottom actuator elements, the sequence of operation for performing a NAAT may be as follows: 1) Lysate is introduced into the first "bind" well by opening a valve; 2) Binding, Wash 1, Wash 2, and Elution buffers are dispensed into the first, second, third and fourth well respectively on the microfluidic cartridge; 3) Mineral oil is filled such that it overlays the reagents in the wells and forms a continuous fluidic circuit through which the magnetic beads can travel between wells; 4) The magnetic beads are sequentially captured, resuspended and moved into the four wells through the top oil conduit; 5) By opening a valve, the eluted DNA from the elution well may be metered into a fifth LAMP amplification well containing lyophilized master mix, thereby hydrating the reagents; and 6) A heater on one of the actuator elements comes in contact with the LAMP amplification chamber to heat it to the desired temperature for the desired amount of time.

FIG. 25B and FIG. 25C describes in more detail the principle of magnetic bead capture, resuspension and travel between fluidic wells to accomplish sample preparation in the disclosed invention. The top actuator element 2502 has spatially oriented permanent magnets 2507 labeled 1, 3 and 5 and the bottom actuator element 2504 has spatially oriented permanent magnets labeled 2, 4 and 6. In this embodiment the microfluidic cartridge 2503 rotates anticlockwise between the stationary top actuator element 2502 and bottom actuator element 2504. The microfluidic cartridge rotates to a position where the "bind" well comes under the top permanent magnet "1", causing the magnetic beads to be attracted to it and captured at the top of the "bind" well. The microfluidic cartridge continues to rotate and moves the beads into the next well labeled "wash" through the connecting oil filled fluidic conduit. The side wall of the "wash" well functions as a physical barrier along the path of the magnetic beads, that constrains the beads in the oil at the top of the wash well, as the permanent magnet "1" moves away such that its forces are no longer felt by the beads. As the microfluidic cartridge continues to rotate it comes to a position where the first"wash" well is is on top of the permanent magnet labeled "2" on the bottom actuator element. This causes the beads on the top of the first wash well to be attracted towards the permanent magnet "2" and get resuspended and captured in the wash buffer present at the bottom of the "wash" well. In a similar fashion the magnetic beads are resuspended, captured and moved by the magnets 3, 4, 5, and 6 until they reach the "elution" well where the nucleic acids on the beads are eluted into the buffer solution present in the bottom of the "elution" well.

Figure 26A:
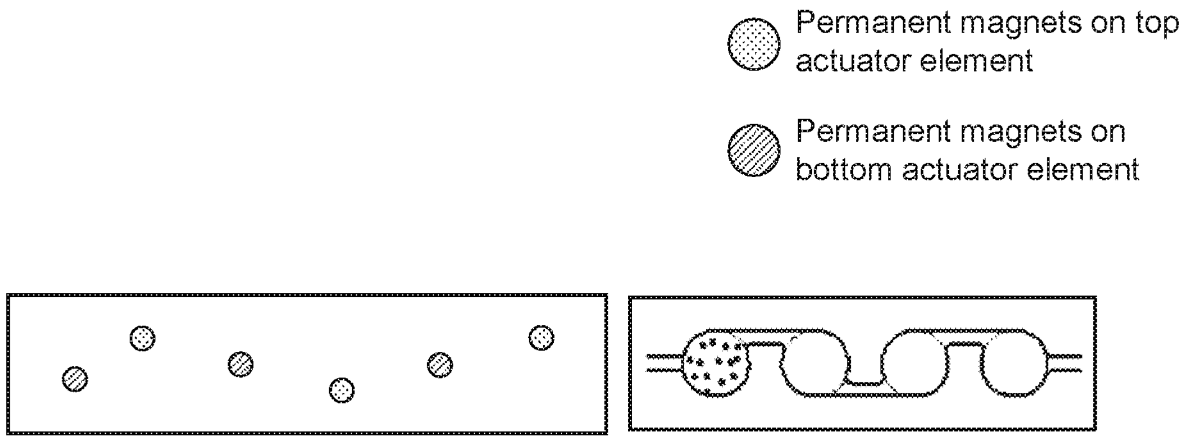
Figure 26B:
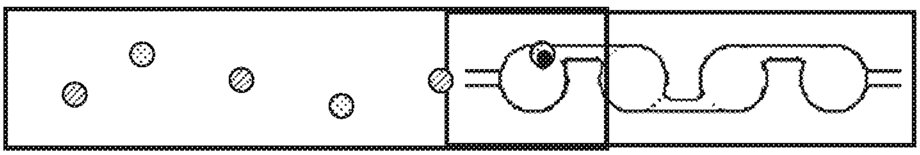
Figure 26C:
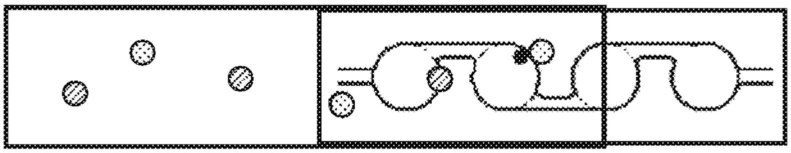

Referring to FIG. 26A to FIG. 26I, different instances of the position of the microfluidic cartridge with respect to the actuator element, to illustrate the principle of magnetic bead capture, resuspension and travel between fluidic wells using linear actuation is shown. The actuator element comprises top and bottom permanent magnets. FIG. 26A shows the starting position where none of the wells within range of the magnetic field. At FIG. 26B, the first top permanent magnet comes in proximity with the first well, thereby capturing the magnetic beads in the oil present in the primary fluidic conduit. The captured magnetic beads are moved to the second well through the primary fluidic conduit as seen in FIG. 26C.

Here, the wall of the second fluidic well obstructs their path and they remain constrained in the second fluidic well.

Figure 26D:
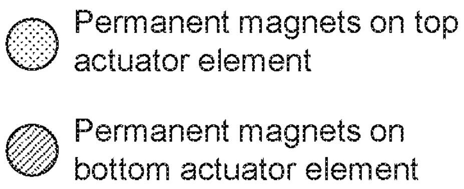
Figure 26D:
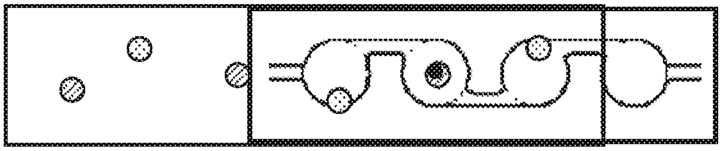
Figure 26E:
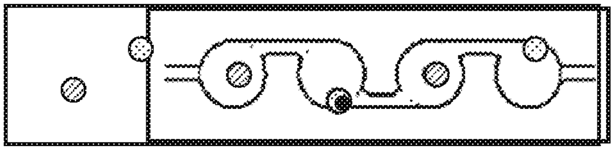
Figure 26F:
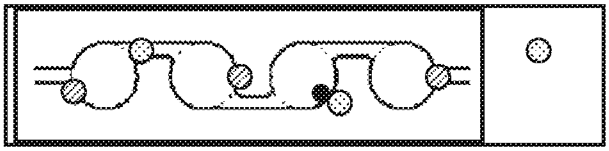
Figure 26G:
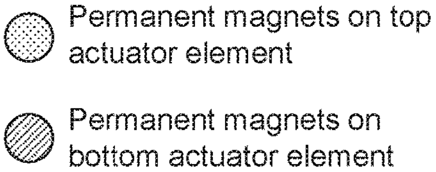
Figure 26G:
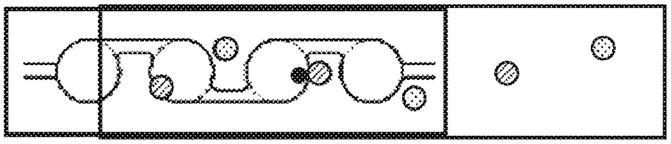
Figure 26H:
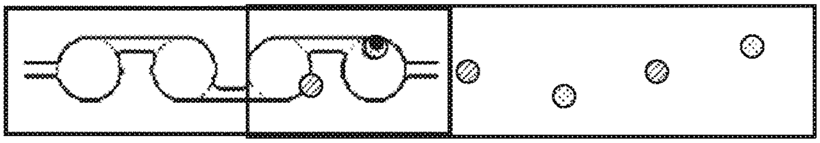
Figure 26I:
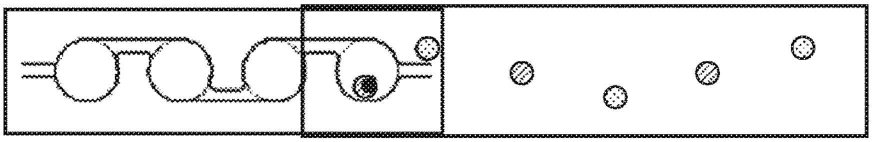

FIG. 26D shows a position where the first bottom permanent magnet comes in proximity to the second fluidic well, thereby attracting the beads to the bottom of the fluidic well where it is re-suspended in the buffer reagent present in the fluidic well. FIG. 26E shows the position where the second top permanent magnet comes in proximity with the second well and drags the beads through the primary fluidic conduit into the third fluidic well. FIG. 26F shows the beads constrained to the third fluidic well as its side-wall acts as a baffle. In FIG. 26G, the second bottom permanent magnet comes in proximity to the third well and attracts the beads to the bottom of the well thereby resuspending them in the buffer present at the bottom. In FIG. 26H the beads are attracted to the top by the third top permanent magnet and are transferred to the fourth fluidic well through the primary fluidic conduit. In FIG. 26I the third bottom permanent magnet attracts the beads to the bottom of the fourth fluidic well thereby resuspending the beads in the buffer present in the fourth fluidic well.

Figure 27A:
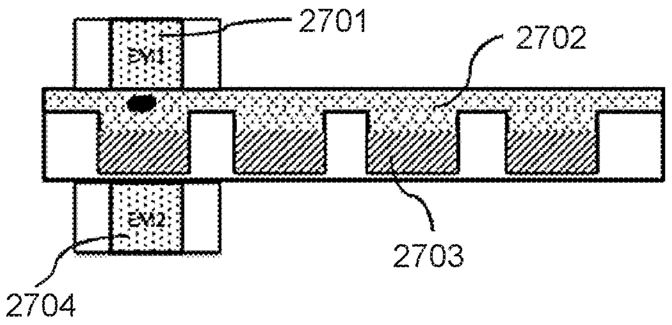
Figure 27B:
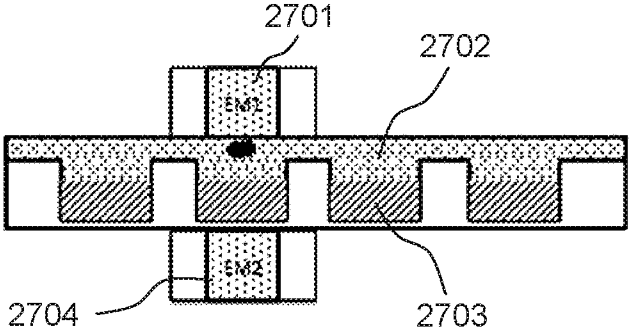
Figure 27C:
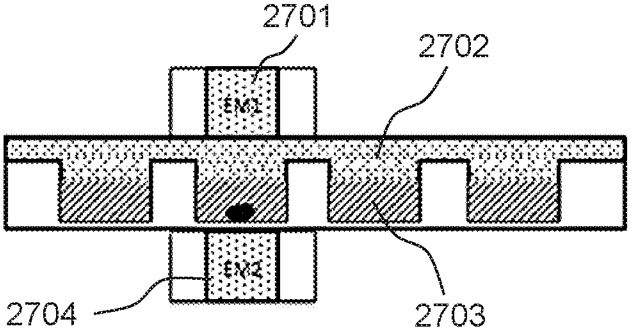
Figure 27D:
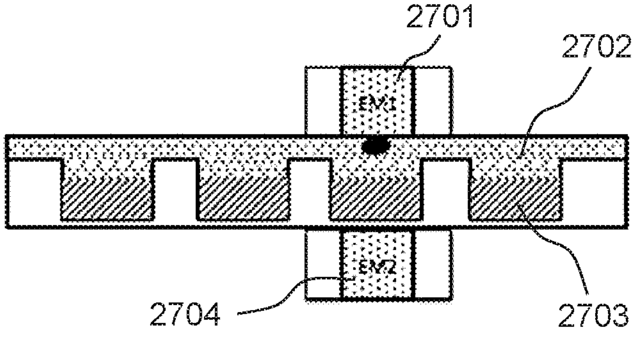
Figure 27E:
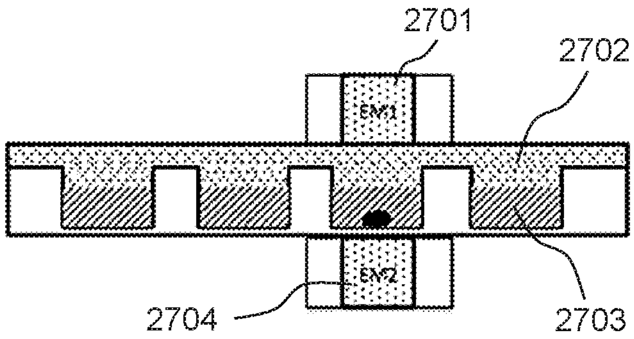
Figure 27F:
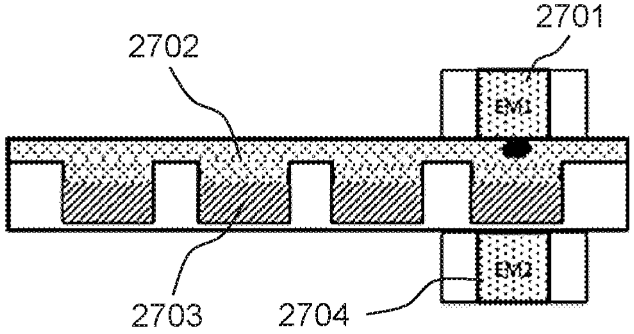
Figure 27G:
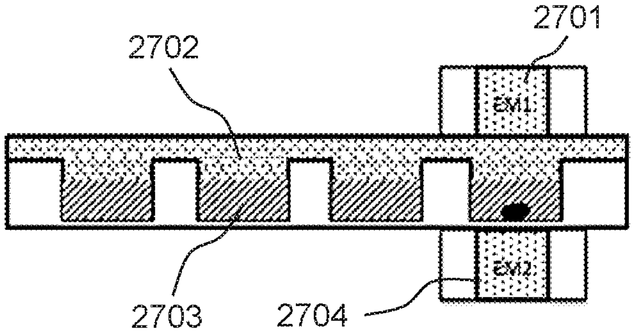

The permanent magnets may be replaced with electromagnets as shown in FIGS. 27A-27G. The microfluidic cartridge moves between the actuator elements comprising electromagnets. The top or the bottom electromagnet may be turned on or off in a sequence to facilitate the moving and resuspending of the magnetic beads between the different fluidic wells 2703. FIGS. 27A-27G represents different instances of the magnetic bead travel through a sample processing sequence. At the instance shown in FIG. 27A, electromagnet EM1 2701 is turned ON to capture the beads in the oil phase 2702. The beads are moved through the oil phase as EM1 is kept ON as seen in instance shown in FIG. 27B. At the instance in FIG. 27C, EM1 is turned OFF and EM2 2704 is turned ON. This results in the beads getting attracted towards EM2, resulting in the resuspension of the beads into the reagent 2703 in its fluidic well. When the beads are ready to be moved to the next fluidic well, EM1 is turned back ON, thus attracting the beads towards it into the oil phase. At the instance shown in FIG. 27D, the beads are moved over the next reagent filled fluidic well. EM1 is then turned OFF and EM2 is turned ON, causing the beads to resuspend through the reagent filled in the fluidic well before getting captured by EM2 as shown in FIG. 27E. Finally in FIGS. 27F and 27G the beads are moved and resuspended through the last fluidic well by selectively turning ON and OFF EM1 or EM2 in the desired timing sequence. The top and bottom electromagnets may be pulsed alternatively, so as to achieve mixing and resuspension of the beads in a reaction well. While electromagnets can be used instead of permanent magnets and baffles, they require electric power supply and a electronic controller for switching ON and OFF, thus complicating the instrumentation requirements. As such it is not as appealing as using permanent magnets, particularly in point of care and low resource settings.

The invention disclosed describes a method and device for fluidic handling on a microfluidic cartridge. The microfluidic device comprises one or more stored reagent filled pouches with frangible seals, and actuator elements comprising one or more protrusions that are spatially oriented so as to dispense reagents into the wells of a fluidic cartridge in a predefined sequence as the cartridge slide in between the actuator elements.

Referring to FIG. 28, a perspective view of a microfluidic cartridge and actuator element for sequential reagent delivery for sample preparation using magnetic beads. The microfluidic cartridge has on-board stored reagents in reagent pouches 2803 sealed with a frangible seal, such that when force is applied, the seal breaks and releases the reagents into a well on the microfluidic cartridge through a fluidic conduit. The reagent pouches are spatially oriented such that when the microfluidic cartridge mates with the actuator element and slides in between it from one end to the other, the pouches are squeezed to deliver reagents sequentially. The fluidic wells have one or more top baffles 2804 and bottom baffles 2802 that serve to constrain the beads in a well. The actuator element has one or more mechanical elements (e.g., protrusions, plungers, or the like) on it 2806, so arranged such that it functions to squeeze the reagent pouches and dispense their reagents into the wells on the microfluidic cartridge. The mechanical elements are designed such that they keep the reagent pouches squeezed for the entire sample-to-answer sequence to prevent backflow. In some embodiments the mechanical elements may serve to open and close a pinch style valve on the microfluidic cartridge, in a predefined sequence so as to control the direction of fluid flow on the microfluidic cartridge or open or close a vent. The actuator element also may have one or more fixed magnets on it. As seen in FIG. 28, the actuator element has top magnets 2805 and bottom magnets 2807 that are spatially arranged such that they capture, resuspend and move the magnetic beads into the different fluidic wells to complete a sample preparation sequence.

Figure 29A:
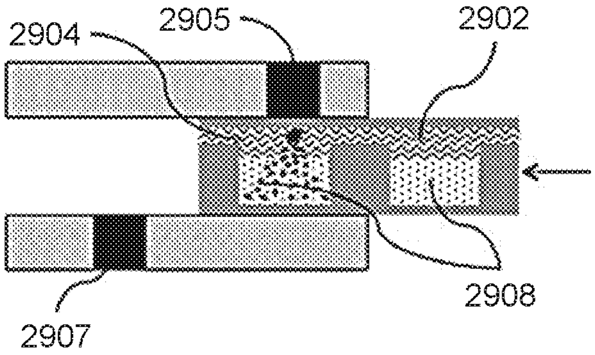
Figure 29B:
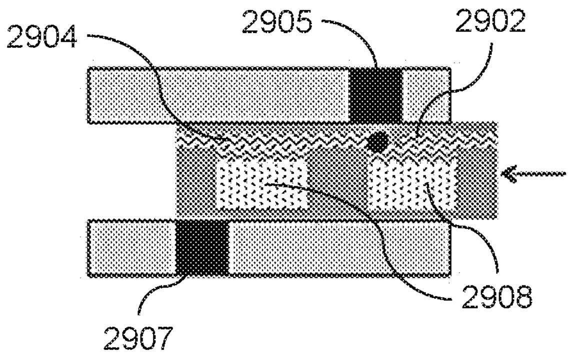
Figure 29C:
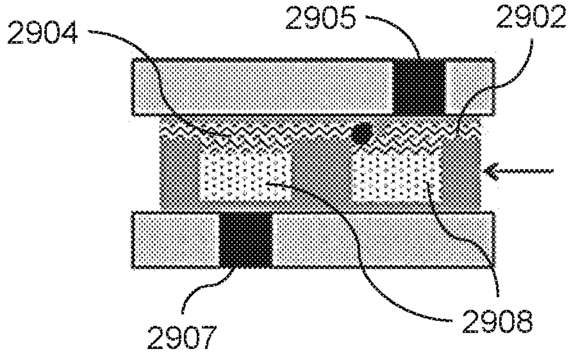
Figure 29D:
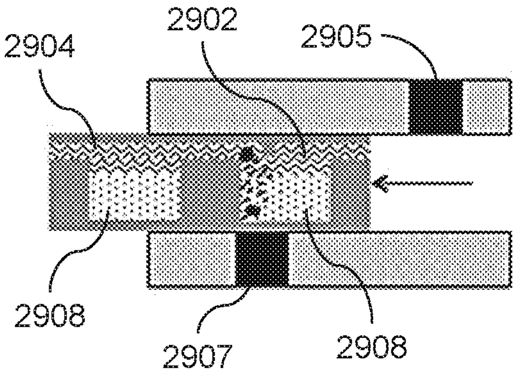
Figure 29E:
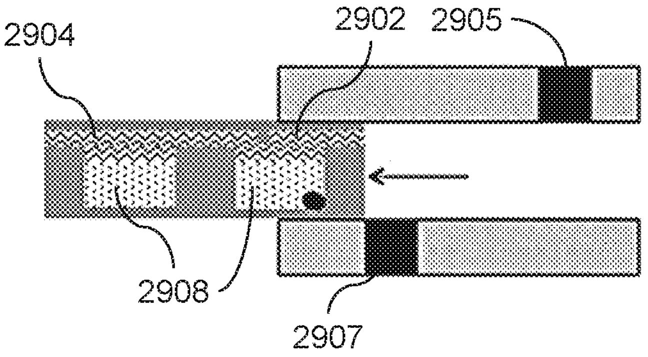

In some embodiments, the beads may be transferred directly into the LAMP or other NAAT amplification system and eluted directly in the system. This enables all the captured nucleic acids to be inputted into the NAAT amplification system. FIGS. 29A-29E illustrate the principle of using protrusions as baffles in the fluidic well to constrain the beads to a well as the magnet continues to move along a path of motion. The fluidic well has a protrusion on the top 2902 that acts to constrain the beads as the magnet continues to move along its path of motion. The reagents 2908 are separated by an immiscible oil phase 2904 in the cross sectional schematic microfluidic device shown in FIGS. 29A-29E. A top fixed magnet 2905 and bottom fixed magnet 2907 are present on the top and bottom actuator elements of the microfluidic device respectively. When the top fixed magnet 2905 comes in proximity to the first fluidic well as seen in FIG. 29A, the magnetic beads present in it are attracted towards the magnet and captured on the top in the oil phase. As the microfluidic cartridge continues to move between the actuator elements, the beads are moved through the fluidic conduit and enter the second fluidic well as seen in FIG. 29B. Here, the protrusion 2902 acts to constrain the beads to the second well as the microfluidic device continues to move out of the magnetic field of the top magnet as seen in FIG. 29C. The magnetic beads constrained in the oil phase can then be moved through the miscible reagents at the bottom of the well when a bottom magnet comes in proximity with the fluidic well as seen in FIG. 29D. Here, the magnetic beads that were captured on the top are attracted towards the bottom magnet 2907 and thus are made to resuspend and move through the reagents present at the bottom of the fluidic well. In FIG. 29E, the magnetic beads are captured at the bottom of the well as the side-wall acts as a baffle, to prevent the beads from moving out of the well. This method can be used to move magnetic beads between chambers or wells on a microfluidic device for sample processing, using spatially oriented baffles and permanent magnets.

In one embodiment a lancet with a hollow channel or a needle may be actuated by the actuating element to pierce the wall of the amplification chamber and transfer the fluid to a lateral flow strip for detection. FIGS. 30A-30B illustrate the principle of moving liquid product containing the analyte to be detected, from the fluidic well 3002 to a lateral flow strip 3003. FIG. 30A shows the lancet 3005 with a hollow channel 3004 before actuation. FIG. 30B shows the hollow lancet after actuation, where it pierces through the lateral flow strip and the bottom of the fluidic well thus creating a conduit for fluid flow to the lateral flow strip.

Depending on the application and user requirements, the sample processing system may integrate motors, actuators, heating elements, thermocouples, fans, cooling units, micro-controllers, optical detectors, electrodes, filters, light sources, battery packs, wireless modules, and electronics such that it forms a single, self-contained, self-sufficient integrated system for performing biological sample processing. The volume of reagent pouches, reservoirs and reaction chambers may vary depending on the bioassay and the needs of the user. Typical volumes can range from 1 ul to 10 ml or from 5 ul to 1 ml. There are many suitable materials for the microfluidic device such as glass, polycarbonate, PMMA, COC, silicon or a combination of one or more of the materials. A microfluidic device may be polymer injection molded with integrated silicon or glass MEMS functionalized electrode array or a microarray, or a lateral flow strip for detection. The material may be chosen based on the requirements of the user and the assay being performed on it, based on its biocompatibility, chemical compatibility. The footprint of the microfluidic device may range from a few square millimeters to few tens of square centimeters depending on the user requirements and the sample processing application. In some embodiments, multiple microfluidic devices may be stacked or arrayed and processed in parallel. The pull forces, shapes and sizes of the magnets in the sample processing system will be chosen depending on the sample processing needs, shape, size, volume, material properties and rupture pressure of frangible seal. The frangible seal materials include aluminum foils, polymers, rubber, metals, adhesive tapes, metal oxides or a combination of materials.

General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

"Nucleic acid" as used herein means a polymeric compound comprising covalently linked subunits called nucleotides. A "nucleotide" is a molecule, or individual unit in a larger nucleic acid molecule, comprising a nucleoside (i.e., a compound comprising a purine or pyrimidine base linked to a sugar, usually ribose or deoxyribose) linked to a phosphate group.

"Polynucleotide" or "oligonucleotide" or "nucleic acid molecule" are used interchangeably herein to mean the phosphate ester polymeric form of ribonucleosides (adenosine, guanosine, uridine or cytidine; "RNA molecules" or simply "RNA") or deoxyribonucleosides (deoxyadenosine, deoxyguanosine, deoxythymidine, or deoxycytidine; "DNA molecules" or simply "DNA"), or any phosphoester analogs thereof, such as phosphorothioates and thioesters, in either single-stranded or double-stranded form. Polynucleotides comprising RNA, DNA, or RNA/DNA hybrid sequences of any length are possible. Polynucleotides for use in the present invention may be naturally-occurring, synthetic, recombinant, generated ex vivo, or a combination thereof, and may also be purified utilizing any purification methods known in the art. Accordingly, the term "DNA" includes but is not limited to genomic DNA, plasmid DNA, synthetic DNA, semisynthetic DNA, complementary DNA ("cDNA"; DNA synthesized from a messenger RNA template), and recombinant DNA (DNA that has been artificially designed and therefore has undergone a molecular biological manipulation from its natural nucleotide sequence).

"Amplify," "amplification," "nucleic acid amplification," or the like, refers to the production of multiple copies of a nucleic acid template (e.g., a template DNA molecule), or the production of multiple nucleic acid sequence copies that are complementary to the nucleic acid template (e.g., a template DNA molecule).

The terms "top," "bottom," "over," "under," and "on" are used throughout the description with reference to the relative positions of components of the described devices, such as relative positions of top and bottom substrates within a device. It will be appreciated that the devices are functional regardless of their orientation in space.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, CA), fluorescent microparticles and nanoparticles, coated magnetic microparticles and nanoparticles, ferromagnetic microparticles and nanoparticles, coated ferromagnetic microparticles and nanoparticles. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as Fe304, BaFel2019, CoO, NiO, Mn203, Cr203, and CoMnP.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A microfluidic device comprising:

a microfluidic cartridge comprising a plurality of fluidic wells comprising at least a first, a second, and a third fluidic well each configured to receive magnetic beads, a primary fluidic conduit comprising at least a first fluidic conduit segment connecting said first fluidic well to said second fluidic well and a second fluidic conduit segment connecting said second fluidic well to said third fluidic well;

wherein said first and second fluidic conduit segments are alternately offset such that in combination said first and second fluidic conduit segments do not form a straight line segment;

at least one actuation element each comprising a planar surface and at least a first permanent magnet and a second permanent magnet spatially arranged on said planar surface;

wherein said microfluidic cartridge is proximately positioned to said planar surface of said at least one actuation element;

wherein said first permanent magnet is alternately offset from said second permanent magnet and wherein said first permanent magnet positionally corresponds to said first fluidic conduit segment for movement of said magnetic beads therethrough and said second permanent magnet positionally corresponds to said second fluidic conduit segment for movement of said magnetic beads therethrough.

2. The microfluidic device of claim 1 wherein said at least one actuation element is disk shaped and adapted for rotation about a central axis.

3. The microfluidic device of claim 1 wherein said microfluidic cartridge or said at least one actuation element is adapted for linear motion.

4. The microfluidic device of claim 1 wherein said at least one actuation element comprises a single actuation element.

5. The microfluidic device of claim 4 wherein said microfluidic cartridge or said single actuation element is adapted for linear motion.

6. The microfluidic device of claim 1 wherein said microfluidic cartridge further comprises a plurality of reagent dispensing units.

7. The microfluidic device of claim 6 wherein said plurality of reagent dispensing units are connected to said primary fluidic conduit and/or a plurality of inlet fluidic conduits.

8. The microfluidic device of claim 7 wherein said plurality of reagent dispensing units comprise:

an immiscible reagent dispensing unit connected to said primary fluidic conduit for introducing an immiscible reagent therein; and a plurality of miscible reagent dispensing units each directly connected to a respective fluidic well by a respective inlet fluidic conduit for introducing a miscible reagent into each fluidic well.

9. The microfluidic device of claim 6 wherein said plurality of reagent dispensing units comprise a miscible reagent, an immiscible reagent, or a combination thereof.

10. The microfluidic device of claim 1 wherein each of the at least one actuation element further comprises a plurality of protrusions spatially arranged on said planar surface.

11. The microfluidic device of claim 1 wherein the at least one actuation element comprises a first actuation element and a second actuation element and wherein said microfluidic cartridge is positioned between said first and second actuation element.

12. The microfluidic device of claim 11 wherein said at least a first permanent magnet is positioned on said planar surface of said first actuation element and said second permanent magnet is positioned on said planar surface of said second actuation element.

13. The microfluidic device of claim 1 wherein at least one of said first, second, and third fluidic wells comprises a baffle configured to constrain the beads in a fixed position within the at least one of the first, second and third fluidic wells and prevent the beads from moving further in the direction of said plurality of permanent magnets.

14. A method for preparation of biological samples comprising:

providing a microfluidic device comprising, a microfluidic cartridge comprising a plurality of fluidic wells at least one of which is configured to receive magnetic beads and at least one reagent pouch comprising a stored reagent;

a first actuation element and a second actuation element each comprising a planar surface and at least one permanent magnet mounted to said planar surface, wherein said at least one permanent magnet mounted to said first actuation element's planar surface is offset from said at least one permanent magnet mounted to said second actuation element's planar surface;

wherein said microfluidic cartridge or said first and second actuation elements is configured to rotate about a central axis;

introducing a biological sample into said microfluidic cartridge and isolating a target analyte from said biological sample;

binding said target analyte to said magnetic beads;

bursting and releasing said stored reagent from said at least one reagent pouch through force applied by at least one protrusion upon said at least one reagent pouch; and moving said magnetic beads bound to said target analyte between fluidic wells through rotation of said microfluidic cartridge or said first and actuation elements.

15. The method of preparation of biological samples of claim 14 wherein said first and second actuation elements further comprise a plurality of protrusions spatially arranged thereon.

16. The method of preparation of biological samples of claim 14 wherein said microfluidic cartridge is positioned between said first and second actuation element.

17. A microfluidic device comprising:

one or more actuation elements comprising a track, at least one carriage slidably engaged to said track, at least one magnet mounted to said at least one carriage, and a sliding rail upon which said at least one carriage is mounted; and a microfluidic cartridge comprising a plurality of fluidic wells adapted to receive magnetic beads onto which biomolecules are bound;

wherein said at least one carriage is slidably engaged to said track and to said sliding rail wherein said at least one carriage is configured to move in direction A along said sliding rail and in direction B as the at least one carriage progresses along said track to ensure proper magnet positioning;

wherein said direction A is substantially vertical and said direction B is substantially perpendicular to said direction A; and wherein said at least one magnet is adapted to carry said magnetic beads through said plurality of fluidic wells as said at least one carriage and said at least one magnet moves along said track and said sliding rail.

18. A method for preparation of biological samples comprising:

providing a microfluidic diagnostic apparatus comprising:

(i) a microfluidic cartridge comprising a plurality of fluidic wells, wherein at least one fluidic well of said plurality of fluidic wells comprises magnetic beads; and (ii) one or more actuation elements comprising a track, at least one magnet, at least one carriage slidably engaged to said track and upon which said at least one magnet is mounted, and a sliding rail upon which said at least one carriage is mounted;

wherein said at least one carriage is slidably engaged to said track and to said sliding rail and said at least one carriage is configured to move in direction A along said sliding rail and in direction B as the at least one carriage progresses along said track to ensure proper magnet positioning;

wherein said direction A is substantially vertical and said direction B is substantially perpendicular to said direction A;

wherein said at least one magnet mounted to said at least one carriage is adapted to carry said magnetic beads as said at least one carriage and said at least one magnet moves along said track and said sliding rail;

binding biomolecules to said magnetic beads; and moving said magnetic beads bound to said biomolecules between said plurality of fluidic wells through movement of said one or more actuation elements along said track.

* * * * *